United States Patent
Durst et al.

(10) Patent No.: US 11,802,118 B2
(45) Date of Patent: Oct. 31, 2023

(54) METHODS FOR EXTRACTION, PROCESSING, AND PURIFICATION OF A SELECTED FAMILY OF TARGET COMPOUNDS FROM CANNABIS

(71) Applicant: Nectar Health Sciences Inc., Victoria (CA)

(72) Inventors: Tony Durst, Ottawa (CA); Jay Van Der Vlugt, Victoria (CA); Amanda Saikaley, Ottawa (CA)

(73) Assignee: Nectar Health Sciences Inc., Victoria (CA)

( * ) Notice: Subject to any disclaimer, the term of this patent is extended or adjusted under 35 U.S.C. 154(b) by 31 days.

(21) Appl. No.: 17/617,341

(22) PCT Filed: Jun. 12, 2020

(86) PCT No.: PCT/CA2020/050824
§ 371 (c)(1),
(2) Date: Dec. 8, 2021

(87) PCT Pub. No.: WO2020/248076
PCT Pub. Date: Dec. 17, 2020

(65) Prior Publication Data
US 2022/0220057 A1 Jul. 14, 2022

Related U.S. Application Data

(60) Provisional application No. 62/891,013, filed on Aug. 23, 2019, provisional application No. 62/860,382, filed on Jun. 12, 2019.

(51) Int. Cl.
| | | |
|---|---|---|
| C07D 311/80 | (2006.01) | |
| C07C 211/63 | (2006.01) | |
| C07C 215/40 | (2006.01) | |
| C07D 453/04 | (2006.01) | |
| C07D 487/04 | (2006.01) | |
| C07D 487/08 | (2006.01) | |
| C07C 51/43 | (2006.01) | |
| C07C 65/19 | (2006.01) | |

(52) U.S. Cl.
CPC ............ *C07D 311/80* (2013.01); *C07C 51/43* (2013.01); *C07C 65/19* (2013.01); *C07C 211/63* (2013.01); *C07C 215/40* (2013.01); *C07D 453/04* (2013.01); *C07D 487/04* (2013.01); *C07D 487/08* (2013.01)

(58) Field of Classification Search
USPC ........................................................ 562/469
See application file for complete search history.

(56) References Cited

U.S. PATENT DOCUMENTS

| | | |
|---|---|---|
| 7,700,368 B2 | 4/2010 | Flockhart et al. |
| 9,376,367 B2 | 6/2016 | Herkenroth et al. |
| 9,730,911 B2 | 8/2017 | Verzura et al. |
| 9,765,000 B2 | 9/2017 | Nadal Roura |
| 10,059,684 B2 | 8/2018 | Changoer et al. |
| 10,239,808 B1 | 3/2019 | Black et al. |
| 10,246,431 B2 | 4/2019 | Changoer et al. |
| 10,406,453 B2 | 9/2019 | Ko et al. |
| 10,413,843 B2 | 9/2019 | Ko et al. |
| 10,478,747 B2 | 11/2019 | Ko |

FOREIGN PATENT DOCUMENTS

| | | |
|---|---|---|
| CA | 2866787 A1 | 4/2013 |
| WO | 2019/057994 A1 | 3/2019 |
| WO | 2019043259 A1 | 3/2019 |
| WO | 2019071213 A1 | 4/2019 |
| WO | 2020/016875 A1 | 1/2020 |
| WO | 2020/248076 A1 | 12/2020 |

OTHER PUBLICATIONS

International Search Report issued in Application No. PCT/CA2020/050825, dated Aug. 25, 2020 (3 pages).
Written Opinion issued in International Application No. PCT/CA2020/050825, dated Aug. 25, 2020 (6 pages).
Notice of Allowance issued in corresponding CA Application No. 3,111,964 dated May 21, 2021 (1 page).
Examiner's Requisition issued in Canadian Application No. 3,111,964, dated Apr. 27, 2021 (3 pages).

*Primary Examiner* — Ana Z Muresan
(74) *Attorney, Agent, or Firm* — Osha Bergman Watanabe & Burton LLP

(57) ABSTRACT

Disclosed are methods for separating, recovering, and purifying cannabidiolic acid (CBDA) salts from an organic solvent solution comprising a mixture of cannabinoids. The methods comprise solubilizing the mixture of cannabinoids in C5-C7 hydrocarbon solvents, adding thereto a selected amine to thereby precipitate a CBDA-amine salt therefrom, dissolving the recovered CBDA-amine salt in a selected solvent and then adding thereto a selected antisolvent to thereby recrystallizing a purified CBDA-amine salt therefrom. The recrystallized CBDA-amine salt may be decarboxylated to form a mixture of cannabidiol (CBD) and amine. The CBD amine mixture may be acidified to separate the amine from CBD. The recovered CBD may be concentrated to produce a highly purified CBD. Also disclosed are CBDA-amine salts produced with certain amines selected from groups of secondary amines, tertiary amines, diamines, amino alcohols, amino ethers, and highly basic amines.

22 Claims, 40 Drawing Sheets

| | |
|---|---|
| Compound: | CBG |
| Signal: | DAD1A |
| Exp. RT: | 5.490 |
| Corr. Coeff.: | 0.999159 |
| Residual: | 18.68113 |
| RF RSD%: | |
| R^2: | 0.99832 |
| Formula: | y = ax + b |
| a: | 2.11730 |
| b: | 0.00000 |
| c: | 0.00000 |

| | |
|---|---|
| Compound: | CBD-A |
| Signal: | DAD1A |
| Exp. RT: | 5.793 |
| Corr. Coeff.: | 0.998372 |
| Residual: | 49.01184 |
| RF RSD%: | |
| R^2: | 0.99675 |
| Formula: | y = ax + b |
| a: | 4.00390 |
| b: | 0.00000 |
| c: | 0.00000 |

| | |
|---|---|
| Compound: | CBG-A |
| Signal: | DAD1A |
| Exp. RT: | 6.511 |
| Corr. Coeff.: | 0.998842 |
| Residual: | 43.52347 |
| RF RSD%: | |
| R^2: | 0.99768 |
| Formula: | y = ax + b |
| a: | 4.21677 |
| b: | 0.00000 |
| c: | 0.00000 |

| | |
|---|---|
| Compound: | CBN |
| Signal: | DAD1A |
| Exp. RT: | 6.843 |
| Corr. Coeff.: | 0.999215 |
| Residual: | 43.78864 |
| RF RSD%: | |
| R^2: | 0.99843 |
| Formula: | y = ax + b |
| a: | 5.15539 |
| b: | 0.00000 |
| c: | 0.00000 |

| | |
|---|---|
| Compound: | Δ9-THC |
| Signal: | DAD1A |
| Exp. RT: | 7.532 |
| Corr. Coeff.: | 0.999038 |
| Residual: | 19.36267 |
| RF RSD%: | |
| R^2: | 0.99608 |
| Formula: | y = ax + b |
| a: | 2.04445 |
| b: | 0.00000 |
| c: | 0.00000 |

| | |
|---|---|
| Compound: | Δ8-THC |
| Signal: | DAD1A |
| Exp. RT: | 7.811 |
| Corr. Coeff.: | 0.998742 |
| Residual: | 18.73847 |
| RF RSD%: | |
| R^2: | 0.99749 |
| Formula: | y = ax + b |
| a: | 1.74128 |
| b: | 0.00000 |
| c: | 0.00000 |

| | |
|---|---|
| Compound: | CBC |
| Signal: | DAD1A |
| Exp. RT: | 8.545 |
| Corr. Coeff.: | 0.999200 |
| Residual: | 41.44812 |
| RF RSD%: | |
| R^2: | 0.99840 |
| Formula: | y = ax + b |
| a: | 4.83302 |
| b: | 0.00000 |
| c: | 0.00000 |

| | |
|---|---|
| Compound: | THC-A |
| Signal: | DAD1A |
| Exp. RT: | 9.007 |
| Corr. Coeff.: | 0.998955 |
| Residual: | 30.12272 |
| RF RSD%: | |
| R^2: | 0.99781 |
| Formula: | y = ax + b |
| a: | 3.07164 |
| b: | 0.00000 |
| c: | 0.00000 |

METHODS FOR EXTRACTION, PROCESSING, AND PURIFICATION OF A SELECTED FAMILY OF TARGET COMPOUNDS FROM CANNABIS

CROSS-REFERENCE

This application claims the benefit of U.S. Provisional Patent Application No. 62/860,382 filed Jun. 12, 2019, its entire contents hereby incorporated by reference. This application also claims the benefit of U.S. Provisional Patent Application No. 62/891,013 filed Aug. 23, 2019, its entire contents hereby incorporated by reference.

TECHNICAL FIELD

Various embodiments disclosed herein generally relate to methods for processing and separating mixtures of phytochemicals extracted from plant biomass feedstocks. More specifically, this disclosure pertains to methods for separating and purifying cannabidiol compounds from cannabis biomass feedstocks.

BACKGROUND

Cannabaceae is a small family of flowering plants that includes about 170 species grouped in 11 genera that includes *Cannabis* (hemp, marijuana). It is well known that the number of species in the *Cannabis* genus is disputed. The *Cannabis* genus is most commonly considered to comprise one specie, i.e., *Cannabis sativa*. However, the *Cannabis* genus may be also be separated by some, into three subspecies i.e., *Cannabis sativa, Cannabis indica*, and *Cannabis ruderalis*. Furthermore, some consider that the *Cannabis* nomenclature includes *C. ruderalis*. It is to be noted that herein, the term *Cannabis* sp. is meant to include all species and subspecies of the *Cannabis* genus.

*Cannabis* sp. are known to produce at least 113 distinct cannabinoids and over 50 terpenes that are concentrated in viscous resins produced in plant structures known as glandular trichomes. Trichomes are located at about the axial growing tips of *Cannabis* plants. Perhaps the most recognized cannabinoids are tetrahydrocannabinol (THC) and cannabidiol (CBD). It is well known that THC has significant but temporary psychoactive effects (i.e., hallucinogenic) on mammalian physiology and for this reason, various formats of *Cannabis* sp. plant materials and extracts are consumed for recreational use. It is also well known that CBD does not have psychoactive effects (i.e., hallucinogenic) but does have significant calming and pain relief effects. As an aggregate group of compounds, *Cannabis* terpenes are known to provide characteristic distinct aromas and flavors. It is also known that terpenes interact with cannabinoids to modulate the physiological effects of cannabinoids.

It is also well known that fiber-type cannabis, commonly known as hemp, has relatively high levels of CBD with very low levels or no levels of THC and consequently, is considered to have no or only minimal psychoactive and/or anxiogenic effects. The term "hemp" derives its definition from legal and/or regulatory distinctions for fiber-type cannabis strains and cultivars that stably and reproducibly have less than 0.3% THC in the USA. In Canada, a "List of Approved Cultivars for the 2019 Growing Season: Industrial Hemp Varieties Approved for Commercial Production" released by Health Canada (world wide web: canada.ca/en/health-canada/services/druas-medication/cannabis/pro-ducina-sellina-hemp/commercial-licence/list-approved-cultivars-cannabis-sativa.html), listed 52 approved hemp cannabis cultivars for agricultural production in Canada.

Cannabinoid compounds used for both recreational and medicinal purposes are almost exclusively extracts that have been solubilized and recovered from cannabis plants.

The most commonly known and widely used cannabis extraction methods are based on the use of organic solvents. Some drawbacks associated with such methods include poor or inconsistent yields and high costs associated with extraction and purification of extract and toxicity of some of the extraction solvents. Government regulations and security for cannabis plants are also an important consideration that adds to the overhead cost of producing extracts containing cannabinoid compounds.

From a technical standpoint, conventional extraction methods using non-aqueous solvents, and the like, are too crude or too complex, inefficient, time consuming, and/or expensive. Conventional methods of extraction that have been used to extract and recover phytochemical constituents from botanical biomass include maceration processes, decoction processes, and extraction processes using aqueous and/or non-aqueous solvents. However, such extraction methods and processes do not retain many of the extracted target molecules after the solvents are removed. In particular, no conventional extraction technology provides an optimum system where desired target molecules are efficiently separated from a botanical biomass and dissolved into a solvent without concurrently extracting a high yield of undesirable wax and pigment molecules that decrease the purity and quality of the extract solution. Furthermore, solvents used in current botanical extraction methods cannot effectively removed be from the extracted materials without significant simultaneous loss of target molecules.

A significant challenge in assuring the delivery of consistent reproducible quality and content of extracts, including cannabinoid extracts from cannabis, is due to natural variations of endogenous phytochemicals that occur in plants. The chemical "fingerprint" of a particular botanical species can vary widely depending on the age of the plant, time of harvest, soil conditions, weather conditions, and a myriad of other factors. It is known that botanicals with very different phytochemical profiles will have different therapeutic effects, even if the botanicals are recovered from the same plant species. Standardization of botanical extraction processes facilitate the batch-to-batch reproducibility of a final product. A standardized extract has a selected concentration of a marker compound that is known to a high degree of accuracy, and because both the amount of botanical material that is extracted and the amount of a carrier that may be added can be varied, it is possible to compensate for natural variability in the plant material. Also, if endogenous phytochemical active components of a standardized botanical extract are administered to patients in known quantities, then the treatments following prognosis of a diseases can be monitored. Therefore, there is a need for standardized and reproducible extracts of botanicals, including extracts derived from cannabis.

SUMMARY

The embodiments of the present disclosure generally relate to methods for separating, recovering, and purifying cannabidiolic acid-amine (CBDA-amine) salts, cannabidiolic acid (CBDA), and cannabidiol (CBD) from crude extracts prepared from cannabis plant biomass feedstocks.

Some embodiments of the present disclosure generally relate to methods for solubilizing concentrated complex extract mixtures comprising cannabinoids and cannabis phytochemicals, that were solvent-extracted from cannabis biomass after which, the solvents may have been removed to thereby concentrate the extracts.

According to some aspects, the concentrated cannabis extract mixtures may be selectively solubilized in an organic solvent such as an alkane or a petroleum ether to thereby produce solvent-solubilized cannabis extract mixtures. Those skilled in this art will understand that petroleum ethers are distillation fractions of low molecular weight aliphatic hydrocarbons having low boiling point (b.p.) ranges of about 30° C. to about 100° C.

According to some aspects, a selected amine may be added to and commingled with a solvent-solubilized cannabis extract mixture to thereby precipitate a CBDA-amine salt. The precipitated CBDA-amine salt may be washed one or more times with a selected alkane and then dried to produce a dry purified CBDA-amine salt.

According to some aspects, a dried washed CBDA-amine salt may be purified by re-solubilization in a selected organic solvent after which, a purified CBDA-amine salt may be recrystallized from the solution by addition thereto of a selected antisolvent. Alternatively, a dried washed CBDA-amine salt may be solubilized into a solution by warming the CBDA-amine salt untilit is dissolved and then, the CBDA-amine salt may be recrystallized by cooling the solution. The purified recrystallized CBDA-amine salt may be washed one or more times with a selected alkane and then dried to produce a dried purified CBDA-amine salt.

According to some aspects, the purified CBDA-amine salt may be decarboxylated by adding and dissolving the CBDA-amine salt into a sodium carbonate solution and mixing the solution at about 100° C. for about 4 hr to thereby form an oil comprising CBD and the amine. The decarboxylated CBD may be dissolved into a selected alkane solvent or alternatively, may be dissolved into a low-boiling petroleum ether. The dissolved amine may then be partitioned from the dissolved CBD by the addition of aqueous HCl thereby forming an aqueous layer containing the amine therein, and an organic layer containing the CBD therein. After separation and removal of the aqueous layer, the solvent may then be removed from the organic layer thereby producing a highly purified CBD.

Some embodiments disclosed herein relate to methods for the use of selected amines to produce purified CBDA-amine salts. A selected amine may be added to an alkane-solubilized complex mixture of cannabinoids to precipitate therefrom a CBDA-amine salt. The precipitated CBDA-amine salt may be washed one or more times with a selected alkane solvent, and then dried to produce a purified CBDA-amine salt.

According to some aspects, a suitable amine for precipitating a CBDA-amine salt may be selected from a group of diamines, for example, 1,8-diazabicyclo[5.4.0]undec-7-ene (DBU), 1,5-diazabicyclo[4.3.0]non-5-ene (DBN), 1,4-diazabicyclo[2.2.2]octane (DABCO), 4 dimethylaminopyridine (DMAP), tetramethylethylenediamine (TMEDA), and the like.

According to some aspects, a suitable amine for precipitating a CBDA-amine salt may be selected from a group of amino alcohols such as dimethylethanolamine (DMEA), piperidineethanol, and the like.

According to some aspects, a suitable amine for precipitating a CBDA-amine salt may be selected from a group of tertiary amines, for example, triethylamine, tripropylamine, tributylamine, diisopropylethylamine (Hunig's base), quinine, and the like.

According to some aspects, a suitable amine for precipitating a CBDA-amine salt may be a primary amine such as dicyclohexylamine, or a secondary amine such as diethyl amine, pyrrolidine, and the like.

BRIEF DESCRIPTION OF THE DRAWINGS

The present invention will be described in conjunction with reference to the following drawings in which.

DETAILED DESCRIPTION

Figure 1A:
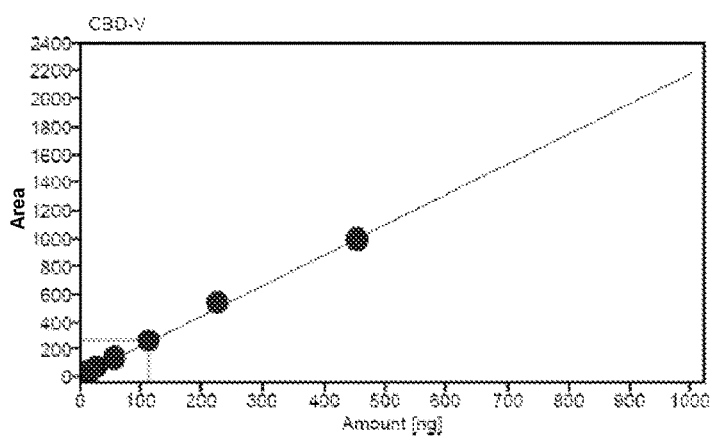
FIG. 1A is a chart showing a linear calibration curve for cannabidivarin (CBDV)

No language or terminology in this specification should be construed as indicating any non-claimed element as essential or critical. All methods described herein can be performed in any suitable order unless otherwise indicated herein. The use of any and all examples, or example language (e.g., "such as") provided herein, is intended merely to better illuminate example embodiments and does not pose a limitation on the scope of the claims appended hereto unless otherwise claimed.

It should be noted that if the stereochemistry of a structure or a portion of a structure is not indicated with, for example, bold or dashed lines, the structure or the portion of the structure is to be interpreted as encompassing all stereoisomers of it. Moreover, any atom shown in a drawing with unsatisfied valences is assumed to be attached to enough hydrogen atoms to satisfy the valences. In addition, chemical bonds depicted with one solid line parallel to one dashed line encompass both single and double (e.g., aromatic) bonds, if valences permit.

Throughout this specification, the word "comprise", or variations such as "comprises", "comprising", "including", "containing", and the like, will be understood to imply the inclusion of a stated element or integer or group of elements or integers but not the exclusion of any other element or integer or group of elements or integers, unless the context requires otherwise.

To facilitate understanding of the embodiments set forth herein, a number of terms are defined below. Generally, the nomenclature used herein and the laboratory procedures in biology, biochemistry, organic chemistry, medicinal chemistry, pharmacology described herein are generally well known and commonly employed in the art. Unless defined otherwise, all technical and scientific terms used herein generally have the same meaning as commonly understood in the art to which this disclosure belongs. In the event that there is a plurality of definitions for a term used herein, those in this written description shall prevail unless stated otherwise herein.

As used herein, the singular forms "a", "an", and "the," may also refer to plural articles, i.e., "one or more", "at least one", "and/or", are open-ended expressions that are both conjunctive and disjunctive in operation. For example, the term "a cannabinoid" includes "one or more cannabinoids". Further, each of the expressions "at least one of A, B, and C", "at least one of A, B, or C", "one or more of A, B, and C", "one or more of A, B, or C" and "A, B, and/or C" means A alone, B alone, C alone, A and B together, A and C together, B and C together, or A, B and C together. The term "an entity" refers to one or more of that entity. As such, the terms "a", "an", "one or more", and "at least one" can be used interchangeably herein.

Recitation of ranges of values herein are merely intended to serve as a shorthand method of referring individually to each separate value falling within the range, unless otherwise indicated herein, and each separate value is incorporated into the specification as if it were individually recited herein. Where a specific range of values is provided, it is understood that each intervening value, to the tenth of the unit of the lower limit unless the context clearly dictates otherwise, between the upper and lower limit of that range and any other stated or intervening value in that stated range, is included therein. All smaller subranges are also included. The upper and lower limits of these smaller ranges are also included therein, subject to any specifically excluded limit in the stated range.

The terms "about" or "approximately" as used herein, mean an acceptable error for a particular recited value, which depends in part on how the value is measured or determined. In certain embodiments, "about" can mean one or more standard deviations. When the antecedent term "about" is applied to a recited range or value it denotes an approximation within the deviation in the range or value known or expected in the art from the measurement method. For removal of doubt, it shall be understood that any range stated in this written description that does not specifically recite the term "about" before the range or before any value within the stated range inherently includes such term to encompass the approximation within the deviation noted above.

As used herein, the terms "cannabis" and "cannabis biomass" encompass whole *Cannabis sativa* plants and also parts thereof which contain cannabinoids and cannabis phytochemicals, such as the aerial parts of the plants or isolated leaves and/or flowering heads and/or seeds. The term also encompasses freshly harvested cannabis plant material and also plant material, cannabis plant material that was dried after harvesting. Dried cannabis plant material may be in a loose form or alternatively, may be baled into square bales or rectangular bales or round bales or alternatively, may be compressed into cubes or pellets or cubes. Dried cannabis plant material may be separated into two or more components wherein one component comprises the cannabis stalks and stems, and a second component comprises the leaves, trichomes, and flowers. The second component may be further separated into leaves and trichome/flower components and the trichome/flower components may be separated into trichome and flower components. The separated dried cannabis plant material components may be stored in a loose form and/or processed into a baled form and/or processed into a compressed form. The separated dried cannabis plant material components may be packaged and stored in a packaging material.

Freshly harvested and/or dried harvested cannabis biomass may be processed with a selected solvent to separate and recover therefrom in a crude extract, a complex mixture of cannabinoids and cannabis phytochemicals.

The term "cannabinoid" as used herein encompasses cannabidiol (CBD), cannabidiolic acid (CBDA), cannabinol (CBN), cannabigerol (CBG), cannabigerolic acid (CBGA), cannabichromene (CBC), cannabichromenic acid (CBCA), cannabicyclol (CBL), cannabivarin (CBV), cannabidivarin (CBDV), cannabidivarinic acid (CBDVA), cannabichromevarin (CBCV), cannabigerovarin (CBGV), cannabigerol monomethyl ether (CBGM), cannabielsoin (CBE), cannabicitran (CBT), among others. The term "cannabinoid" may also be substituted for herein by the acronym "CBD". The term "tetrahydrocannabinol" as used herein encompasses (−)-trans-Δ9-tetrahydrocannabinol (Δ9-THC), Δ8-tetrahydrocannabinol (Δ3-THC), iso-tetrahydrocannabinol, tetrahydrocannabinolic acid (THCA), tetrahydrocannabivarin (THCV), tetrahydrocannabivarinic acid (THCVA), among others. The term "tetrahydrocannabinol" may also be substituted for herein by the acronym "THC".

The term "cannabis phytochemicals" as used herein, refers to biologically active compounds produced by *Cannabis sativa* plants, and in particular, to mixtures of terpenes, terpenoids, flavonoids, alkaloids, lignans, omega fatty acids, pigments, and the like, that may be extracted and separated from cannabis biomass by solvent extraction. The term "phytochemical" as used herein, refers to a single biologically active compound that has been separated from a mixture of phytochemicals.

The term "solvent" as used herein, is used herein to denote a liquid or gas capable of dissolving a solid or another liquid or gas. Non-limiting examples of solvents include alcohols such as methanol, ethanol, propanol, isopropanol, butanol, alkanes such as hexane, heptane, pentane, and the like, ethyl acetate, acetone (also known as propanone), formic acid, dichloromethane, 1,4-dioxane, tetrahydrofuran, acetonitrile, toluene, methyl tert-butyl ether, supercritical carbon dioxide $CO_2$, subcritical $CO_2$, hot water, supercritical $H_2O$, subcritical $H_2O$, and the like.

As used herein, the term "antisolvent" refers to an organic solvent that may be used to precipitate a target compound or molecule from another solvent in which the target compound or molecule is completely dissolved whereby, as the antisolvent is added to the solvent containing the dissolved target compound or molecule, the precipitation process is initiated by nucleation of the target compound or molecule followed by the formation of solid particles. When an alcohol was a solvent selected for dissolution of a target compound or molecule, water may be a suitable antisolvent to precipitate the target compound or molecule.

The term "crude precipitate" as used herein means the solids and/or oils produced by a chemical reaction between a selected organic base with a mixture of cannabinoid carboxylic acids present in a crude cannabis extract. The "crude precipitate" may also be referred to herein as a "crude isolate" or a "carboxylic acid salt" or a "precipitated cannabinoid".

The term "purified precipitate" as used herein means the solids and/or oils remaining after the crude precipitate is washed with a selected solvent such as, for example, with ethyl acetate at 40° C. A purified precipitate may also be produced via a recrystallization process wherein the crude precipitate is dissolved in a heated solvent and then cooled to an appropriate temperature to induce crystallization. Alternatively, the crude precipitate may be dissolved in a solvent which readily dissolves both the desired purified precipitate and the impurities present in the crude precipitate, followed by addition of an antisolvent in which the desired precipitate is insoluble and the impurities remain in solution. Subsequent filtration yields the purified precipitate. The "purified precipitate" may also be referred as a "purified isolate" or a "purified cannabinoid precipitate" or a "purified cannabinoid carboxylic acid".

As used herein, the term a "standardized solvent-solubilized crude extract" refers to a crude extract that has been adjusted by the addition or removal of a solvent to adjust the concentrations therein of one or more bioactive markers, such as THCA, to a selected target range in comparison to the concentrations of the one or more bioactive markers in a reference solution, using analytical methods known to those skilled in these arts. For example suitable analytical methods include HPLC methods and the like.

Some embodiments disclosed herein relate to methods of separating and recovering CBDA from solubilized crude extracts comprising cannabinoids and other phytochemicals extracted and recovered from cannabis biomass feedstocks. The methods for specifically separating and recovering CBDA from solubilized crude cannabis extracts pertain to the use of one or more selected amines to selectively react with CBDA thereby forming CBDA-amine salts that precipitate out of crude cannabis solutions. The methods disclosed herein include steps for separating and recovering precipitated CBDA-amine salts from cannabis crude extract solutions, for washing recovered CBDA-amine salts to separate and remove therefrom other cannabinoids and cannabis phytochemicals that may have been recovered with the precipitated CBDA-amine salts, for further purifying and recrystallization of the washed CBDA-amine salts, for the preparation of purified crystalline CBDA, and for decarboxylating the purified CBDA-amine salts to produce purified CBD therefrom.

Without being bound by any theory of operation or mechanism of action, the examples of embodiments disclosed herein are based in part, on an unpredicted/unexpected discovery that use of an amine having a suitably placed heteroatom can effectuate the transfer of the acidic proton from the carboxylic acid to the amine by stable/strong hydrogen bonding in the ammonium ion, as shown below, and thereby drive the acid-base reaction to completion by facilitating the crystallization of the desired salt as shown in Eqn 1 and Eqn 2:

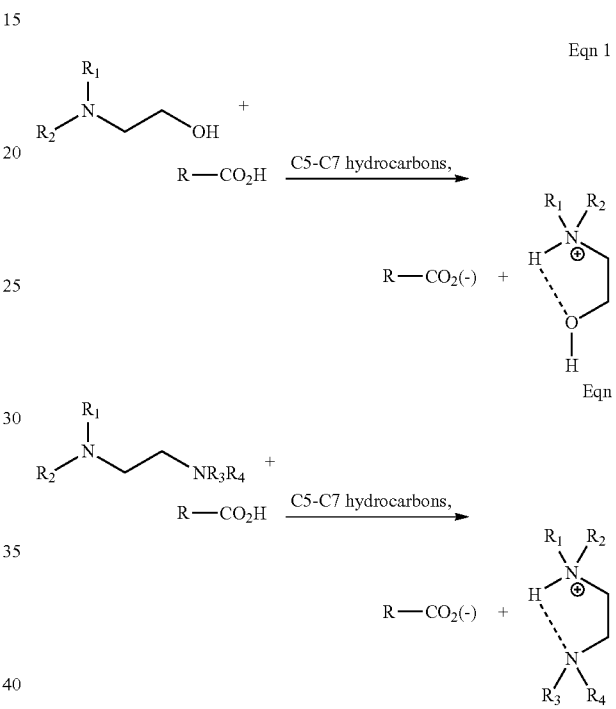

It was surprisingly discovered that some amines precipitated CBDA salts from crude cannabis extracts solubilized in certain organic solvents such as, for example, C5-C7 low-boiling hydrocarbon solvents including alkanes and petroleum ethers. The amine-precipitated CBDA salts, also referred to herein as CBDA-amine salts, have low or no solubility in a number of organic solvents at room temperature and therefore, may be washed with those organic solvents to produce highly purified CBD-amine salts.

According to one embodiment of the present disclosure, it was discovered that addition at room temperature of certain tertiary amines such as diisopropylethylamine (Hunig's base), triethylamine, tripropylamine, tributylamine, methyldicyclohexylamine, and quinine to solvent-solubilized crude cannabis extracts comprising complex mixtures of cannabinoids and cannabis phytochemicals, precipitated CBDA-amine salts from the crude extracts. It was also discovered that certain diamines such as N,N,N-trimethylethylenediamine, N,N,N,N-tetramethylethylenediamine, 4-aminomethylpiperidine, 1,5-diazabicyclooctane (DABCO), dimethylpiperazine, 4-dimethylaminopyridine (DMAP), 1,5-diazabicyclo(4.3.0)non-5-ene (DBN), and 1,8-diazabicycloundec-7-ene (DBU) precipitated CBDA-amine salts from solvent-solubilized crude cannabis extracts. It was also discovered that certain secondary amines such as diethylamine, N-isopropylcyclohexylamine, and 2,2,6,6-tertamethylpiperidine precipitated CBDA-amine salts from solvent-solubilized crude cannabis extracts. It was also discovered that certain amino alcohols such as piperidineethanol and N,N-dimethylethanolamine precipitated CBDA-amine salts from solvent-solubilized crude cannabis extracts. It was also discovered that certain amino ethers such as morpholine and N-methylmorpholine precipitated CBDA-amine salts from solvent-solubilized crude cannabis extracts. It was also discovered that cyclohexylamine (primary amine) precipitated CBDA-amine salts from solvent-solubilized crude cannabis extracts.

According to another embodiment of the present disclosure, CBDA-amine salts formed an oil and/or precipitated as a solids salt by a selected amine as disclosed herein, may be washed with a selected solvent to remove other cannabinoids and/or cannabis phytochemicals that may have remained associated with the recovered precipitated CBDA-amine salts. Suitable solvents for the washing step include C5-C7 alkanes such as heptane, pentane, hexane, low b.p. petroleum ethers (i.e., less than 100° C.), and the like.

According to another embodiment of the present disclosure, washed CBDA-amine salts may be further purified by addition and mixing into a heated mixture of a polar solvent and non-polar solvent to form a solution, and then, may be recrystallized back into a purified CBDA-amine salt by cooling or by the addition of an antisolvent. According to an aspect, a suitable polar solvent may be one of ethyl acetate, 95% ethanol, methanol, isopropanol, dichloromethane, toluene, methyl-tert-butyl ether (MTBE), tetrahydrofuran (THF), and the like. A particularly suitable polar solvent/non-polar solvent is a mixture of ethyl acetate with heptane. Suitable antisolvents for use with such solvents include C5-C7 alkanes and low b.p. petroleum ethers. Alternatively, washed CBDA-amine salts may be solubilized in an alcohol such as denatured ethanol or methanol, and then, may be recrystallized back into a purified CBDA-amine salt by cooling or by the addition of water as the antisolvent.

According to another aspect, a suitable ratio for the polar solvent/non-polar solvent mixture may be selected from a range of about 5:1 to about 20:1. A particularly suitable polar solvent/non-polar solvent ratio may be about 10:1, for example 10 parts ethyl acetate and 1 part heptane.

The CBDA-amine salts/polar solvent/non-polar solvent slurry is then cooled to about 30° C., and then may be placed into a 4° C. environment for a period of time selected from about 30 min to about 12 h during which time, purified CBDA-amine salt will recrystallize out of the polar solvent/non-polar solvent mixture. The recrystallized purified CBDA-amine salt may then be separated from the polar solvent/non-polar solvent mixture, for example, by filtration or centrifugation.

According to another embodiment of the present disclosure, purified CBDA-amine salts produced by the methods disclosed herein, may be decarboxylated and then separated by acidification to thereby produce a purified CBD.

According to another embodiment of the present disclosure, the CBDA-amine salts produced by the methods disclosed herein, may be acidified to separate the amines therefrom to produce highly purified CBDA.

According to some embodiments, crude extracts comprising cannabinoids and cannabis phytochemicals may be recovered from cannabis biomass feedstocks. A particularly suitable cannabis biomass feedstock for recovery of CBDA therefrom, comprises hemp cannabis plant biomass. The hemp plant biomass feedstock may comprise a plurality of freshly harvested whole plants, or alternatively, plant parts that have been separately recovered from the whole plants wherein the separate plant parts may be one or more of buds, flowers, seeds, bracts, leaves, chopped stems, and hurd that has been decorticated from the hemp stems. It is to be noted that the hemp biomass feedstock may comprise dried whole hemp plants that may have been baled or pelletized. It is to be noted that the separated hemp plant parts for example, the buds, the flower, the seeds, the chopped stems, the bracts, and the hurd, may be dried and then pelletized. Alternatively, the separated dried hemp parts may be provided as a loose feedstock. The hemp plant biomass feedstocks can be used in batch extraction processes and/or in continuous flow-through processes and/or in hybrid batch semi-continuous process. Solvents suitable for extraction of hemp plant biomass materials to produce crude extracts of phytochemicals therefrom include, for example, low chain alcohols such as methanol, ethanol, propanol, n-propanol, iso-pentanol, butanol, 2-propanone, among others. Suitable organic solvents also include ethers, ketones, C3-C7 alkanes, supercritical or subcritical carbon dioxide ($CO_2$), supercritical or subcritical water, 1,4-dioxane, tetrahydrofuran, acetonitrile, ketones such as acetone and methyl isobutyl ketone, esters such as methyl acetate and ethyl acetate, halogenated hydrocarbons such as chloroform, dichloromethane, and dichloromethane, and the like. If so desired, after recovery and separation from the cannabis plant biomass feedstock, the crude cannabis extracts may be concentrated by drying to a viscous form or a resinous form.

According to some embodiments, crude cannabis extracts may be diluted in a selected organic solvent prior to separating and recovering CBDA-amine salts therefrom. Suitable organic solvents for diluting crude cannabis extracts include C5-C7 hydrocarbon solvents such as alkanes and low b.p. petroleum ethers. Particularly suitable alkanes are heptane, hexane, and pentane.

According to some embodiments, a crude cannabis extract may be analyzed prior to dilution in a selected solvent, to determine its cannabinoid composition and to determine the content of CBDA therein on a mass basis. Then, the crude extract may be diluted with a selected organic solvent to adjust its CBDA content to within a selected target range. Suitable target ranges may be from about 20 mg/ml to about 445 mg/ml. Particularly suitable target ranges may be from about 27 mg/ml to about 200 mg/ml. Preferred target ranges may be from about 31 mg/ml to about 153 mg/ml.

An embodiment of the present disclosure pertains to an example method for separating out, recovering, and purifying CBDA in the form of a CBDA-amine salt, from a crude extract comprising a mixture of cannabinoids and cannabis phytochemicals recovered from processing cannabis biomass, and then converting the purified CBDA-amine salt into a purified CBD product. The example method comprises the steps of:

1. assaying a crude cannabis extract to determine the concentration of CBDA therein;
2. adding and commingling a first organic solvent with the crude cannabis extract to reduce the CBDA content therein to a level within a selected target range in reference to a CBDA standard, thereby producing a standardized solvent-solubilized crude cannabis extract;
3. adding and mixing into the standardized solvent-solubilized crude extract, a selected volume of a selected amine whereby the amine reacts with CBDA therein, thereby forming and precipitating a crude CBDA-amine salt;

4. separating and recovering the precipitated crude CBDA-amine salt from the standardized solvent-solubilized crude extract;
5. washing the recovered crude CBDA-amine salt with a selected second organic solvent one or more times to thereby produce a washed crude CBDA-amine salt;
6. re-solubilizing the washed CBDA-amine salt in a selected third organic solvent;
7 crystalizing the solubilized CBDA-amine salt by the addition of and mixing with a selected antisolvent and then cooling the mixture to thereby produce a crystallized purified CBDA-amine salt;
8. separating the crystallized purified CBDA-amine salt from the liquid phase, then washing and drying the purified CBDA-amine salt.
9. decarboxylating the purified CBDA-amine salt to produce an oil containing CBD and amine;
10. solubilizing the oil containing decarboxylated CBD and amine in a selected fourth organic solvent to thereby partition therefrom an organic layer containing a highly purified CBD oil and amine, and an aqueous layer;
11. separating the organic layer containing the highly purified CBD and amine from the aqueous layer;
12. acidifying the organic layer, for example with a mineral acid, such as for example aqueous HCl, to partition therefrom an organic layer containing the highly purified CBD in the form of an oil, and an aqueous layer containing the amine as its hydrochloride; and
13. removing the fourth organic solvent from the highly purified CBD.

According to an aspect, a suitable first organic solvent for use in step 2 may be a C5-C7 hydrocarbon such as an alkane or a low b.p. petroleum ether. Particularly suitable alkanes include heptane, hexane, pentane, their isomers, and the like. It is optional if so desired, to solubilize the crude cannabis extract in a selected volume of the first organic solvent prior to assaying the crude cannabis extract in step 1.

According to an aspect, a suitable target range for adjusting the CBDA content to in step 2 may be from about 20 mg/ml to about 445 mg/ml. A particularly suitable target range may be from about 27 mg/ml to about 200 mg/ml. A preferred target range may be from about 31 mg/ml to about 153 mg/ml.

According to another aspect, a suitable amine for use in step 3 may be a tertiary amine such as diisopropylethylamine (Hunig's base), triethylamine, methyldicyclohexylamine, tripropylamine, tributylamine, methyldicyclohexylamine, quinine, and the like. Alternatively, a suitable amine may be a diamine such as N,N,N-trimethylethylenediamine, N,N,N,N-tetramethylethylenediamine, 4-aminomethylpiperidine, DABCO, DMAP, DBN, DBU, dimethylpiperazine, and the like. Alternatively, a suitable amine may be a secondary amine such as N-isopropylcyclohexylamine, diethylamine, and 2,2,6,6-tertamethylpiperidine, and the like. Alternatively, a suitable amine may be an amino alcohol such as piperidineethanol and N,N-dimethylethanolamine, and the like. Alternatively, a suitable amine may be an amino ether such as morpholine, N-methylmorpholine, and the like. Alternatively, a suitable amine may be cyclohexylamine.

According to another aspect, the standardized solvent-solubilized crude extract may be spiked with a selected volume of a denatured ethanol prior to step 3 of adding and mixing the selected amine thereinto. A suitable volume of denatured ethanol may be selected from a range of about 2% to about 10% by volume of the standardized solvent-solubilized crude extract. Alternatively, the standardized solvent-solubilized crude extract may be spiked with a selected volume of acetone prior to adding and mixing the selected amine thereinto. A suitable volume of acetone may be selected from a range of about 4% to about 20% by volume of the standardized solvent-solubilized crude extract.

According to another aspect, a suitable second solvent for washing the recovered crude CBDA-amine salt in step 5, may be a C5-C7 alkane or a low b.p. petroleum ether. Particularly suitable alkanes may be heptane, hexane, and pentane.

According to another aspect, a suitable third organic solvent for resolubilizing the washed crude CBDA-amine salt in step 6, may be one of ethyl acetate, 85%-95% ethanol, denatured ethanol, methanol, isopropanol, dichloromethane, toluene, MTBE, THF, and the like. A particularly suitable solvent for resolubilizing the washed CBDA-amine salt in step 6, may be ethyl acetate heated to about 60° C.

According to another aspect, a suitable antisolvent for recrystallizing the solubilized CBDA-amine salt in step 7, may be an alkane such as one of heptane, hexane, pentane, and the like. In the case wherein an alcohol is the selected third organic solvent, a suitable antisolvent may be water.

According to another aspect, the recrystallized purified CBDA-amine salt may be decarboxylated in step 8, by adding the CBDA-amine salt into a sodium carbonate ($Na_2CO_3$) solution, then heating the mixture under constant mixing at a temperature selected from a range of about 90° C. to reflux for a period of time selected from a range of about 2 hr to about 18 hr, thereby producing an oil containing CBD and amine in the $Na_2CO_3$ solution. A suitable concentration of $Na_2CO_3$ solution to use for this step is from a range of about 1% to about 15% (w/v). A particularly suitable concentration of $Na_2CO_3$ solution is from a range of about 2.5% to about 10% (w/v), for example, about 5% (w/v). A particularly suitable temperature for this decarboxylation step is about 100° C. A particularly suitable time duration for this decarboxylation step is about 4 hr.

According to another aspect, the CBD can be solubilized and separated from the $Na_2CO_3$ solution in step 9, by the addition of an alkane to the $Na_2CO_3$ solution to dissolve the CBD and amine thereinto and to partition the mixture into an organic phase comprising an oil containing highly purified decarboxylated CBD and amine therein, and an aqueous phase comprising the $Na_2CO_3$ solution and residual contaminants separated from the decarboxylated CBD.

According to another aspect, a suitable fourth organic solvent for solubilizing thereinto the decarboxylated CBD and amine present in the organic phase may be a C5-C7 alkane such as heptane, hexane, and pentane.

According to another aspect, the amine may be separated from the CBD by acidification of the organic layer with a mineral acid, for example HCl, thereby producing an organic layer comprising highly purified CBD oil, and an aqueous layer containing the amine.

Another embodiment of the present disclosure pertains to an example method for preparing a crude extract from cannabis biomass, then separating out, recovering, and purifying CBDA from the crude extract prepared, then converting the purified CBDA into a purified CBD product. The example method comprises the steps of:
1. processing a cannabis biomass with a selected first organic solvent to produce a crude cannabis extract therefrom;
2. assaying the crude cannabis extract to determine the content of CBDA therein;

3a. if so desired, adding a selected second organic solvent to the crude cannabis extract to reduce the CBDA content therein to a level within a selected range in reference to a CBDA standard, thereby producing a standardized solvent-solubilized crude cannabis extract;

3b. if so desired, removing some of the first organic solvent from the solvent-solubilized crude cannabis extract to increase the CBDA content therein to a level within a selected range in reference to a CBDA standard, thereby producing a standardized solvent-solubilized crude cannabis extract;

4. adding and mixing into the standardized solvent-solubilized crude cannabis extract, a selected volume of a selected amine whereby the amine reacts with CBDA therein, thereby forming and precipitating a crude CBDA-amine salt;

5. Separating and recovering the precipitated crude CBDA-amine salt from the standardized solvent-solubilized crude cannabis extract;

6. washing the recovered crude CBDA-amine salt with the second organic solvent one or more times to thereby produce a washed crude CBDA-amine salt;

7 re-solubilizing the washed CBDA-amine salt in a selected third organic solvent;

8. crystalizing the solubilized CBDA-amine salt by the addition of and mixing with a selected antisolvent and then cooling to thereby produce a crystallized purified CBDA-amine salt;

9. decarboxylating the purified CBDA-amine salt to produce an oil containing CBD and amine;

10. solubilizing the oil comprising CBD and amine in a fourth selected organic solvent to thereby partition therefrom an organic layer containing the purified CBD oil and the amine, and an aqueous layer;

11. separating the organic layer containing the highly purified CBD and amine from the aqueous layer;

12. acidifying the organic layer with a mineral acid to partition therefrom an organic layer containing highly purified CBD, and an aqueous layer containing the amine as its hydrochloride salt;

13. separating the aqueous layer from the highly purified CBD; and 14. removing the fourth organic solvent from the highly purified CBD.

According to an aspect, a suitable first organic solvent for use in step 1 may be an alkane or a petroleum ether. Suitable alkanes include heptane, hexane, pentane, butane, their isomers, and the like. Particularly suitable alkanes are heptane, hexane, and pentane. It is optional if so desired, to concentrate the crude cannabis extract into an oil form and then adding a selected volume of the first organic solvent prior to assaying the crude cannabis extract in step 2.

According to another aspect, a suitable second organic solvent for use in steps 3 and/or 6 may be C5-C7 alkane or a petroleum ether. Particularly suitable alkanes may be heptane, hexane, and pentane.

According to another aspect, a suitable target range for adjusting the CBDA content to in step 3a or 3b may be from about 20 mg/ml to about 445 mg/ml. A particularly suitable target range may be from about 27 mg/ml to about 200 mg/ml. A preferred target range may be from about 31 mg/ml to about 153 mg/ml.

According to another aspect, a suitable amine for use in step 4 may be a tertiary amine such as diisopropylethylamine (Hunig's base), triethylamine, tripropylamine, tributylamine, methyldicyclohexylamine, quinine, and the like. Alternatively, a suitable amine may be a diamine such as N,N,N-trimethylethylenediamine, N,N,N,N-tetramethylethylenediamine, 4-aminomethylpiperidine, DABCO, DMAP, DBN, DBU, methylpiperazine, dimethylpiperazine, and the like. Alternatively, a suitable amine may be a secondary amine such as N-isopropylcyclohexylamine, diethylamine, 2,2,6,6-tetramethylpiperidine, and the like. Alternatively, a suitable amine may be an amino alcohol such as piperidineethanol, N,N-dimethylethanolamine, and the like. Alternatively, a suitable amine may be an amino ether such as morpholine, N-methylmorpholine, and the like. Alternatively, a suitable amine may be cyclohexylamine.

According to another aspect, the standardized solvent-solubilized crude cannabis extract may be spiked with a selected volume of denatured ethanol prior to adding and mixing the selected amine thereinto. A suitable volume of denatured ethanol may be selected from a range of about 2% to about 10% by volume of the standardized solvent-solubilized crude cannabis extract. Alternatively, the standardized solvent-solubilized crude extract may be spiked with a selected volume of acetone prior to adding and mixing the selected amine thereinto. A suitable volume of acetone may be selected from a range of about 4% to about 20% by volume of the standardized solvent-solubilized crude cannabis extract.

According to another aspect, a suitable third organic solvent for resolubilizing the washed crude CBDA-amine salt in step 7, may be one of ethyl acetate, 85%-95% ethanol, denatured ethanol, methanol, isopropanol, dichloromethane, toluene, MTBE, THF, and the like. A particularly suitable solvent for resolubilizing the washed crude CBDA-amine salt in step 7, may be ethyl acetate heated to about 60° C.

According to another aspect, a suitable antisolvent for recrystallizing the solubilized CBDA-amine salt in step 8, may be an alkane such as one of heptane, hexane, pentane, and the like. According to another aspect, distilled water may be a suitable antisolvent if an alcohol has been used as the third organic solvent.

According to another aspect, the recrystallized purified CBDA-amine salt may be decarboxylated in step 9, by adding the CBDA-amine salt into a $Na_2CO_3$ solution, then heating the mixture under constant mixing at a temperature selected from a range of about 90° C. to reflux for a period of time selected from a range of about 2 hr to about 18 hr, thereby producing an oil comprising decarboxylated CBD and amine in the $Na_2CO_3$ solution. A suitable concentration of $Na_2CO_3$ solution to use for this step is from a range of about 1% to about 15% (w/v). A particularly suitable concentration of $Na_2CO_3$ solution is from a range of about 2.5% to about 10% (w/v), for example, about 5% (w/v). A particularly suitable temperature for this decarboxylation step is about 100° C. A particularly suitable time duration for this decarboxylation step is about 4 hr.

According to another aspect, the decarboxylated CBD may be converted into a highly purified CBD by acidification of the decarboxylated CBD organic layer with a mineral acid to thereby produce an organic layer containing highly purified CBD, and an aqueous layer containing the amine as its hydrochloride. Suitable mineral acids may be HCl or $H_2SO_4$.

Another embodiment of the present disclosure pertains to an example method for separating out, recovering, and purifying CBDA in the form of a CBDA-amine salt, from a crude extract comprising a mixture of cannabinoids and cannabis phytochemicals recovered from processing cannabis biomass, and then separating and recovering therefrom a highly purified CBDA from the CBDA-amine salt. The example method comprises the steps of:
1. assaying a crude cannabis extract to determine the concentration of THCA therein.
2. adding to and commingling a first organic solvent with the crude cannabis extract to reduce the CBDA content therein to a level within a selected target range in reference to a CBDA standard, thereby producing a standardized solvent-solubilized crude cannabis extract;
3. adding and mixing into the standardized solvent-solubilized crude cannabis extract, a selected volume of a selected amine whereby the ammonium moiety of the amine reacts with CBDA therein, thereby forming and precipitating a crude CBDA-amine salt;
4. separating and recovering the precipitated crude CBDA-amine salt from the standardized solvent-solubilized crude extract;
5. washing the recovered crude CBDA-amine salt with a selected second organic solvent one or more times to thereby produce a washed CBDA-amine salt;
6. re-solubilizing the washed CBDA-amine salt in a selected third organic solvent;
7. crystalizing the solubilized CBDA-amine salt by cooling and optionally, by the addition of and mixing with a selected antisolvent, to thereby produce a crystallized purified CBDA-amine salt;
8. re-solubilizing the purified CBDA-amine salt in the third organic solvent;
9. acidifying the solubilized purified CBDA-amine salt with a mineral acid to partition therefrom an organic layer containing the highly purified CBDA, and an aqueous layer containing the amine;
12. separating the aqueous layer from the organic layer containing the highly purified CBDA; and
13a. concentrating the highly purified CBDA by volatilization of the fourth organic solvent therefrom to thereby produce highly purified CBDA; or alternatively
13b. placing the CBDA under a negative pressure to reduce traces of remaining solvent thereby producing highly purified CBDA.

According to an aspect, a suitable first organic solvent for use in step 2 may be a C5-C7 hydrocarbon such as an alkane or a low b.p. petroleum ether. Particularly suitable alkanes include such as heptane, hexane, pentane, their isomers, and the like. It is optional if so desired, to solubilize the crude cannabis extract in a selected volume of the first organic solvent prior to assaying the crude cannabis extract in step 1.

According to another aspect, a suitable amine for use in step 3 may be a tertiary amine such as diisopropylethylamine (Hunig's base), triethylamine, tripropylamine, tributylamine, methyldicyclohexylamine, quinine, and the like. Alternatively, a suitable amine may be a diamine such as N,N,N-trimethylethylenediamine, N,N,N,N-tetramethylethylenediamine, 4-aminomethylpiperidine, DABCO, DMAP, DBN, DBU, dimethylpiperazine, and the like. Alternatively, a suitable amine may be a secondary amine such as N-isopropylcyclohexylamine, diethylamine, 2,2,6,6-tertamethylpiperidine, and the like. Alternatively, a suitable amine may be an amino alcohol such as piperidineethanol, N,N-dimethylethanolamine, and the like. Alternatively, a suitable amine may be an amino ether such as morpholine, N-methylmorpholine, and the like. Alternatively, a suitable amine may be cyclohexylamine.

According to another aspect, the standardized solvent-solubilized crude extract may be spiked with a selected volume of denatured alcohol prior to step 3 of adding and mixing the selected amine thereinto. A suitable volume of denatured alcohol may be selected from a range of about 2% to about 10% by volume of the standardized solvent-solubilized crude extract. Alternatively, the standardized solvent-solubilized crude extract may be spiked with a selected volume of acetone prior to adding and mixing the selected amine thereinto. A suitable volume of acetone may be selected from a range of about 4% to about 20% by volume of the standardized solvent-solubilized crude extract.

According to another aspect, a suitable second solvent for washing the recovered crude CBDA-amine salt in step 5, may be a C5-C7 hydrocarbon solvent such as an alkane or a petroleum ether. Suitable alkanes include heptane, hexane, pentane, their isomers, and the like. Particularly suitable alkanes are heptane and hexane.

According to another aspect, a suitable third solvent for resolubilizing the washed CBDA-amine salt in step 6, may be one of ethyl acetate, 85%-95% ethanol, denatured ethanol, methanol, isopropanol, dichloromethane, toluene, MTBE, THF, and the like. A particularly suitable solvent for resolubilizing the washed CBDA-amine salt in step 7, may be ethyl acetate heated to about 60° C.

According to another aspect, a suitable antisolvent for recrystallizing the solubilized CBDA salt in step 7, may be an alkane such as one of heptane, hexane, pentane, and the like. Alternatively, if an alcohol has been used as the third organic solvent, a suitable antisolvent may be distilled water.

Other embodiments of the present disclosure relate to purified CBDA-amine salts that have been precipitated and recovered from solvent-solubilized crude cannabis extracts with an amine selected from one of triethylamine, methyldicyclohexylamine, tributylamine, N,N,N-trimethylethylenediamine, N,N,N,N-tetramethylethylenediamine, 4-aminomethylpiperidine, DABCO, DMAP, DBN, DBU, dimethylpiperazine, diisopropylethylamine (Hunig's base), N-isopropylcyclohexylamine, N-isopropylcyclohexylamine, 2,2,6,6-tetramethylpiperidine, piperidineethanol and N,N-dimethylethanolamine, morpholine, N-methylmorpholine, cyclohexylamine, and the like. An example method for producing purified CBDA-amine salts comprises the steps of:
1. providing a crude extract comprising a mixture of cannabinoids and cannabis phytochemicals recovered from cannabis biomass;
2. assaying the crude extract to determine the content of CBDA therein;
3. adding a selected volume of a first organic solvent to crude extract to thereby adjust the CBDA content therein to within a selected range in reference to a CBDA standard, thereby producing a standardized solvent-solubilized crude extract;
4. adding and mixing into the standardized solvent-solubilized crude extract, a selected volume of a selected amine whereby the ammonium moiety of the amine reacts with CBDA therein, thereby forming and precipitating a crude CBDA-amine salt;
5. separating and recovering the precipitated crude CBDA-amine salt from the standardized solvent-solubilized crude extract;
6. washing the recovered crude CBDA-amine salt with a selected second organic solvent one or more times to thereby produce a washed CBDA-amine salt;
7 re-solubilizing the washed CBDA-amine salt in a selected third organic solvent;
8 crystalizing the solubilized CBDA-amine salt by cooling and optionally, by the addition of and mixing with a selected antisolvent, to thereby produce a crystallized purified CBDA-amine salt;
9. separating, recovering, and washing the recrystallized purified CBDA-amine salt with the second organic solvent, then drying the purified CBDA-amine salt.

According to an aspect, a suitable first organic solvent for use in step 2 may be a C5-C7 hydrocarbon such as an alkane or a low b.p. petroleum ether. Particularly suitable alkanes include such as heptane, hexane, pentane, their isomers, and the like.

According to another aspect, a suitable second solvent for washing the recovered crude CBDA-amine salt in step 6, may be a C5-C7 hydrocarbon solvent such as an alkane or a petroleum ether. Suitable alkanes include heptane, hexane, pentane, their isomers, and the like. Particularly suitable alkanes are heptane and hexane.

According to another aspect, a suitable third solvent for resolubilizing the washed CBDA-amine salt in step 7, may be one of ethyl acetate, 85%-95% ethanol, denatured ethanol, methanol, isopropanol, dichloromethane, toluene, MTBE, THF, and the like. A particularly suitable solvent for resolubilizing the washed CBDA-amine salt in step 7, may be ethyl acetate heated to about 60° C.

According to another aspect, a suitable antisolvent for recrystallizing the solubilized CBDA salt in step 7, may be an alkane such as one of heptane, hexane, pentane, and the like.

According to an aspect, triethylamine (tertiary amine) may be added to and commingled with a solvent-solubilized crude cannabis extract to precipitate therefrom a CBDA-amine salt having a chemical structure shown in (1):

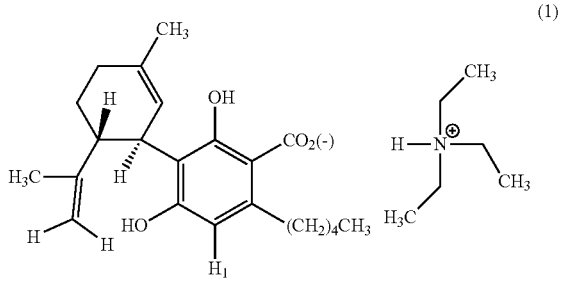

(1)

The precipitated CBDA-triethylamine salt may be washed with a selected organic solvent, optionally recrystallized, and then dried to thereby produce a purified CBDA-triethylamine salt.

According to an aspect, N-methylmorpholine (amino ester) may be added to and commingled with a solvent-solubilized crude cannabis extract to precipitate therefrom a CBDA-amine salt having a chemical structure shown in (2):

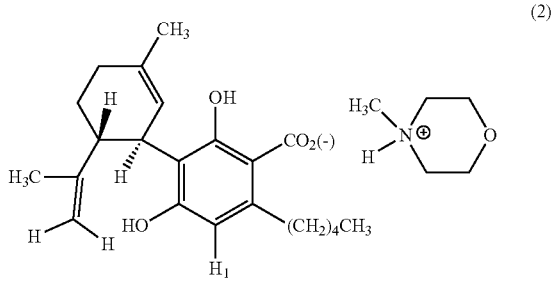

(2)

The precipitated CBDA-N-methylmorpholine salt may be washed with a selected organic solvent, optionally recrystallized, and then dried to thereby produce a purified CBDA-N-methylmorpholine salt.

According to an aspect, 1,8-diazabicycloundec-7-ene (DBU) may be added to and commingled with a solvent-solubilized crude cannabis extract to precipitate therefrom a CBDA-amine salt having a chemical structure shown in (3):

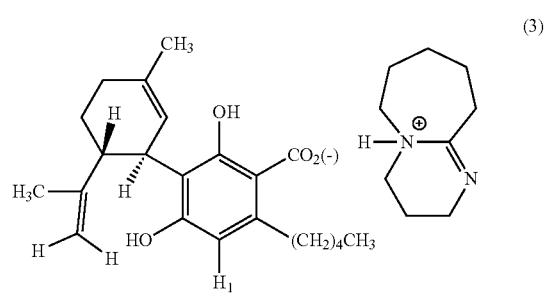

(3)

The precipitated CBDA-DBU salt may be washed with a selected organic solvent, optionally recrystallized, and then dried to thereby produce a purified CBDA-DBU salt.

According to an aspect, piperidineethanol (amino alcohol) may be added to and commingled with a solvent-solubilized crude cannabis extract to precipitate therefrom a CBDA-amine salt having a chemical structure shown in (4):

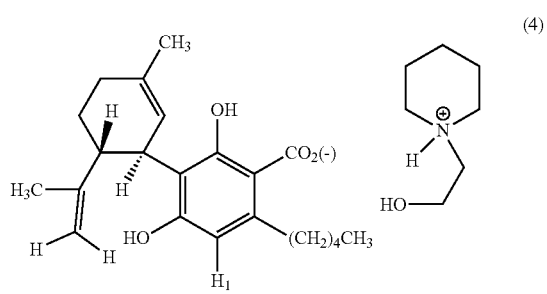

(4)

The precipitated CBDA-piperidineethanol salt may be washed with a selected organic solvent, optionally recrystallized, and then dried to thereby produce a purified CBDA-piperidineethanol salt.

According to an aspect, 4-dimethylaminopyridine (DMAP) (diamine) may be added to and commingled with a solvent-solubilized crude cannabis extract to precipitate therefrom a CBDA-amine salt having a chemical structure shown in (5):

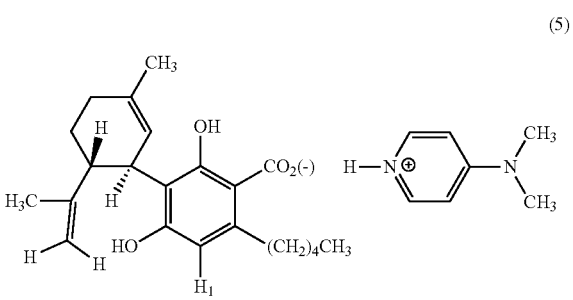

(5)

The precipitated CBDA-DMAP salt may be washed with a selected organic solvent, optionally recrystallized, and then dried to thereby produce a purified CBDA-DMAP salt.

According to an aspect, cyclohexylamine (primary amine) may be added to and commingled with a solvent-solubilized crude cannabis extract to precipitate therefrom a CBDA-amine salt having a chemical structure shown in (6):

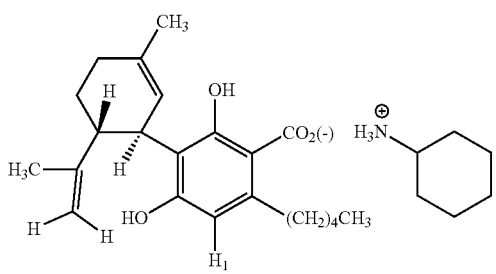

(6)

The precipitated CBDA-cyclohexylamine salt may be washed with a selected organic solvent, optionally recrystallized, and then dried to thereby produce a purified CBDA-cyclohexylamine salt.

According to an aspect, 1,5-diazabicyclooctane (DABCO) (diamine) may be added to and commingled with a solvent-solubilized crude cannabis extract to precipitate therefrom a CBDA-amine salt having a chemical structure shown in (7):

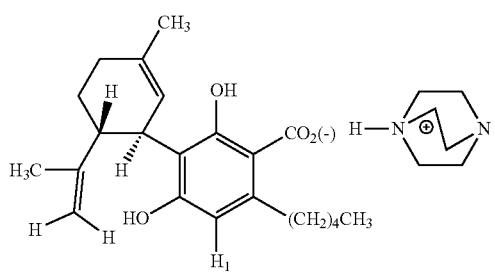

(7)

The precipitated CBDA-DABCO salt may be washed with a selected organic solvent, optionally recrystallized, and then dried to thereby produce a purified CBDA-DABCO salt.

According to an aspect, methyldicyclohexylamine (tertiary amine) may be added to and commingled with a solvent-solubilized crude cannabis extract to precipitate therefrom a CBDA-amine salt having a chemical structure shown in (8):

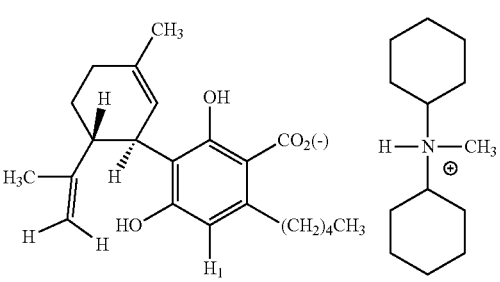

(8)

The precipitated CBDA-methyldicyclohexylamine salt may be washed with a selected organic solvent, optionally recrystallized, and then dried to thereby produce a purified CBDA-methyldicyclohexylamine salt.

According to an aspect, N,N,N,N-tetramethylethylenediamine (TMEDA) (diamine) may be added to and commingled with a solvent-solubilized crude cannabis extract to precipitate therefrom a CBDA-amine salt having a chemical structure shown in (9):

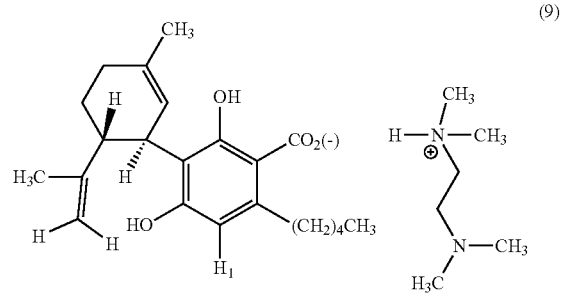

(9)

The precipitated CBDA-TMEDA salt may be washed with a selected organic solvent, optionally recrystallized, and then dried to thereby produce a purified CBDA-TMEDA salt.

According to an aspect, diisopropylethylamine (tertiary amine) may be added to and commingled with a solvent-solubilized crude cannabis extract to precipitate therefrom a CBDA-amine salt having a chemical structure shown in (10):

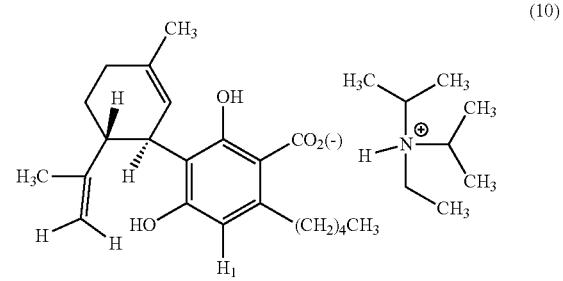

(10)

The precipitated CBDA-diisopropylethylamine salt may be washed with a selected organic solvent, optionally recrystallized, and then dried to thereby produce a purified CBDA-diisopropylethylamine salt.

According to an aspect, N-isopropylcyclohexylamine (secondary amine) may be added to and commingled with a solvent-solubilized crude cannabis extract to precipitate therefrom a CBDA-amine salt having a chemical structure shown in (11):

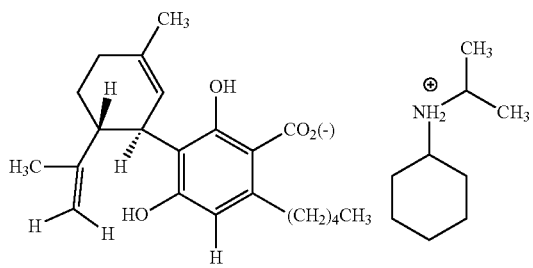

(11)

The precipitated CBDA-N-isopropylcyclohexylamine salt may be washed with a selected organic solvent, optionally recrystallized, and then dried to thereby produce a purified CBDA-N-isopropylcyclohexylamine salt.

According to an aspect, tributylamine (tertiary amine) may be added to and commingled with a solvent-solubilized crude cannabis extract to precipitate therefrom a CBDA-amine salt having a chemical structure shown in (12):

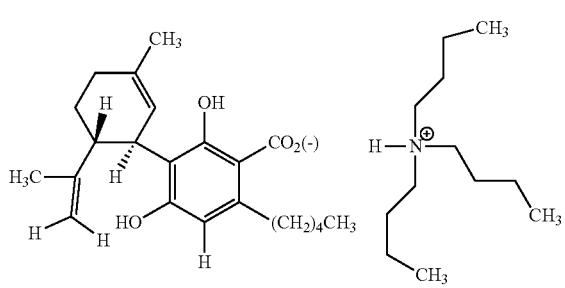

(12)

The precipitated CBDA-tributylamine salt may be washed with a selected organic solvent, optionally recrystallized, and then dried to thereby produce a purified CBDA-tributylamine salt.

According to an aspect, dimethylpiperazine (diamine) may be added to and commingled with a solvent-solubilized crude cannabis extract to precipitate therefrom a CBDA-amine salt having a chemical structure shown in (13):

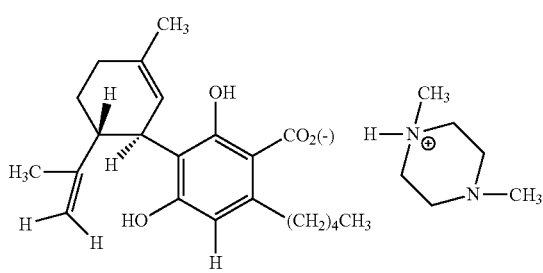

(13)

The precipitated CBDA-dimethylpiperazine salt may be washed with a selected organic solvent, optionally recrystallized, and then dried to thereby produce a purified CBDA-dimethylpiperazine salt.

According to an aspect, N,N,N-trimethylethylenediamine (diamine) may be added to and commingled with a solvent-solubilized crude cannabis extract to precipitate therefrom a CBDA-amine salt having a chemical structure shown in (14):

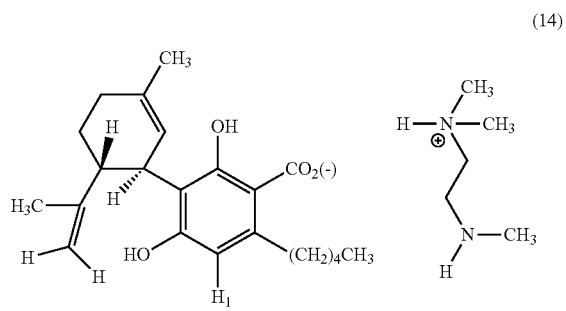

(14)

The precipitated CBDA-N,N,N-trimethylethylenediamine salt may be washed with a selected organic solvent, optionally recrystallized, and then dried to thereby produce a purified CBDA-N,N,N-trimethylethylenediamine salt.

According to an aspect, 2,2,6,6-tetramethylpiperidine (secondary amine) may be added to and commingled with a solvent-solubilized crude cannabis extract to precipitate therefrom a CBDA-amine salt having a chemical structure shown in (15):

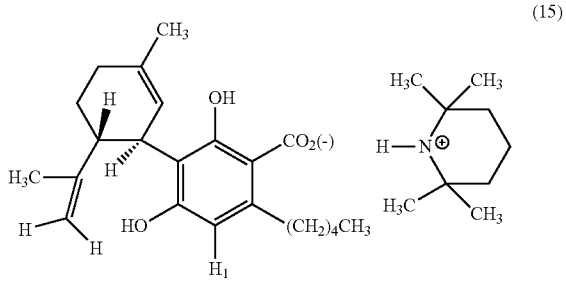

(15)

The precipitated CBDA-2,2,6,6-tetramethylpiperidine salt may be washed with a selected organic solvent, optionally recrystallized, and then dried to thereby produce a purified CBDA-2,2,6,6-tetramethylpiperidine salt.

According to an aspect, morpholine (amino ester) may be added to and commingled with a solvent-solubilized crude cannabis extract to precipitate therefrom a CBDA-amine salt having a chemical structure shown in (16):

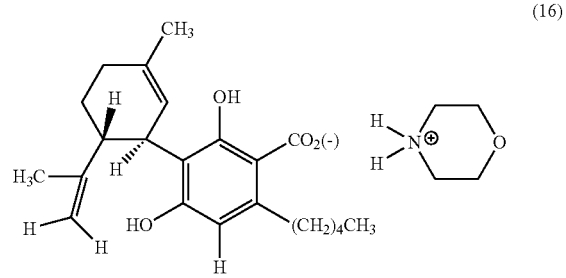

(16)

The precipitated CBDA-morpholine salt may be washed with a selected organic solvent, optionally recrystallized, and then dried to thereby produce a purified CBDA-morpholine salt.

According to an aspect, N,N-dimethylethanolamine (amino alcohol) may be added to and commingled with a solvent-solubilized crude cannabis extract to precipitate therefrom a CBDA-amine salt having a chemical structure shown in (17):

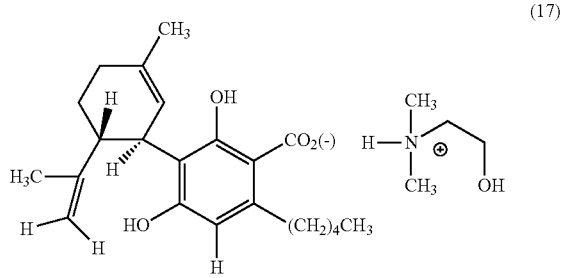
(17)

The precipitated CBDA-dimethylethanolamine salt may be washed with a selected organic solvent, optionally recrystallized, and then dried to thereby produce a purified CBDA-dimethylethanolamine salt.

According to an aspect, quinine (tertiary amine) may be added to and commingled with a solvent-solubilized crude cannabis extract to precipitate therefrom a CBDA-amine salt having a chemical structure shown in (18):

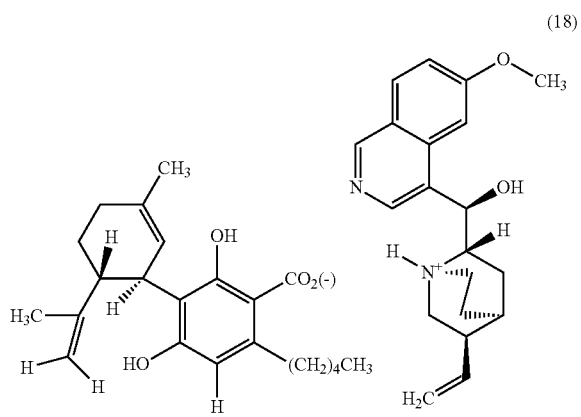
(18)

The precipitated CBDA-quinine salt may be washed with a selected organic solvent, optionally recrystallized, and then dried to thereby produce a purified CBDA-quinine salt.

According to an aspect, diethylamine (secondary amine) may be added to and commingled with a solvent-solubilized crude cannabis extract to precipitate therefrom a CBDA-amine salt having a chemical structure shown in (19):

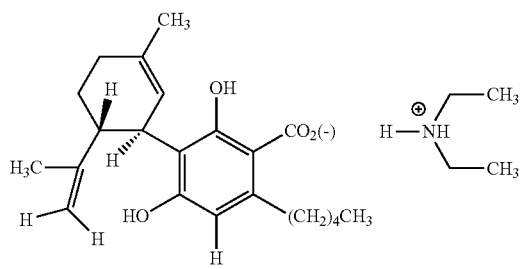
(19)

The precipitated CBDA-diethylamine salt may be washed with a selected organic solvent, optionally recrystallized, and then dried to thereby produce a purified CBDA-diethylamine salt.

According to an aspect, tripropylamine (tertiary amine) may be added to and commingled with a solvent-solubilized crude cannabis extract to precipitate therefrom a CBDA-amine salt having a chemical structure shown in (20):

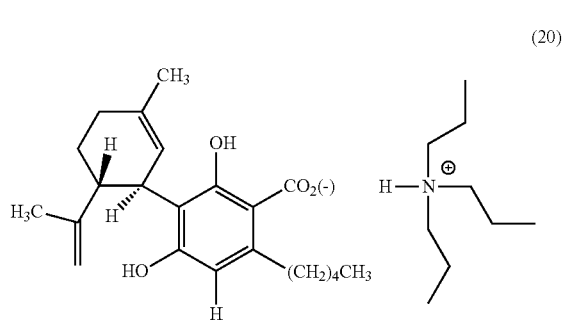
(20)

The precipitated CBDA-tripropylamine salt may be washed with a selected organic solvent, optionally recrystallized, and then dried to thereby produce a purified CBDA-tripropylamine salt.

The following examples are provided to more fully describe the invention and are presented for non-limiting illustrative purposes.

EXAMPLES

Example 1

Figure 1B:
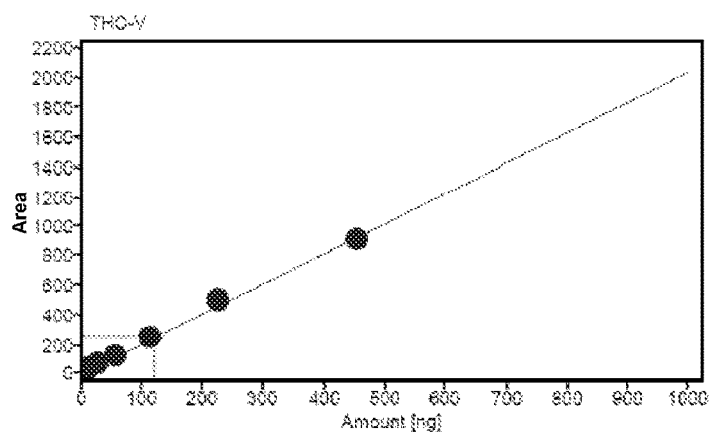
FIG. 1B is a chart showing a linear calibration curve for tetrahydrocannbidivarin (THCV)
Figure 1C:
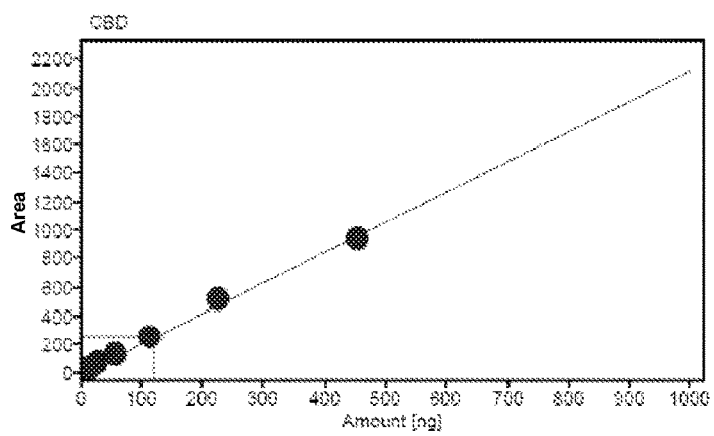
FIG. 1C is a chart showing a linear calibration curve for cannabidiol (CBD)
Figure 2A:
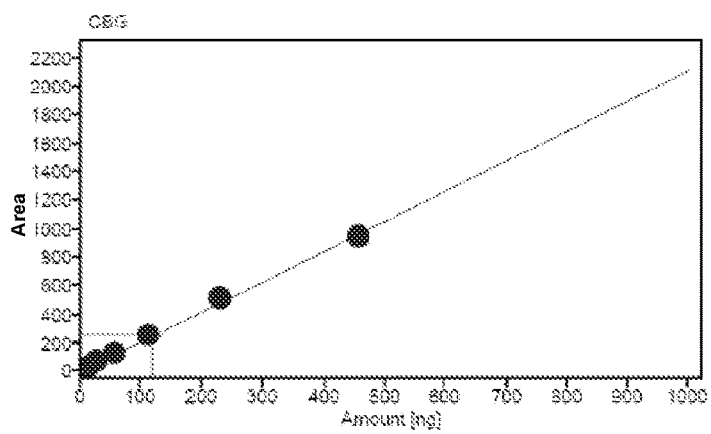
FIG. 2A is a chart showing a linear calibration curve for cannabigerol (CBG)
Figure 2B:
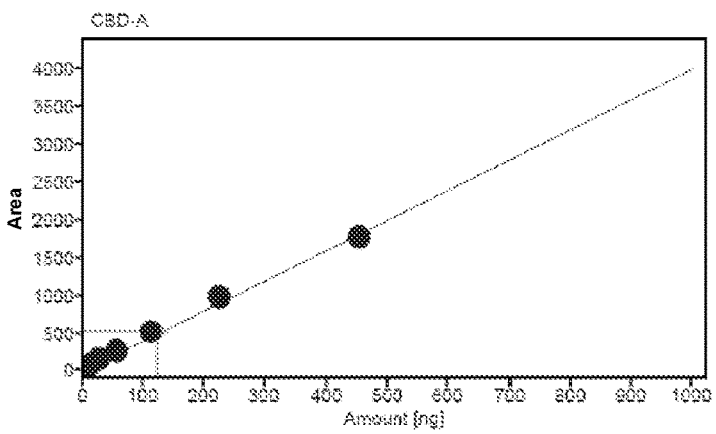
FIG. 2B is a chart showing a linear calibration curve for cannabidiolic acid (CBDA)
Figure 2C:
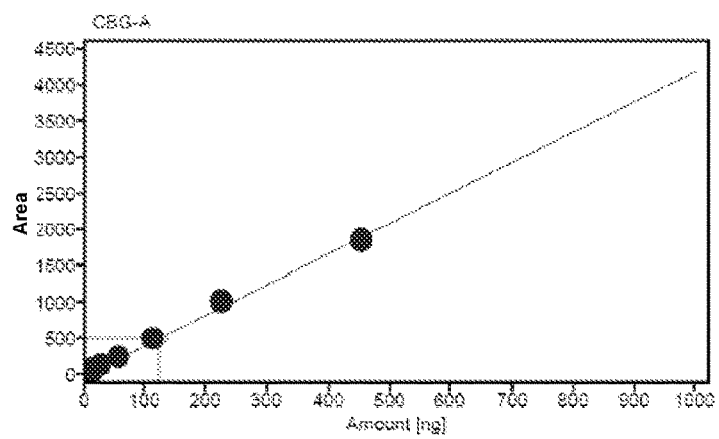
FIG. 2C is a chart showing a linear calibration curve for cannabigerolic acid (CBGA)
Figure 3A:
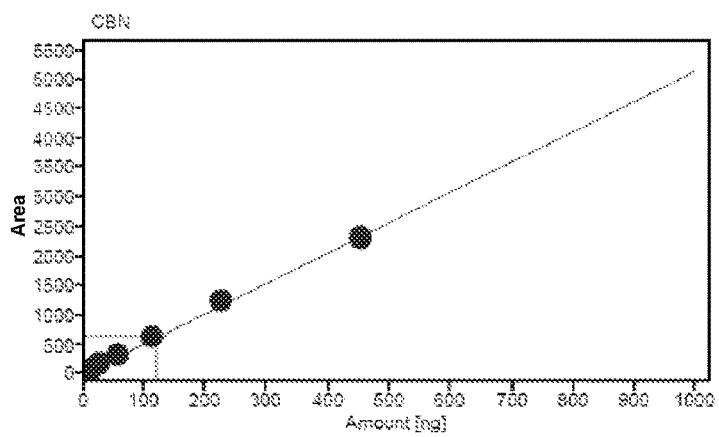
FIG. 3A is a chart showing a linear calibration curve for cannabinol (CBN)
Figure 3B:
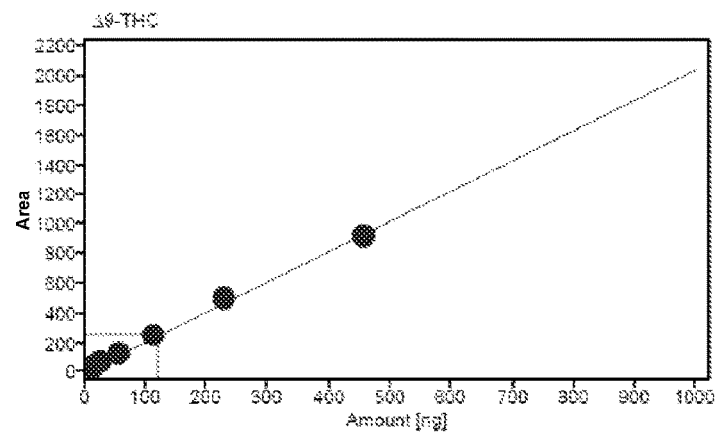
FIG. 3B is a chart showing a linear calibration curve for $\Delta^9$-tetrahydrocannabinol THC)
Figure 3C:
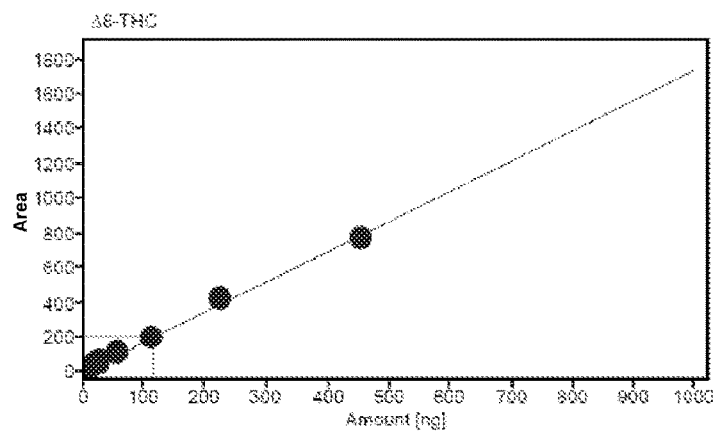
FIG. 3C is a chart showing a linear calibration curve for $\Delta^8$-tetrahydrocannabinol THC)
Figure 4A:
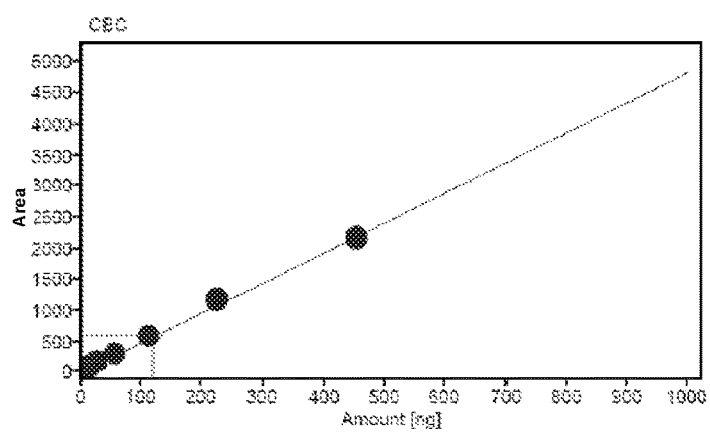
FIG. 4A is a chart showing a linear calibration curve for cannabichromene (CBC)
Figure 4B:
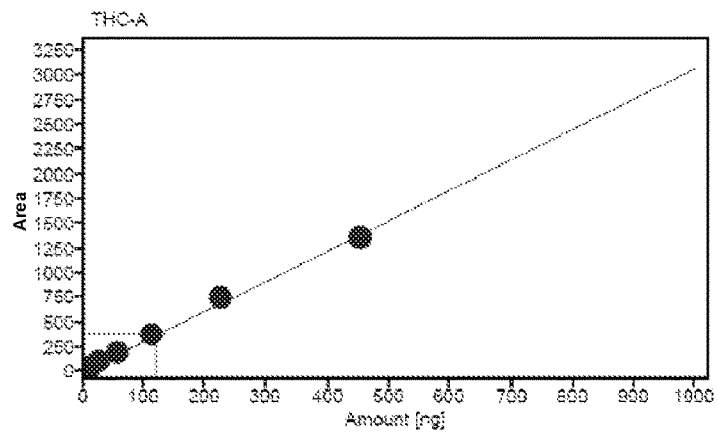
FIG. 4B is a chart showing a linear calibration curve for (−)-Trans-$\Delta^9$-tetrahydrocannabinolic acid (THCA)
Figure 5:
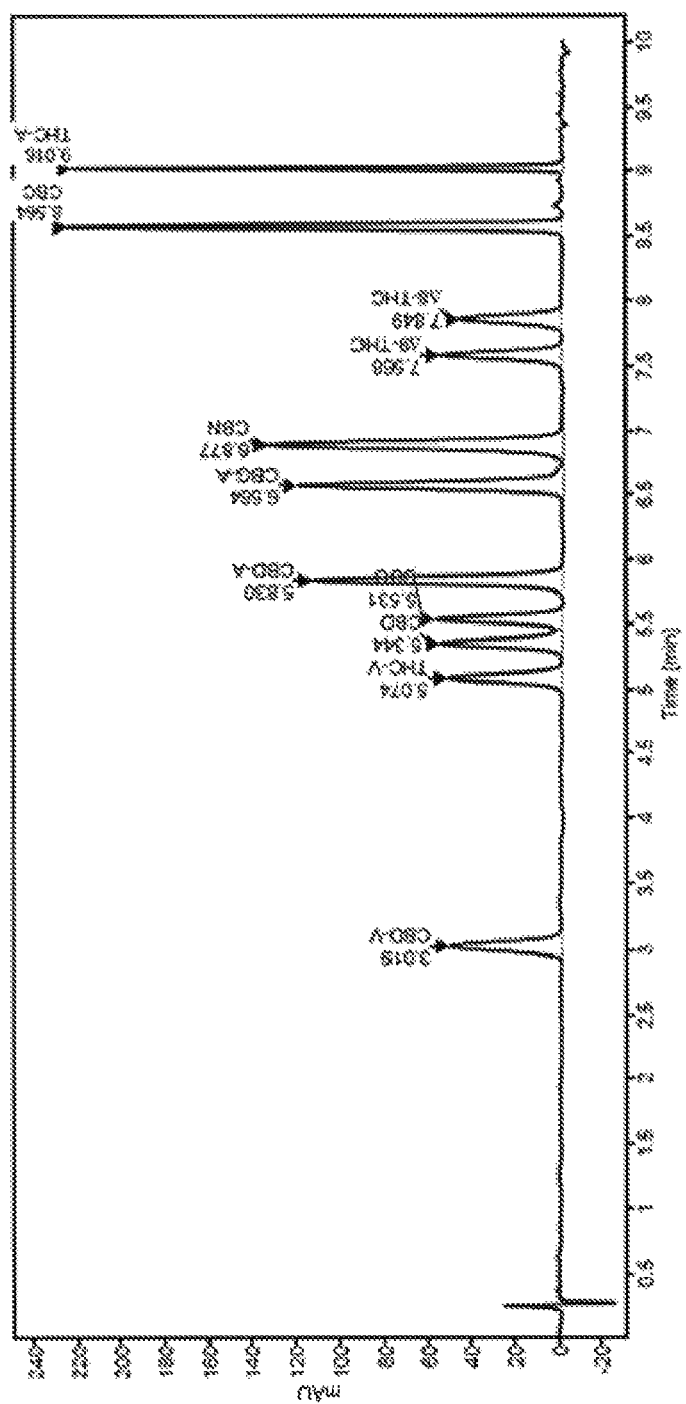
FIG. 5 is an HPLC chromatogram showing separation of a standardized reference mixture of the eleven cannabinoid phytochemicals shown in FIGS. 1A-4B.

Prior to assessing and refining the methods disclosed herein, an internal method for detecting and quantifying individual THC and CBD phytochemicals based on use of HPLC methods and equipment, was developed and tested for sensitivity, precision, and reproducibility. Eleven naturally occurring purified cannabinoid phytochemical compounds were purchased from Mandel Scientific Inc. (Guelph, ON, CA). Specifically, cannabidivarin (CBDV), tetrahydrocannbidivarin (THCV), cannabidiol (CBD), cannabigerol (CBG), cannabidiolic acid (CBDA), cannabigerolic acid (CBGA), cannabinol (CBN), (−)-trans-$\Delta^9$-tetrahydrocannabinol ($\Delta^9$-THC), cannabichromene (CBC), $\Delta^8$-tetrahydrocannabinolic acid ($\Delta^8$-THCA). Seven dilutions (1.42 µg/ml, 2.84 µg/ml, 5.68 µg/ml, 11.36 µg/ml, 22.73 µg/ml, 45.45 µg/ml, 90.90 µg/ml) of each cannabinoid standard were prepared and analyzed in triplicate following the instructions in the Agilent Application Note "Dedicated Cannabinoid Potency Testing Using the Agilent 1220 Infinity II LC System" (downloaded from world wide web address: agilent.com/chem). The average of the three measurements for each of the seven dilutions was used to create a linear calibration curve for each of the eleven cannabinoid phytochemical compounds: FIG. 1A, CBDV; FIG. 1B, THCV; FIG. 1C, CBD; FIG. 2A, CBG; FIG. 2B, CBD-A; FIG. 2C, CBGA; FIG. 3A, CBN, FIG. 3B, $\Delta^9$-TH C; FIG. 3C, $\Delta^8$-TH C; FIG. 4A, CBC; FIG. 4B, THCA. A mixture containing 22.73 µg/mL of each of the eleven above-noted cannabinoid phytochemical compounds was prepared and then analyzed with the Agilent 1220 Infinity II LC System. The HPLC analysis of the mixture is shown in FIG. 5 and summarized below in Table 1.

TABLE 1

| Name | RT | Peak Area % | Amount [ng] | Concentration [µg/mL] |
|---|---|---|---|---|
| CBD-V | 3.019 | 6.49 | 114.983 | 22.9965 |
| THC-V | 5.074 | 6.13 | 121.932 | 24.3865 |
| CBD | 5.344 | 6.34 | 121.629 | 24.3257 |
| CBG | 5.531 | 6.24 | 120.126 | 24.0252 |
| CBD-A | 5.830 | 12.32 | 125.316 | 25.0633 |
| CBG-A | 6.564 | 12.75 | 123.143 | 24.6285 |
| CBN | 6.877 | 15.31 | 120.991 | 24.1982 |
| Δ9-THC | 7.568 | 6.12 | 121.963 | 24.3925 |
| Δ8-THC | 7.849 | 5.05 | 118.237 | 23.6473 |
| CBC | 8.564 | 14.13 | 119.110 | 23.8221 |
| THC-A | 9.016 | 9.10 | 120.688 | 24.1376 |

Example 2

Figure 6A:
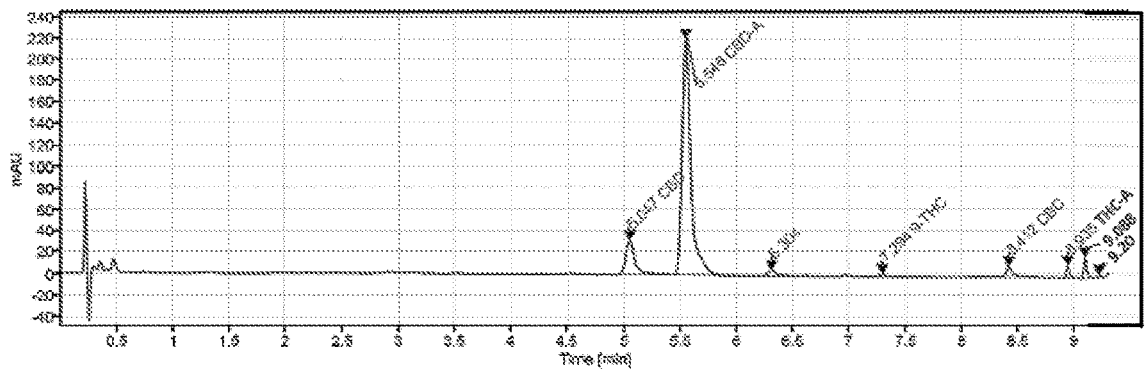
FIG. 6A is an HPLC chromatogram showing separation of cannabinoids from a crude hemp biomass extract in Example 2.

A sample of a high-CBD-content hemp biomass was assayed for its cannabinoid phytochemical composition with an Agilent 1220 II Infinity LC Gradient UV/DAD High-Pressure Liquid Chromatography System (HPLC) in reference to the standards mixture analysis shown in Example 1. The cannabinoid phytochemical contents of the hemp biomass included CBD (11.92%), CBDA (78.89%), $\Delta^9$-THC (1.68%), CBC (0.64%), and THCA (2.81%) (FIG. 6A; Table 2).

Figure 6B:
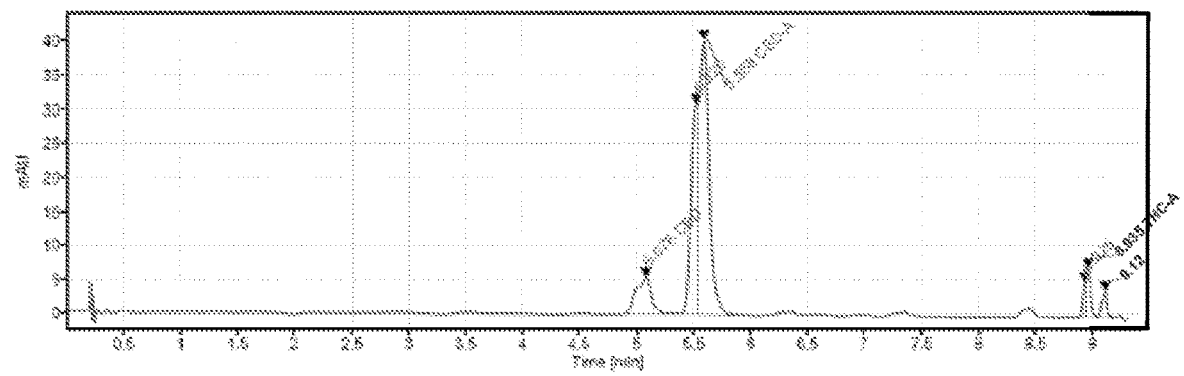
FIG. 6B is an HPLC chromatogram showing the composition of a standardized solvent-solubilized crude hemp extract prepared from the crude hemp biomass extract shown in FIG. 6A.

Then, 5.0 kilograms of the high-CBD hemp biomass were extracted using butane as the extraction solvent to produce a viscous resinous extract. The resinous extract was analyzed with the Agilent HPLC system in reference to the standards mixture analysis shown in Example 1. The cannabinoid phytochemical contents of the crude extract included CBD (10.99%), CBDA (54.19%), and THCA (3.79%) (FIG. 6B; Table 3).

TABLE 2

| Name | RT [min] | RF | Area | Amount [ng] | Concentration [ug/ml] | Peak Area Percent |
|---|---|---|---|---|---|---|
| CBD | 5.05 | 2.105 | 180.780 | 85.899 | 17.180 | 11.92 |
| CBD-A | 5.55 | 5.405 | 1196.164 | 221.298 | 44.260 | 78.89 |
| 9-THC | 7.29 | 2.091 | 9.638 | 4.610 | 0.922 | 1.68 |
| CBC | 8.41 | 9.784 | 42.578 | 4.352 | 0.870 | 0.64 |
| THC-A | 8.93 | 3.971 | 22.520 | 5.671 | 1.134 | 2.81 |

TABLE 3

| Name | RT [min] | RF | Area | Amount [ng] | Concentration [ug/ml] | Peak Area Percent |
|---|---|---|---|---|---|---|
| CBD | 5.08 | 2.000 | 50.696 | 25.345 | 25.345 | 10.99 |
| CBD-A | 5.59 | 4.661 | 249.976 | 53.627 | 53.627 | 54.19 |
| THC-A | 8.96 | 4.730 | 17.491 | 3.698 | 3.698 | 3.79 |

Figure 6C:
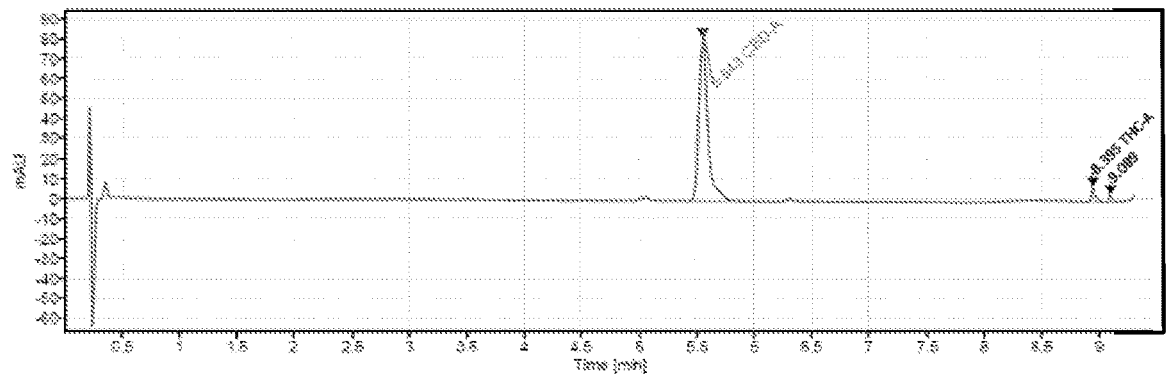
FIG. 6C is an HPLC chromatogram showing a washed crude CBD-triethylamine salt precipitated from the crude hemp extract shown in FIG. 6B.

The hemp crude extract was dissolved in heptane after which, a triethylamine solution was added dropwise to the crude extract heptane solution to precipitate therefrom a crude isolate comprising cannabinoid phytochemical compounds. The crude isolate was then analyzed with the Agilent HPLC system. The cannabinoid phytochemical contents of the crude isolate showed two peaks identified as CBDA (95.3% of the total cannabinoids) and as THCA (3.6%) (FIG. 6C Table 4).

TABLE 4

| Name | RT [min] | RF | Area | Amount [ng] | Concentration [ug/ml] | Peak Area Percent |
|---|---|---|---|---|---|---|
| CBD-A | 5.54 | 5.395 | 443.460 | 82.192 | 16.438 | 95.28 |
| THC-A | 8.94 | 3.780 | 16.508 | 4.367 | 0.873 | 3.55 |

Figure 6D:
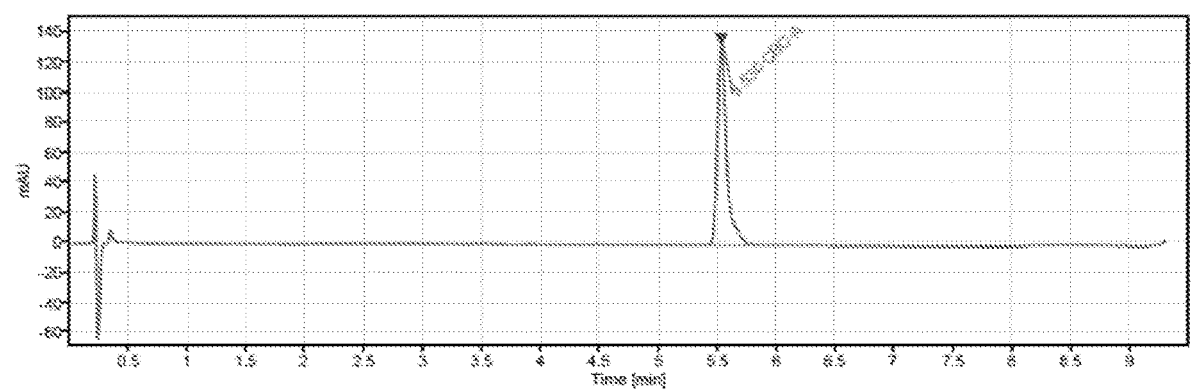
FIG. 6D is an HPLC chromatogram showing the composition of a purified CBDA salt recovered from the crude CBD-triethylamine salt shown in FIG. 6C.

The precipitated crude isolate was then washed with an ethyl acetate solution, filtered by vacuum filtration, and dried to form a purified cannabinoid precipitate. A sample of the purified cannabinoid precipitate was analyzed with the Agilent HPLC system. FIG. 6D and Table 5 show that its content was purified CBDA.

TABLE 5

| Name | RT [min] | RF | Area | Amount [ng] | Concentration [ug/ml] | Peak Area Percent |
|---|---|---|---|---|---|---|
| CBD-A | 5.53 | 5.402 | 735 787 | 136.217 | 27.243 | 100.00 |

Figure 6E:
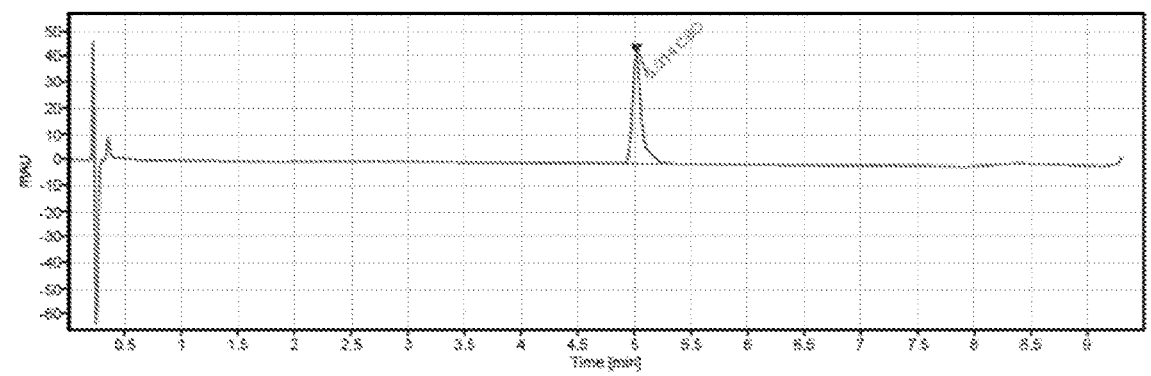
FIG. 6E is an HPLC chromatogram showing the composition of a decarboxylated CBD oil recovered from the purified CBDA salt shown in FIG. 6D.

The purified cannabinoid precipitate was then mixed with a 2.5% solution of $Na_2CO_3$ and decarboxylated under controlled heating at about 100° C.±3° C. for four hours to produce a viscous oil. A sample of the viscous oil was analyzed with the Agilent HPLC system. FIG. 6E and Table 6 show its content was purified CBD.

TABLE 6

| Name | RT [min] | RF | Area | Amount [ng] | Concentration [ug/ml] | Peak Area Percent |
|---|---|---|---|---|---|---|
| CBD | 5.01 | 2.111 | 239.383 | 113.414 | 22.683 | 100.00 |

Example 3

Figure 7A:
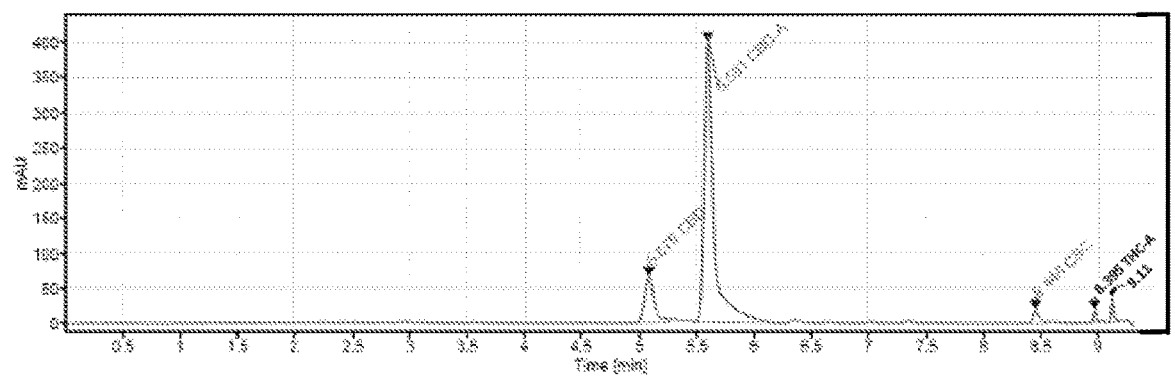
FIG. 7A is an HPLC chromatogram showing separation of cannabinoid phytochemicals from a hemp plant biomass sample in Example 3.

58.868 g of a high-CBD-content hemp biomass sample were extracted with 350 ml of heptane to produce a solubilized cannabis extract solution. The heptane solvent was removed by rotary evaporator to produce 8.32 grams of a viscous resin. The resin was solubilized in 83 ml of heptane to produce a 1:10 mass/volume standardized solvent-solubilized hemp extract solution. A sample of the hemp extract solution was diluted 300 times and analyzed with the Agilent HPLC system. FIG. 7A and Table 7 show that the cannabinoids CBD, CBDA, CBC and THCA were identified and confirmed by UV Spectra in the diluted sample extract solution and contained 88.826 µg/ml of CBDA. The 10:1 standardized extract solution was calculated to contain 2211.535 mg of CBDA.

TABLE 7

| Name | RT [min] | RF | Area | Amount [ng] | Concentration [ug/ml] | Peak Area Percent |
|---|---|---|---|---|---|---|
| CBD | 5.08 | 2.118 | 386.979 | 182.715 | 36.543 | 13.12 |
| CBD-A | 5.59 | 5.408 | 2401.918 | 444.131 | 88.826 | 81.43 |
| CBC | 8.45 | 8.163 | 63.900 | 7.828 | 1.566 | 2.17 |
| THC-A | 8.96 | 4.198 | 36.869 | 8.782 | 1.756 | 1.25 |

Figure 7B:
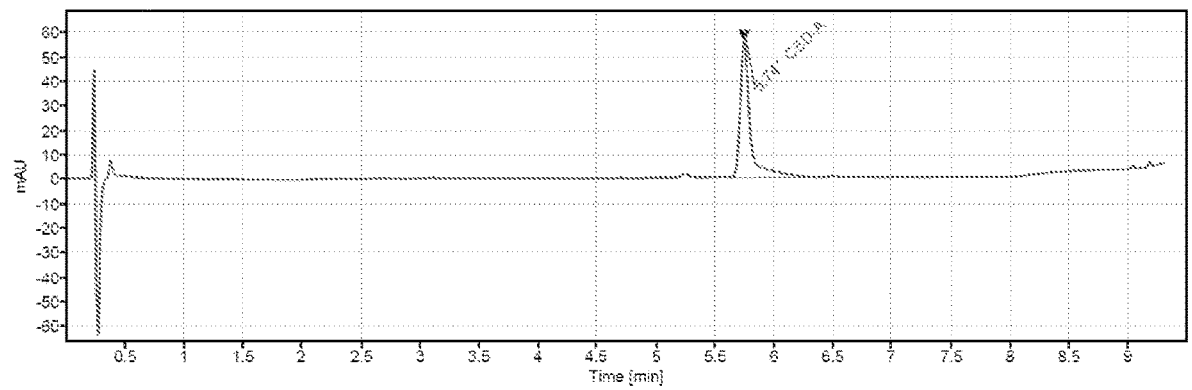
FIG. 7B is an HPLC chromatogram showing separation of a cannabinoid phytochemical isolate from a crude extract recovered from the hemp plant biomass sample shown in FIG. 7A.

A 3:1 molar ratio (amine/CBDA) of a triethylamine solution (1.872 g) was added to the standardized solvent-solubilized hemp extract solution while mixing thereby precipitating 4.712 g of a crude CBDA-triethylamine salt precipitate. The crude CBDA-triethylamine salt was separated from the liquid phase by pressure filtration and dried under nitrogen. A sample of the crude CBDA-triethylamine salt was solubilized in methanol and analyzed with the Agilent HPLC system. The cannabinoid phytochemical contents of the crude isolate showed one peak identified by UV Spectra as 100% pure CBDA (FIG. 7B; Table 8).

TABLE 8

| Name | RT [min] | RF | Area | Amount [ng] | Concentration [ug/ml] | Peak Area Percent |
|---|---|---|---|---|---|---|
| CBD-A | 5.74 | 5.390 | 335.247 | 62.194 | 12.439 | 100.00 |

Figure 7C:
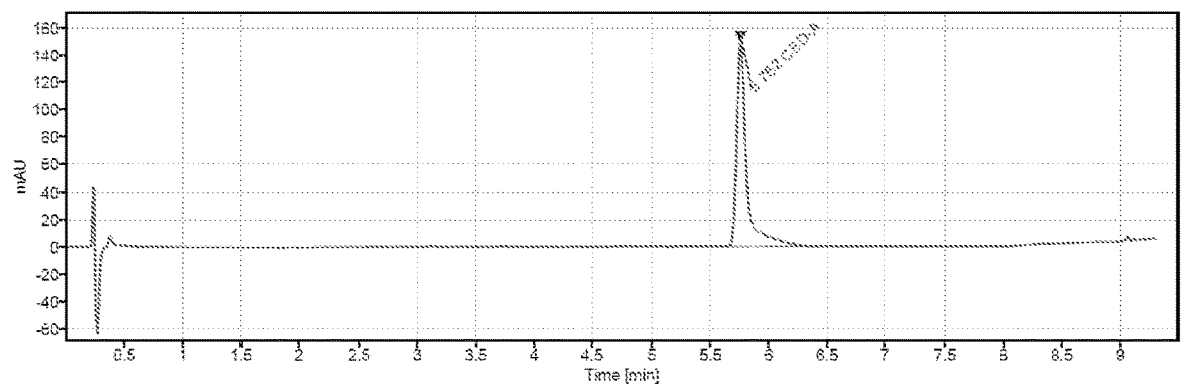
FIG. 7C is an HPLC chromatogram showing a purified cannabinoid phytochemical compound from the phytochemical isolate illustrated in FIG. 7B.

4.6923 g of the crude CBDA precipitate was then washed with 48 ml of ethyl acetate and filtered by vacuum filtration and dried to produce 3.2022 g of a white purified CBDA precipitate. A sample of the purified CBDA precipitate was solubilized in methanol and analyzed with the Agilent HPLC system. The cannabinoid phytochemical contents of the purified CBDA precipitate showed one peak identified by UV Spectra as CBDA (FIG. 7C; Table 9).

TABLE 9

| Name | RT [min] | RF | Area | Amount [ng] | Concentration [ug/ml] | Peak Area Percent |
|---|---|---|---|---|---|---|
| CBD-A | 5.75 | 5.403 | 890.035 | 164.723 | 32.945 | 100.00 |

Figure 7D:
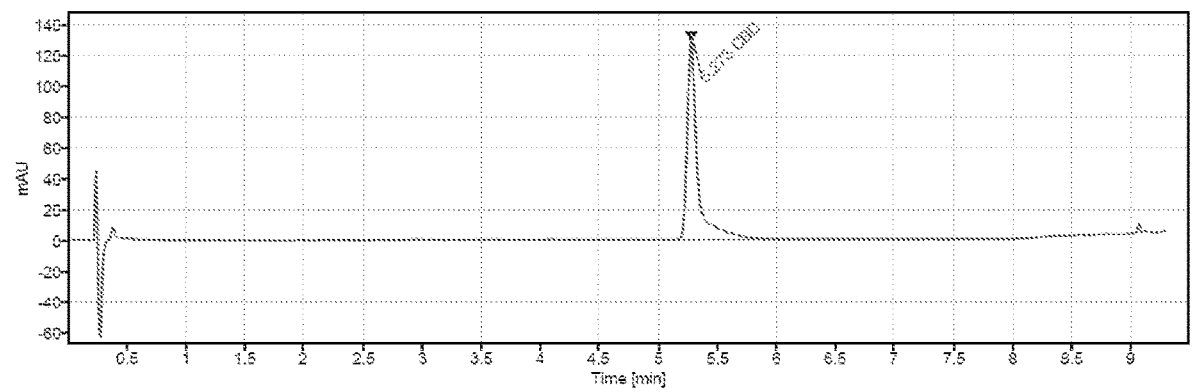
FIG. 7D is an HPLC chromatogram showing a decarboxylated purified cannabinoid phytochemical compound derived from the purified cannabinoid phytochemical compound illustrated in FIG. 7C.

3.2022 g of the white CBDA precipitate was added to 100 ml of a 2.5% $Na_2CO_3$ solution and heated at about 100° C.±3° C. for 4 hours to produce therein a partitioned two-phase solution of an upper oil layer containing decarboxylated CBD and a lower aqueous layer containing the $Na_2CO_3$ solution. 30 ml of heptane was added into and mixed with the upper oil layer to dissolve thereinto the CBD. The lower aqueous layer was separated from the organic layer after which, the heptane was removed from the organic layer by rotary evaporation to thereby produce 2.076 g of a viscous oil. A sample of the viscous oil was solubilized in methanol and analyzed with the Agilent HPLC system. The HPLC analysis showed one peak identified by UV Spectra as decarboxylated CBD (FIG. 7D; Table 10).

TABLE 10

| Name | RT [min] | RF | Area | Amount [ng] | Concentration [ug/ml] | Peak Area Percent |
|---|---|---|---|---|---|---|
| CBD | 5.27 | 2.124 | 791.187 | 372.502 | 74.500 | 100.00 |

Example 4

Figure 8A:
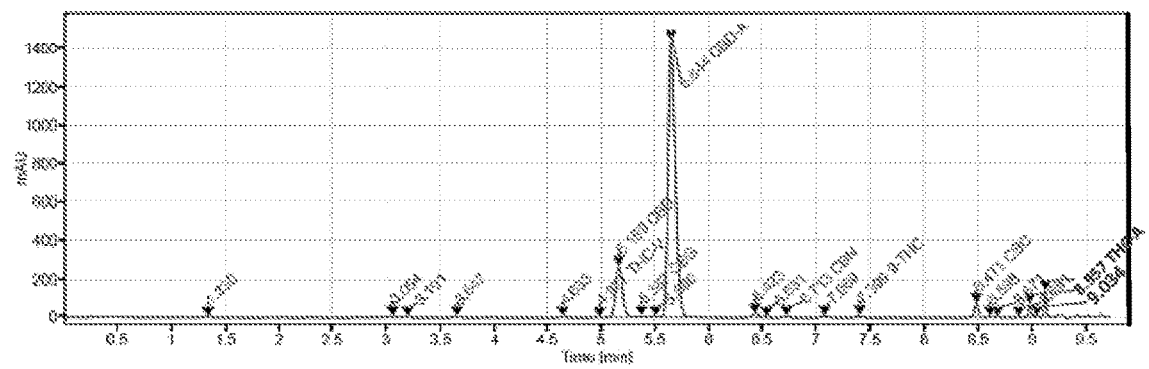
FIG. 8A is an HPLC chromatogram showing separation of cannabinoid phytochemicals from a standardized solvent-solubilized crude hemp extract in Example 4.

99.345 g of a high-CBD-content hemp biomass sample was extracted with 600 ml of heptane to produce a solubilized cannabis extract solution. The heptane solvent was removed by rotary evaporator to produce 14.195 g of a viscous resin. The resin was solubilized in 142 ml of heptane to produce a 1:10 mass/volume standardized extract solution. A sample of the standardized extract solution was diluted to a 100 times final dilution and was analyzed with the Agilent HPLC system. FIG. 8A and Table 11 show that the cannabinoids THCV, CBD, CBD, and CBDA were identified and confirmed by UV Spectra in the diluted standardized extract solution and contained 145.841 µg/ml of CBDA. The 10:1 standardized extract solution was calculated to contain 4447.156 mg of CBDA.

TABLE 11

| Name | RT [min] | RF | Area | Amount [ng] | Concentration [ug/ml] | Peak Area Percent |
|---|---|---|---|---|---|---|
| THC-V | 4.98 | 2.023 | 13.024 | 6.437 | 1.287 | 0.15 |
| CBD | 5.16 | 1.656 | 1207.774 | 729.205 | 145.841 | 13.56 |
| CBG | 5.37 | 1.837 | 32.010 | 17.422 | 3.484 | 0.36 |
| CBD-A | 5.64 | 4.283 | 6707.345 | 1565.902 | 313.180 | 75.33 |

Figure 8B:
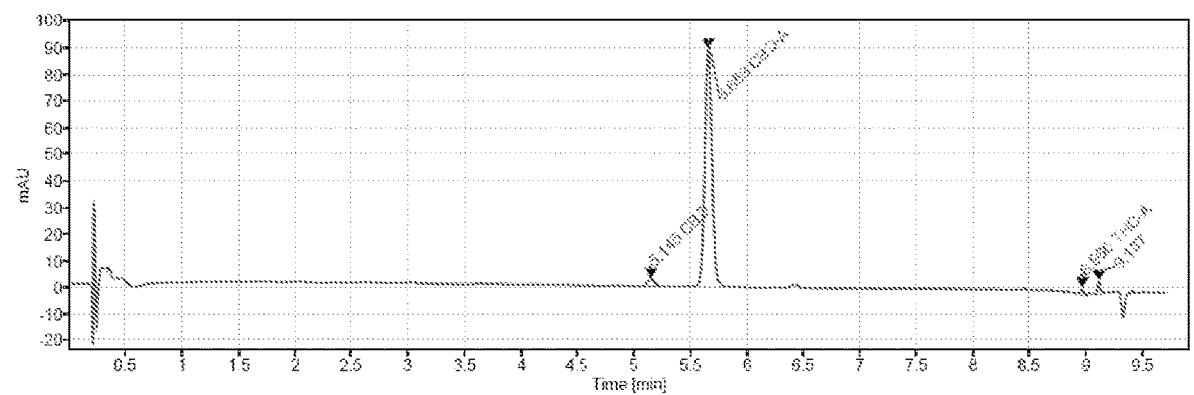
FIG. 8B is an HPLC chromatogram showing the cannabinoid phytochemical content of a crude CBDA-triethylamine salt precipitated from the crude hemp extract sample shown in FIG. 8A.

A 3:1 molar ratio (amine/CBDA) of a triethylamine solution (5.178 ml containing $3.723 \times 10^{-2}$ moles) was added to the standardized solvent-solubilized hemp extract solution while mixing thereby precipitating 8.641 g of a crude CBDA-triethylamine salt. The crude CBDA-triethylamine salt was separated from the liquid phase by pressure filtration and dried under nitrogen. A sample of the crude CBDA-triethylamine salt was solubilized in methanol and analyzed with the Agilent HPLC system. The cannabinoid phytochemical contents of the crude CBDA-triethylamine salt identified the presence of small amounts of CBD (2.88%), THCA (1.14%), and 94.15% CBDA (FIG. 8B; Table 12).

TABLE 12

| Name | RT [min] | RF | Area | Amount [ng] | Concentration [ug/ml] | Peak Area Percent |
|---|---|---|---|---|---|---|
| CBD | 5.15 | 1.715 | 12.080 | 7.045 | 1.409 | 2.88 |
| CBD-A | 5.65 | 4.284 | 394.746 | 92.152 | 18.430 | 94.15 |
| THC-A | 8.96 | 3.011 | 4.785 | 1.589 | 0.318 | 1.14 |

Figure 8C:
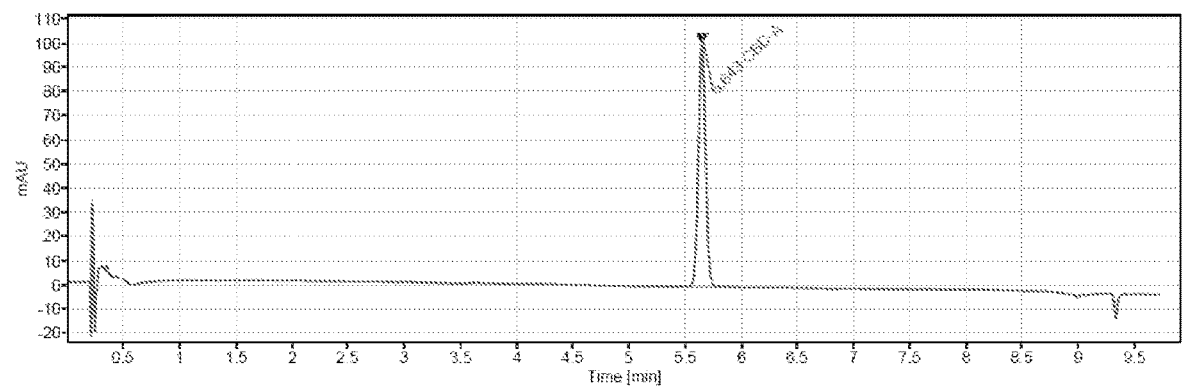
FIG. 8C is an HPLC chromatogram showing the composition of a purified CBDA salt recovered from the crude CBDA-triethylamine salt shown in FIG. 8B.

The crude CBDA-triethylamine salt was washed by slurrying in ethyl acetate warmed to 40° C. at a 6:1 volume/mass ratio. The washed CBDA salt was recovered by vacuum filtration and then dried completely. The dried CBDA salt was resuspended and washed in heptane, then recovered by vacuum filtration and dried completely to produce a purified CBDA salt (FIG. 8C, Table 13).

TABLE 13

| Name | RT [min] | RF | Area | Amount [ng] | Concentration [ug/ml] | Peak Area Percent |
|---|---|---|---|---|---|---|
| CBD-A | 5.64 | 4.284 | 443.712 | 103.583 | 20.717 | 100.00 |

Figure 8D:
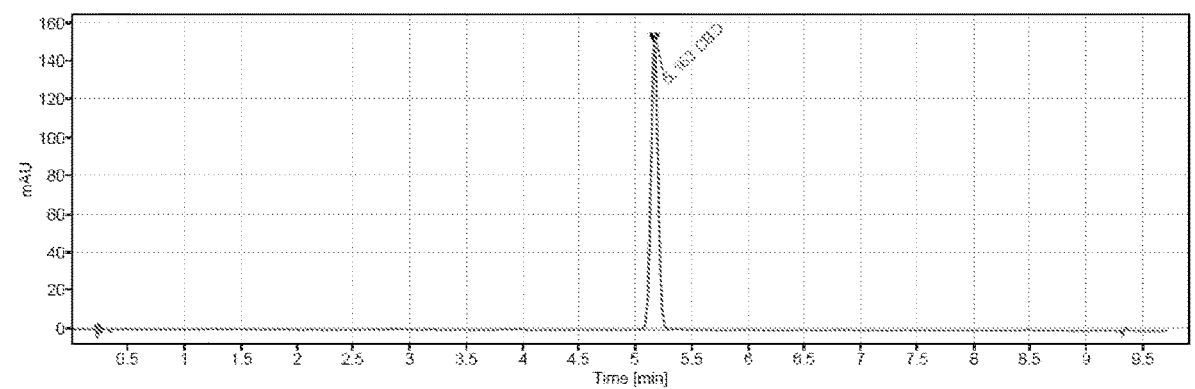
FIG. 8D is an HPLC chromatogram showing the composition of a decarboxylated CBD oil recovered from the purified CBDA salt shown in FIG. 8C.

1.985 g of the purified CBDA salt was added into a 2.5% $Na_2CO_3$ solution in a 10:1 volume/mass ratio, and then heated at 100° C.±3° C. for 4 hours to thereby produce therein a partitioned two-phase solution of an upper oil layer containing decarboxylated CBD and a lower aqueous layer containing the Na₂CO₃ solution. 30 ml of heptane were added into and mixed with the upper oil layer to dissolve thereinto the CBD. The lower aqueous layer was separated from the organic layer after which, the heptane was removed from the organic layer by rotary evaporation to thereby produce 4.040 g of a viscous oil. A sample of the viscous oil was solubilized in methanol and analyzed with the Agilent HPLC system. The HPLC analysis showed one peak identified by UV Spectra as 100% pure CBD (FIG. 8D; Table 14).

TABLE 14

| Name | RT [min] | RF | Area | Amount [ng] | Concentration [ug/ml] | Peak Area Percent |
|---|---|---|---|---|---|---|
| CBD | 5.16 | 1.657 | 674.124 | 406.898 | 81.380 | 100.00 |

Example 5

Figure 9A:
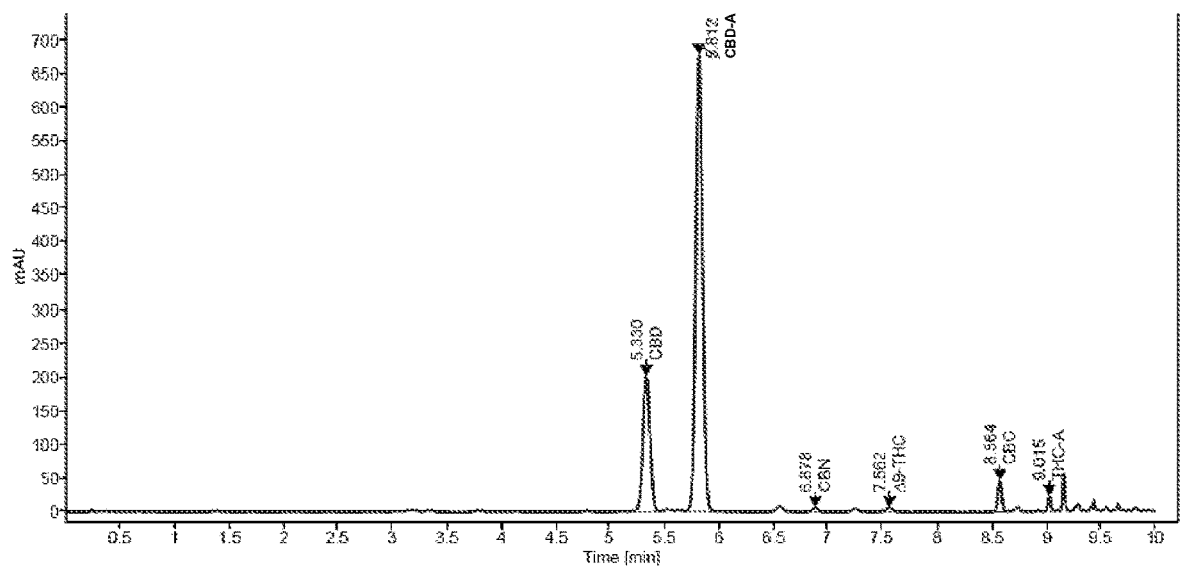
FIG. 9A is an HPLC chromatogram showing separation of cannabinoid phytochemicals from a standardized solvent-solubilized crude hemp extract in Example 5.

154.404 g of a high-CBD-content hemp biomass sample was extracted with 926 ml of heptane to produce a crude cannabis extract solution. The heptane solvent was removed by rotary evaporator to thereby produce 21.044 g of a viscous resin. The resin was solubilized in 210 ml of heptane to produce a 1:10 mass/volume standardized solvent-solubilized crude hemp extract. A sample of the standardized solvent-solubilized crude hemp extract was analyzed with the Agilent HPLC system. FIG. 9A and Table 15 show that the cannabinoids CBD, CBDA, CBN, CBC, THCA and Δ9-THC were identified and confirmed by UV Spectra in the diluted standardized extract solution and contained 156.527 µg/ml of CBDA. The 10:1 standardized extract solution was calculated to contain 8212.648 mg of CBDA.

TABLE 15

| Name | RT | Peak Area % | Amount [ng] | Concentration [µg/mL] |
|---|---|---|---|---|
| CBD | 5.330 | 21.28 | 570.067 | 114.0133 |
| CBD-A | 5.812 | 69.47 | 782.635 | 156.5270 |
| CBN | 6.878 | 0.68 | 6.483 | 1.2966 |
| Δ9-THC | 7.562 | 0.80 | 18.824 | 3.7649 |
| CBC | 8.564 | 2.83 | 26.404 | 5.2808 |
| THC-A | 9.015 | 0.93 | 12.597 | 2.5193 |

Figure 9B:
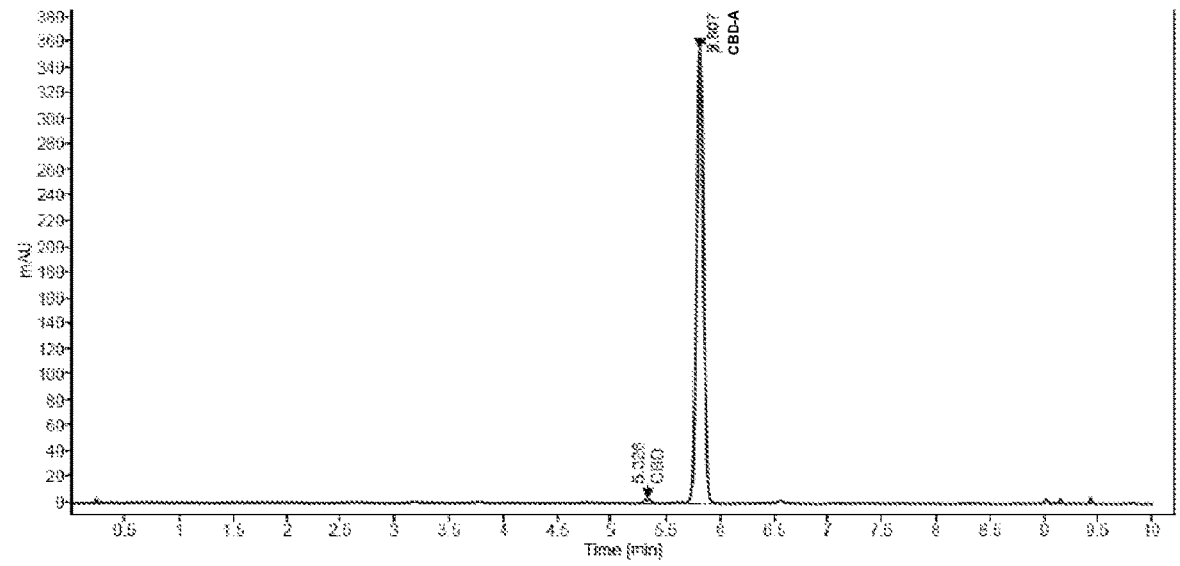
FIG. 9B is an HPLC chromatogram showing the cannabinoid phytochemical content of a crude CBDA-triethylamine salt precipitated from the crude hemp extract sample shown in FIG. 9A.

21 ml of denatured ethanol were added to the standardized extract solution to produce a 1:10 volume/volume denatured ethanol-spiked standardized solvent-solubilized crude hemp extract. Triethylamine was added to the spiked standardized solvent-solubilized crude hemp extract in a 3:1 molar ratio of triethylamine/CBDA while stirring, and thereby precipitated 9.547 g of a crude CBDA-triethylamine salt. The crude CBDA-triethylamine salt was separated from the liquid phase by pressure filtration and dried under nitrogen to produce 9.547 g of crude CBDA-triethylamine salt. A sample of the was analyzed by HPLC and the data in FIG. 9B and Table 16 indicate that the crude CBDA-triethylamine salt contained 97.75% CBDA-triethylamine salt and 1.01% CBD.

TABLE 16

| Name | RT | Peak Area % | Amount [ng] | Concentration [µg/mL] |
|---|---|---|---|---|
| CBD | 5.326 | 1.01 | 10.137 | 2.0275 |
| CBD-A | 5.807 | 97.75 | 411.145 | 82.2290 |

Figure 9C:
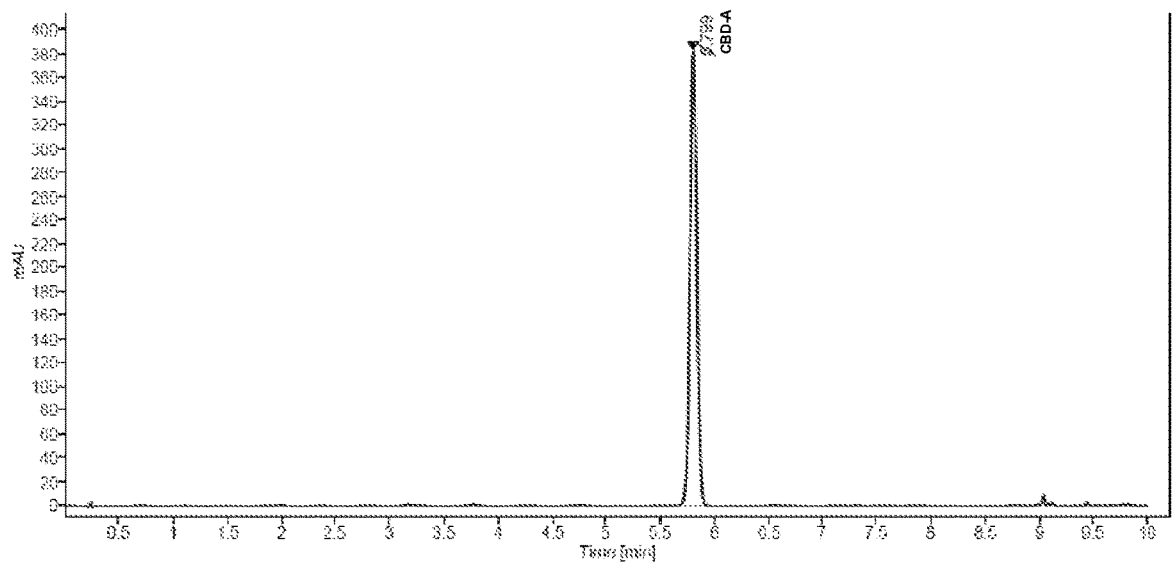
FIG. 9C is an HPLC chromatogram showing the composition of a purified CBDA-triethylamine salt recovered from the crude CBDA-triethylamine salt shown in FIG. 9B.

A 10:1 volume/mass mixture of ethyl acetate was mixed with 1.5% heptane (v/v) and then heated to about 63° C. Then, the crude CBDA-triethylamine salt was dissolved in the ethyl acetate/heptane mixture after which, the CBDA was recrystallized by cooling the mixture to 30° C., and then storing the cooled mixture at 4° C. for about 16 hr. The recrystallized purified CBDA-triethylamine salt was recovered from the liquid phase by vacuum filtration and then was washed it a 3:1 mass/volume of cold heptane (4° C.). The washed purified CBDA-triethylamine salt was recovered by vacuum filtration and dried to completeness to produce 6.895 g of dried purified CBDA-triethylamine salt. A sample of the purified CBDA-triethylamine salt was solubilized in methanol and analyzed with the Agilent HPLC system. The data in FIG. 9C and Table 17 indicate that the purity of the purified CBDA-triethylamine salt was 100%.

TABLE 17

| Name | RT | Peak Area % | Amount [ng] | Concentration [µg/mL] |
|---|---|---|---|---|
| CBD-A | 5.799 | 100.00 | 445.263 | 89.0526 |

Figure 9D:
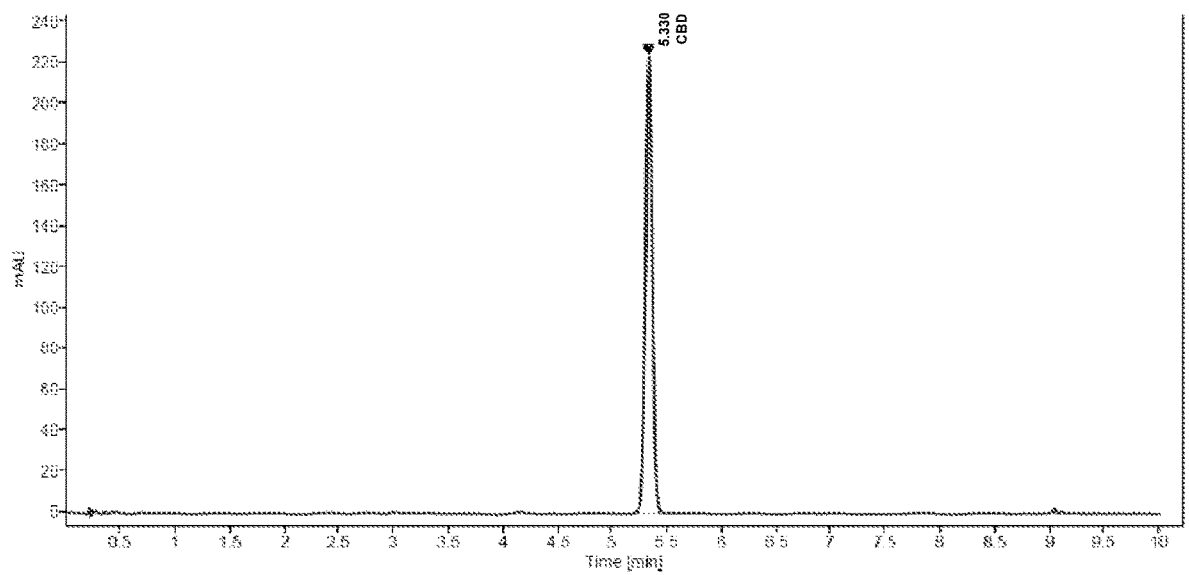
FIG. 9D is an HPLC chromatogram showing the composition of a decarboxylated CBD oil recovered from the purified CBDA-triethylamine salt shown in FIG. 9C.

The dried purified CBDA-triethylamine salt was added to 70 ml of a 2.5% Na₂CO₃ solution and heated under refluxing conditions at about 100° C.±3° C. for 4 hours to produce therein a partitioned two-phase solution of an upper oil layer containing decarboxylated CBD and triethylamine, and a lower aqueous layer. 40 ml of heptane were added and mixed with the partitioned layers to dissolve thereinto the decarboxylated CBD and triethylamine. After removal of the lower aqueous layer, 40 ml of 5% HCl solution was added to the remaining organic layer and well mixed thereby partitioning the mixture into an organic later containing the decarboxylated CBD and aqueous layer containing the triethylamine. After removal of the aqueous layer, heptane was removed from the organic layer by distillation thereby producing 4.625 g of highly purified CBD oil that solidified upon standing (FIG. 9D, Table 18).

TABLE 18

| Name | RT | Peak Area % | Amount [ng] | Concentration [µg/mL] |
|---|---|---|---|---|
| CBD | 5.330 | 100.00 | 625.565 | 125.1131 |

Example 6

A study was performed to assess the potential of forty selected amine compounds from a range of amines, for reliable and routine precipitation of CBD from complex mixtures of phytochemicals extracted from cannabis plant materials.

This study used as a starting point, a solution consisting of purified CBDA prepared by suspending 9.2 g of a recrystallized CBD acid-triethylamine salt (20 mM) in 100 ml of ethyl acetate and then washing the suspended CBDA salt with 100 ml of a 5% HCl solution. The organic layer was dried with magnesium sulfate after which, the solvent was evaporated to yield a white gum. The white gum was dissolved in 50 ml hexane to yield a solution containing 0.4 mM of CBD acid (CBDA).

Each of the forty amines listed in Table 19 was assessed for its potential to crystallize (i.e., precipitate) CBDA from an organic solvent solution by dropwise addition of the amine into a 2.5-ml volume of the CBDA solution to provide a 50% molar excess of the amine. Each of the amines was dissolved in 2.5 ml hexane except for those as noted in Table 11. The amines that were not soluble in hexane, were solubilized in 2.5 ml ethyl acetate. For those reactions with the amines that were solubilized in ethyl acetate, an additional 5 ml of hexane was added to the reaction mixture. It is to be noted that the molecular weight of CBD is 358, and that the molecular weights for the amines tested in this study were in a range of 100 to 150. Accordingly, the yields expected were in the range of 80% to 90% of the theoretical yield (theoretical yields in a range of 450 to 500 mg), that is, about 400 mg. It is also to be noted that some scratching (i.e., abrasion) of the side walls of the reaction containers may have been required to initiate the precipitation process.

Twenty of the forty amines assessed in this study precipitated CBDA as a salt from an organic solvent solution (Table 19).

In each of the reaction vessels wherein a selected amine caused CBDA crystallization/precipitation, the remaining solution was analyzed with thin-layer chromatography to determine if any CBDA remained in solution. In all cases wherein CBDA crystallization/precipitation occurred, there was no remaining CBDA in solution indicating that all of the CBDA had been crystallized/precipitated.

Each of the salt products was filtered to remove excess amine solution, and then washed with a small volume of hexane. Each of the dried salt products was weighed and its melting point (MP) determined. All of the salt products melted above 100° C. (Table 11). Most of the measured melting points (MP) were quite narrow indicating high purity of the precipitated CBDA salt (Table 19).

TABLE 19

| AMINE | Crystals formed | Yield (mg) | MP (° C.) |
|---|---|---|---|
| Aromatic amines | | | |
| 1  aniline | No | | |
| 2  4-methoxyaniline | No | | |
| 3  pyridine | No | | |
| Primary amines | | | |
| 4  butylamine | No | | |
| 5  allyamine | No | | |
| 6  isobutylamine | No | | |
| 7  octylamine | No | | |
| 8  phenethylamine | No | | |
| 9  α-methylbenzylamine | No | | |
| 10 cyclopentylamine | No | | |
| 11 cyclohexylamine (very slow crystallization) | YES | 0.38 | 117-119 |
| 12 4-methylbenzylamine | No | | |
| Secondary amines | | | |
| 13 pyrrolidine | Formed gum | | |
| 14 diethylamine (very slow crystallization) | YES | 0.20 | 115-120 |
| 15 N-isopropylcyclohexylamine | YES | 0.40 | 131-132 |
| 16 2,2,6,6-tetramethylpiperidine | YES | 0.34 | 207-209 |

TABLE 19-continued

| AMINE | Crystals formed | Yield (mg) | MP (° C.) |
|---|---|---|---|
| Tertiary amines | | | |
| 17 triethylamine | YES | 0.41 | 176-178 |
| 18 methyldicyclohexylamine | YES | 0.45 | 115-120 |
| 19 tributylamine | YES | 0.42 | 126-129 |
| 20 tripropylamine | YES | Not. det. | |
| 21 diisopropylethylamine | YES | 0.37 | 141-143 |
| Amino alcohols | | | |
| 22 ethanolamine | No | | |
| 23 2-methylethanoloamine | No | | |
| 24 N,N-dimethylethanolamine | YES | Not det. | |
| 25 piperidineethanol | YES | 0.41 | 158-160 |
| 26 3-aminopropanol | No | | |
| 27 2-ethylethanolamine | No | | |
| Amino ethers | | | |
| 28 morpholine | YES | 0.21 | 110-117 |
| 29 N-methylmorpholine | YES | 0.40 | 163-165 |
| Diamines | | | |
| 30 N,N-dimethylethylenediamine | No | | |
| 31 N,N,N-trimethylethylenediamine | YES | 0.34 | 101-108 |
| 32 N,N,N,N-tetramethylethylenediamine | YES | 0.39 | 112-116 |
| 33 4-aminomethylpiperidine | YES | 0.38 | 123-125 |
| 34 4-dimethylaminopyridine (DMAP) | YES | 0.38 | 124-132 |
| 35 1,5-diazabicyclooctane (DABCO) (dissolved in ethyl acetate followed by addition of hexane) | YES | 0.38 | 124-132 |
| 36 1,6-hexanediaminene | No | | |
| 37 dimethylpiperazine | YES | 0.35 | 107-113 |
| Dimethylaminopyridine (DMAP) | YES | 0.38 | 124-132 |
| Highly basic amines | | | |
| 38 1,8-diazabicycloundec-7-ene (DBU) | YES | | 112-114 |
| 39 1,5-diazabicyclo(4.3.0)non-5-ene (DBN) | YES | | 124 |
| Weakly basic amines | | | |
| 40 hexanamide | No | | |

In summary, the following twenty amines precipitated a CBDA-amine salt from the organic solvent solution as follows (listed in descending order in reference to the amount of CBDA salts were crystalized from the CBDA solutions):

1. triethylamine (tertiary amine)
2. N-methylmorpholine (amino ester)
3. 1,8-diazabicycloundec-7-ene (DBU) (highly basic)
4. piperidineethanol (amino alcohol)
5. 4-dimethylaminopyridine (DMAP) (diamine)
6. cyclohexylamine (primary amine);
7. 1,5-diazabicyclooctane (DABCO) (diamine)
8. methyldicyclohexylamine (tertiary amine)
9. N,N,N,N-tetramethylethylenediamine (diamine)
10. diisopropylethylamine (tertiary amine)
11. N-isopropylcyclohexylamine (secondary amine)
12. 4-aminomethylpiperidine (diamine)
13. tributylamine (tertiary amine)
14. dimethylpiperazine (diamine)
15. N,N,N-trimethylethylenediamine (diamine)
16. 2,2,6,6-tetramethylpiperidine (secondary amine)
17. morpholine (amino ester)
18. N,N-dimethylethanolamine (amino alcohol)
19. diethylamine (secondary amine)
20. tripropylamine (tertiary amine)

All five tertiary amines assessed in this study, crystallized CBD salts from a CBDA solution. Seven of nine diamines assessed in this study, crystallized CBD salts from a CBDA solution. Three of four secondary amines assessed in this study, crystallized CBD salts from a CBDA solution. Both amino ethers assessed in this study, crystallized CBD salts from a CBDA solution. It was noted that a highly basic amine, DBU, provided a very high recovery of crystallized CBD salts from a CBDA solution. However, only two of six amino alcohols assessed in this study, crystallized CBD salts from a CBDA solution. The amine portion of both of the successful amino alcohols was a tertiary amine. None of the three aromatic amines assessed in this study produced crystalline CBD salts from a CBDA solution. Only one primary amine out of nine assessed in this study, crystallized CBD salts from a CBDA solution.

Example 7

Twelve of the CBDA-amine salts produced in Example 6, were characterized by taking their $^1$H NMR spectra in CDCl$_3$ and recording at 400 MHz. Each of the twelve CBDA-amine salts showed the expected peaks due to the ammonium ion in addition to all the peaks comprising the CBDA acid unit. The integration of the peaks was consistent with a 1:1 ratio of ammonium ion vs CBDA carboxylate. Only the six key peaks of the carboxylate portion, see structure (21) below, and key peaks due to the ammonium ion which do not overlap with the CBD carboxylate peaks are reported. The six carboxylate peaks are listed first starting with the most deshielded peak due to H1 and ending with peaks to the methyl groups 5 and 6. These peaks are found at 6.15, 5.55, 4.64, 4.50, 1,77, 1.64 ppm in CBD acid. All six peaks are singlets in each case the integration is 1:1:1:1:3:3. The peak assignment and the integration of the relevant ammonium ion peaks are also given.

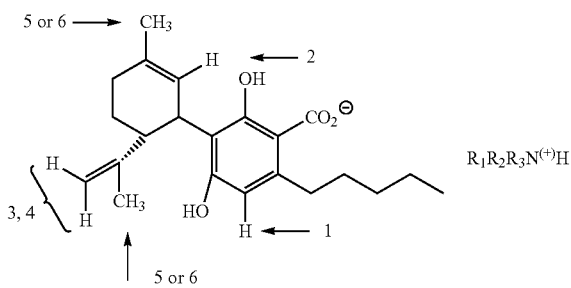

(21)

Salt 1. CBDA-triethylamine Salt

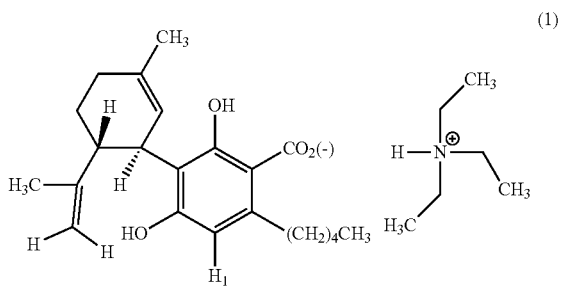

(1)

A white solid formed very readily with 99% yield, upon scratching the initial white gum. Mp. 126-127° C. with loss of CO$_2$.

$^1$H NMR (400 MHz, CDCl$_3$) CBD carboxylate. δ: 6.08, 5.55, 4.52, 4.54, 1.76, 1.72.
Ammonium ion δ: 3.02 (q, J=6.8 Hz, 6H), J=6.8 Hz, 9H)

Salt 2. CBDA-DBU Salt

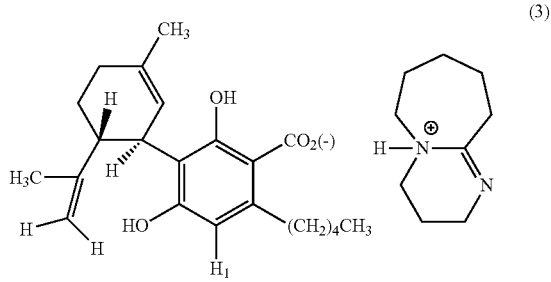

(3)

A white solid, mp. 116-126° C. with loss of CO$_2$, was obtained with a 92% yield upon scratching of the initially formed white gum.
$^1$H NMR (400 MHz, CDCl$_3$) CBD carboxylate. δ: 6.06, 5.56, 4.48, 4.461.72, 1.69;
Ammonium ion δ: 3,44 (t, 2H, (=N—CH$_2$)

Salt 3. CBDA-piperidineethanol Salt

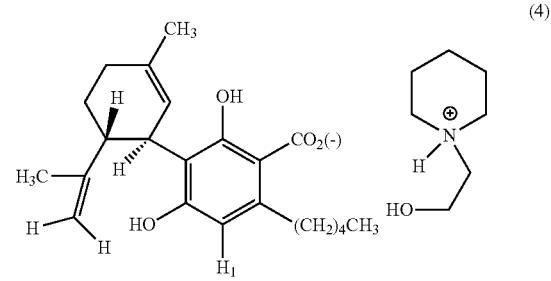

(4)

A white solid, quickly formed upon scratching with 94% isolated yield, mp 158-160° C. with loss of CO$_2$.
$^1$H NMR (400 MHz, CDCl$_3$) CBD carboxylate. δ: 6.16, 5.57, 4.49, 4.42, 1.76, 1.70.
Ammonium ion Salt 4. CBDA-cyclohexylamine Salt

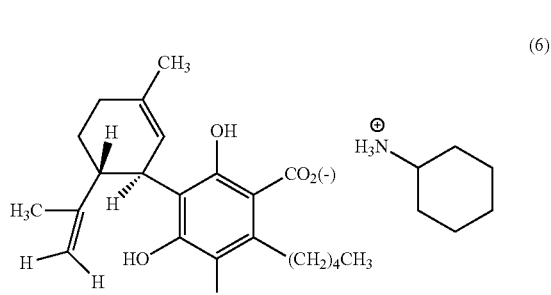

(6)

$^1$H NMR (400 MHz, CDCl$_3$) CBD carboxylate. δ: 6.13. 5.52, 4.46, 4.41, 1.75, 1.67.

Salt 5. CBDA-DABCO Salt

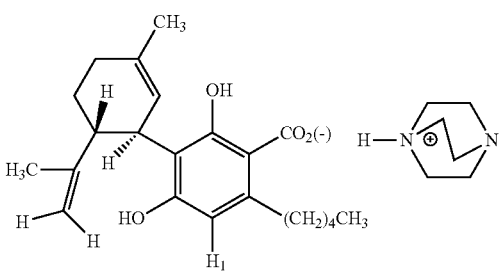 (7)

This salt was obtained by dissolving 3 mmol of DABCO in 5 ml of ethyl acetate and then adding 2. ml (2.0 mmol) of the CBD acid solution. The combined solvent was evaporated to about half the original volume and then 5 ml of hexane was added. The white solid formed was isolated by filtration. The yield was 92%. Mp: 124-132° C. with loss of $CO_2$.

$^1$H NMR (400 MHz, $CDCl_3$) CBD-carboxylate. δ: 6.10, 5.55, 4.50, 4.43, 1.74, 1.69:

Ammonium ion δ: 2.99 (s, 12H, 6×$CH_2$—N).

Salt 6. CBDA-methyldicyclohexylmethylamine Salt

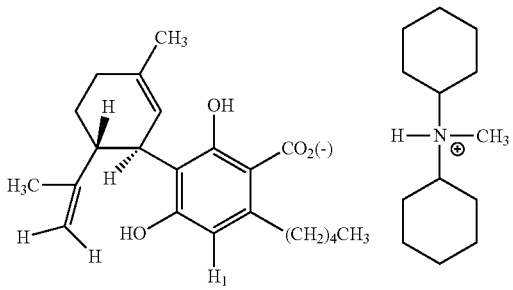 (8)

The initial white gum became a solid upon scratching. The yield of white solid mp. 115-120° C. with loss of $CO_2$ was 91%.

Salt 7. CBDA-TMEDA Salt

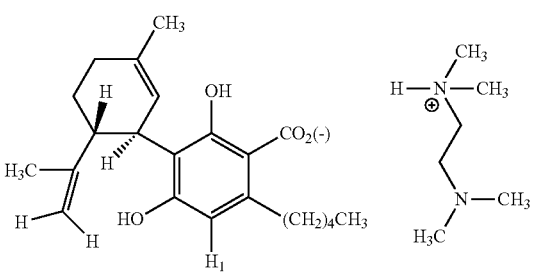 (9)

A white gum which readily solidified to yield a white solid Mp 112-116° C. with loss of $CO_2$ with a 91% yield.

$^1$H NMR (400 MHz, $CDCl_3$) CBD carboxylate. δ: 6.11 5.56, 4.51, 4.44, 1.74, 1.70.

Ammonium ion δ: 2.80 (s, 4H, $CH_2$N), 2.45 (s. 12H, $(CH_3)_2$N $^{13}$C NMR: 176.43, 162.85, 157.77, 147.83, 147.68, 147.80, 1=147.68, 147.66, 125.06, 113.67. 110.78, 109.51, 108.39.

Salt 8. CBDA-diisopropylethylamine Salt

 (10)

$^1$H NMR (400 MHz, $CDCl_3$) CBD carboxylate. δ: 6.15 (b5, 1H), 6.08 (5, 1H), 5.56 (5, 1H), 4,49 (q. 1H), 4.45 (5, 1H) 1.73 (5, 3H), 1.69 (5, 3H), (t, 3H).

Ammonium ion δ: 3.68 (sep. 2H, N—CH), 3.06 (q, 2H, N—$CH_2$) 1.38 (d, 12H, 4×CH3)

Salt 9. CBDA-tributylamine Salt

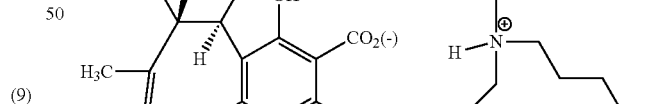 (12)

A white solid formed quickly with 85% yield. Mp. 126-129° C. with loss of $CO_2$.

$^1$H NMR (400 MHz, $CDCl_3$) CBD-carboxylate. δ: 6.08, 5.55, 4.52, 4.54, 1.76, 1.72.

Ammonium ion δ: 3.02 (q, J=6.8 Hz, 6H), 1.13 (t, J=6.8 Hz, 9H)

Salt 10. CBDA-methylpiperazine Salt

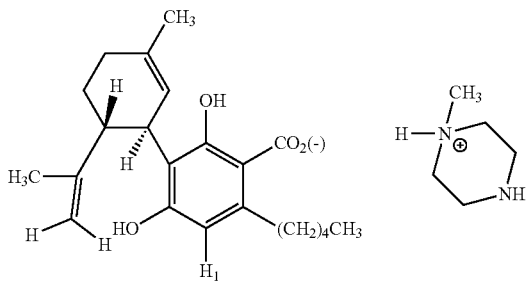

(13)

¹H NMR (400 MHz, CDCl₃) CBD carboxylate. δ: 6.13 bs, 1H), 5.57 (s, 1H), 4.49 (q. 1H), 4.44 (s, 1H) 1.75 (s, 3H), 1.70 (5, 3H), 0.85 (t, 3H).
Ammonium ion δ: 3.09 (4H, 2×N—CH₂), 2.55 (4H, 2×N—CH₂) 2.26 (s, 3H, N—CH₃).

Salt 11. CBDA-dimethylaminoethanol Salt

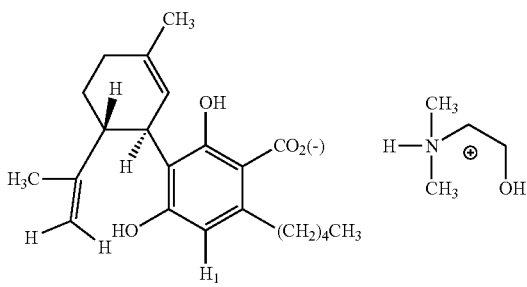

(17)

A white solid formed quickly with 85% yield. Mp. 126-127° C. with loss of $CO_2$.
¹H NMR (400 MHz, CDCl₃) CBD carboxylate. δ: 6.11, 5.55, 4.51, 4.4.44, 1.77, 1.70:
Ammonium ion δ: 6.11, 5.55, 4.51, 4.44, 1.74, 1.70; amine: 3.90 (t, 2H, CH₂—O) 3.03 (t, 2H, CH₂—N), 2.73 (s, 6H, N(CH₃)₂)

Salt 12. CBDA-morpholine Salt

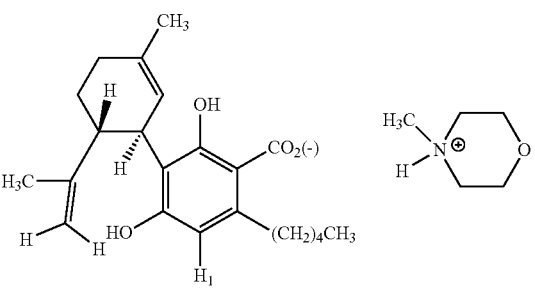

(16)

A white solid mp 117-119° C. with loss of $CO_2$, was obtained with a 52% yield.
¹H NMR (400 MHz, CDCl₃) CBD carboxylate. δ: 6.16, 5.57, 4.49, 4.42, 1.76, 1.70.
Ammonium ion δ: 3.84 (4H, 2×CH₂—O), 3.08 (4H 2×, N—CH2)

Example 8

The purpose of this study was to determine suitable hydrocarbon solvent options for washing the amine-precipitated crude cannabinoid isolate, to remove impurities therefrom thereby producing the purified cannabinoid precipitate.

A crude resinous extract prepared from hemp biomass was dissolved in heptane after which, a triethylamine solution was added dropwise to the crude extract heptane solution to produce a crude cannabinoid precipitate. Subsamples of the crude cannabinoid precipitate were washed with one of the following solvents:
ethyl acetate
toluene
tetrahydrofuran (THF)
95% ethanol
methanol
isopropanol
dichloromethane
methyl tert-butyl ether (MTBE)

Each of the subsamples was weighed prior to and after washing, and again prior to and after drying with a selected solvent to determine potential loss of product. The color of the washed precipitate subsamples was recorded. Each of the washed precipitate subsamples was assayed by HPLC as outlined in Example 2.

The initial study showed that all seven solvents assessed in this study purified the selected target cannabinoid, i.e., CBD, CBDA, CBDA-amine salt. The best performing solvents were ethyl acetate, 95% ethanol, isopropanol, and MTBE.

Example 9

A first method for decarboxylation of a CBD-triethylamine salt is disclosed in this example.

A CBD acid-triethylamine salt was recovered from crude resinous extract prepared from hemp biomass, by stepwise addition of triethylamine into the crude resinous extract that was dissolved in hexane.

The CBD acid-triethylamine salt was dissolved in a 2.5% sodium carbonate solution ($Na_2CO_3$) at 70° C. This solution was placed into a reflux condenser and then heated to and maintained at 100° C. 3° C. for 4 h to 6 h. Triethylamine ($NEt_3$) has a boiling point of 88° C. During the 4 h to 6 h reaction time period at 100° C. 3° C., the triethylammonium salt of the CBD acid is converted the sodium salt of CBD acid and triethylammmonium carbonate and the triethylammmonium carbonate comes into equilibrium with triethylamine and carbonic acid. Over the period of time, it is reasonable to expect that all of the triethylammonium carbonate will be separated from the CBD sodium salt whereby the CBD sodium salt will be in the form of an oil. The triethylammonium carbonate will have been converted to triethylamine, carbon dioxide and water. Because triethylamine is not miscible in water, triethylamine can be separately recovered by partition separation, and recycled for reuse. It should be noted that the concentration of sodium carbonate solution for dissolving the CBD acid triethylamine salt may be from the range of 1% to 15%, for example 1.5%, 2%, 3%, 4%, 5%, 10%, 15%, and therebetween.

The chemical equations for this decarboxylation method are:

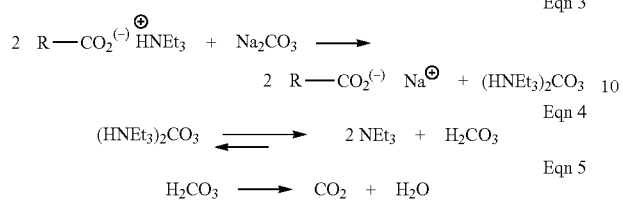

$$2\ R\text{—}CO_2^{(-)}\ \overset{\oplus}{H}NEt_3 + Na_2CO_3 \longrightarrow$$

$$2\ R\text{—}CO_2^{(-)}\ Na^{\oplus} + (HNEt_3)_2CO_3 \quad \text{Eqn 3}$$

$$(HNEt_3)_2CO_3 \rightleftharpoons 2\ NEt_3 + H_2CO_3 \quad \text{Eqn 4}$$

$$H_2CO_3 \longrightarrow CO_2 + H_2O \quad \text{Eqn 5}$$

Example 10

A second method for decarboxylation of a CBD-triethylamine salt is disclosed in this example.

A CBD acid-triethylamine salt was recovered from crude resinous extract prepared from hemp biomass, by stepwise addition of triethylamine into the crude resinous extract that was dissolved in hexane.

The second method is based on conversion of the CBD acid-triethylamine salt into a free acid by a reaction with HCl in a selected solvent. A suitable solvent is ethyl acetate or dichloromethane and the like. A suitable concentration of HCl is from a range of 1% to 30%, for example 2%, 3%, 4%, 5%, 10%, 15%, 20%, 25%, 30%, and therebetween.

For this example, the first step was mixing the CBD acid-triethylamine salt with a 5% HCl solution using ethyl acetate as the solvent, until the salt was completely dissolved. This reaction produced CBD acid in the organic layer and triethylamine in the water layer as its hydrochloride. The two layers were separated, after which, the organic layer was dried and the solvent evaporated to yield CBD acid as a viscous fluid.

The second step was decarboxylating the CBD acid in a 2.5% carbonate solution at about 100° C.±3° C. for 4 h to 6 h whereby CBD is recovered in crystalline form. It is to be noted that a suitable carbonate solution for this step is from a range of 1% to 20%, for example 2%, 3%, 4%, 5%, 10%, 15%, and therebetween.

Triethylamine is recovered from the aqueous layer by the addition of sodium hydroxide (NaOH) thereby causing separation of the triethylamine into a less-dense organic layer thereby facilitating its recovery and recycling.

The chemical equations for the second decarboxylation method are:

$$R\text{—}CO_2^{(-)}\ \overset{\oplus}{H}NEt_3 + HCl \longrightarrow \quad \text{Eqn 6}$$

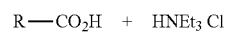

$$R\text{—}CO_2H + HNEt_3Cl$$

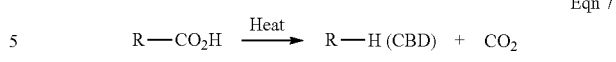

$$R\text{—}CO_2H \xrightarrow{\text{Heat}} R\text{—}H\,(CBD) + CO_2 \quad \text{Eqn 7}$$

$$HNEt_3Cl + NaOH \longrightarrow NEt_3 + NaCl \quad \text{Eqn 8}$$

Example 11

Varying amounts of denatured alcohol or acetone were added to a standardized CBDA stock solution, to assess their effects on amine precipitation of CBDA from the standardized CBDA stock solution.

The denatured alcohol or acetone was added to aliquots of the standardized CBDA stock solution immediately prior to the addition of triethylamine. Following the addition of triethylamine, the samples were vortexed, filtered, and then the precipitated salts were washed with 30 ml of cold heptane. The yield of each salt was measured by taking the (i) mass of the salt and (ii) the difference between the concentration of CBDA in the standardized CBDA stock solution prior to the addition of triethylamine solution, and the concentration of CBDA in the filtrate following filtration. The concentrations were measured by the Agilent HPLC system. Table 20 below shows the yields of precipitated CBDA-triethylamine salts.

After the precipitated salts were dried, each salt was recrystallized by dissolving the salt in a 10:1 volume of hot ethyl acetate, then spiked with 1.5% heptane by volume, and the solutions were cooled to about 30° C. prior to placing the solution in a 4° C. refrigerator overnight. The recrystallized CBDA salts were filtered from the solutions, washed in cold heptane, then filtered and dried.

With the addition of triethylamine to a standardized CBDA stock solution dissolved in denatured alcohol, the CBDA salt did not precipitate at room temperature. Therefore, the solution was placed in a freezer overnight to obtain a CBDA-triethylamine salt precipitate.

With the addition of triethylamine dissolved in 50% ethanol/heptane solution, the resulting CBDA-triethylamine salt precipitate was slightly more pure than the CBDA-triethylamine salt precipitated by the addition of triethylamine solubilized in 100% heptane. However the yield of the CBDA-triethylamine salt was reduced (Table 20).

The addition of acetone to the standardized extract prior to the addition of triethylamine, resulted in higher purity CBDA salt precipitates following recrystallization (Table 20).

Overall, it was observed that an increase in polarity of the standardized extract increased the purity of the CBDA salt precipitate (by the addition of denatured alcohol or acetone), but reduced yield (Table 20).

TABLE 20

| Sample | Dilutant | Dilutant % by volume | Relative Polarity | MI molar excess | Crude Precipitate Yield | Crude Precipitate Purity % weight/ weight | Recrystallization Yield | Recrystallized Purify % weight/ weight |
|---|---|---|---|---|---|---|---|---|
| 1 | none | — | — | 0.01 | 3 | 98.9% | 81.4% | 37.1% | 91.7% |
| 2 | none | — | — | 0.01 | 3 | 99.5% | 80.8% | | |
| 3 | none | — | — | 0.07 | 1.5 | 99.1% | 74.8% | 98.6% | 91.6% |
| 4 | denatured ethanol | 9.1% | 0.07 | 3 | 93.7% | 81.3% | 91.5% | 93.1% |

TABLE 20-continued

| Sample | Dilutant | Dilutant % by volume | Relative Polarity | MI molar excess | Crude Precipitate Yield | Crude Precipitate Purity % weight/weight | Recrystallization Yield | Recrystallized Purify % weight/weight |
|---|---|---|---|---|---|---|---|---|
| 5 | denatured ethanol | 9.1% | 0.07 | 5 | 95.1% | 100.3% | 95.7% | 97.4% |
| 6 | denatured ethanol | 9.1% | 0.07 | 1.5 | 95.6% | 86.7% | 31.8% | 34.1% |
| 7 | denatured ethanol | 4.8% | 0.04 | 3 | 97.0% | 84.9% | 31.4% | 39.7% |
| 8 | denatured ethanol | 3.4% | 0.03 | 3 | 97.8% | 86.1% | 96.5% | 90.6% |
| 9 | denatured ethanol | 2.9% | 0.03 | 3 | 98.0% | 83.8% | 31.7% | 39.6% |
| 10 | denatured ethanol | 2.4% | 0.03 | 3 | 97.8% | 83.7% | 39.8% | 93.2% |
| 11 | denatured ethanol | 50.0% | 0.34 | 3 | 75.1% | 84.8% | 67.6% | 97.2% |
| 12 | denatured ethanol | 100% | 0.67 | 3 | 31.8% | 85.6% | 72.2% | 95.1% |
| 13 | Acetone | 4.8% | 0.03 | 3 | 100.m-. | 81.1% | 91.5% | 37.6% |
| 14 | Acetone | 9.1% | 0.04 | 3 | 98.6% | 83.5% | 95.5% | 93.0% |
| 15 | Acetone | 9.1% | 0.04 | 5 | 96.9% | 81.5% | 37.9% | 93.2% |
| 16 | Acetone | 16.7% | 0.07 | 3 | 97.6% | 84.8% | 92.0% | 96.4% |

Example 12

Figure 10A:
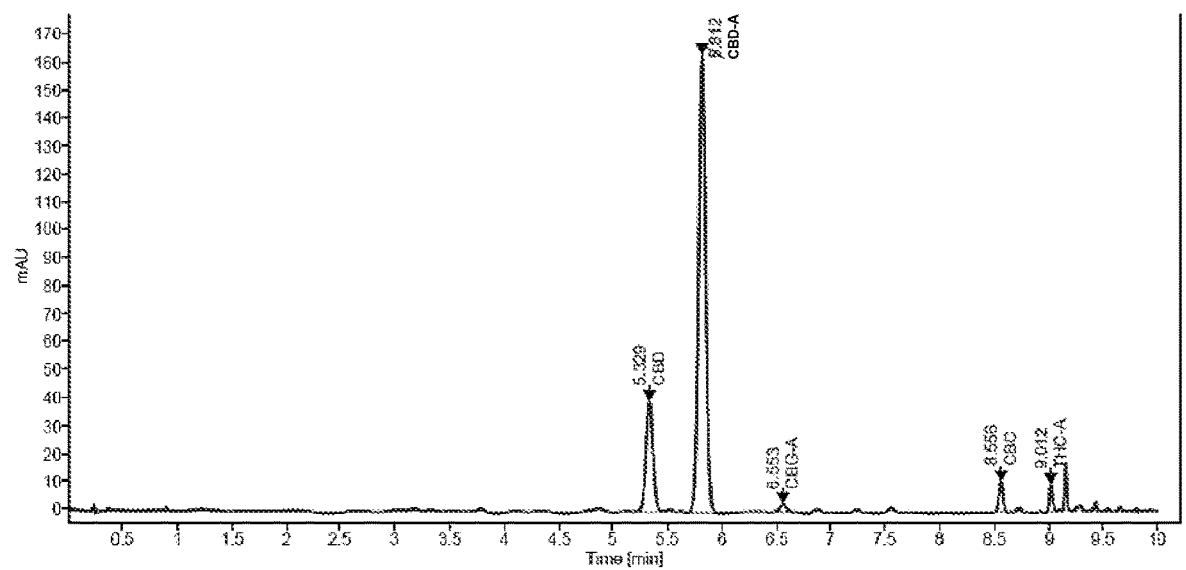
FIG. 10A is an HPLC chromatogram showing the cannabinoid composition of a crude cannabis extract standardized stock solution used in Example 12.

This study further assessed the ability of nine selected amines to precipitate CBDA-amine salts from a stock solution of a crude cannabis extract in heptane, standardized to contain 36.632 mg/ml of CBDA. HPLC analysis indicated that the cannabis CBDA standardized stock solution contained 73.30% of CBDA, 18.26% of CBD, and trace amounts of CBGA (1.31%), CBC (2.84%), and THCA (1.82%) (FIG. 10A, Table 21).

TABLE 21

| Name | RT | Peak Area % | Amount [ng] | Concentration [µg/mL] |
|---|---|---|---|---|
| CBD | 5.329 | 18.26 | 87.437 | 17.4873 |
| CBD-A | 5.812 | 73.30 | 183.160 | 36.6319 |
| CBG-A | 6.553 | 1.31 | 3.161 | 0.6321 |
| CBC | 8.556 | 2.84 | 6.192 | 1.2384 |
| THC-A | 9.012 | 1.82 | 5.873 | 1.1746 |

The following amines were assessed in this study:

| | |
|---|---|
| 1. | tributylamine (TBA) |
| 2. | tripropylamine (TPA) |
| 3. | dimethylethanolamine (DMEA) |
| 4. | piperidineethanol |
| 5. | DABCO |
| 6. | TMEDA |
| 7. | Quinine |
| 8. | DBU |
| 9. | DBN |

Figure 10B:
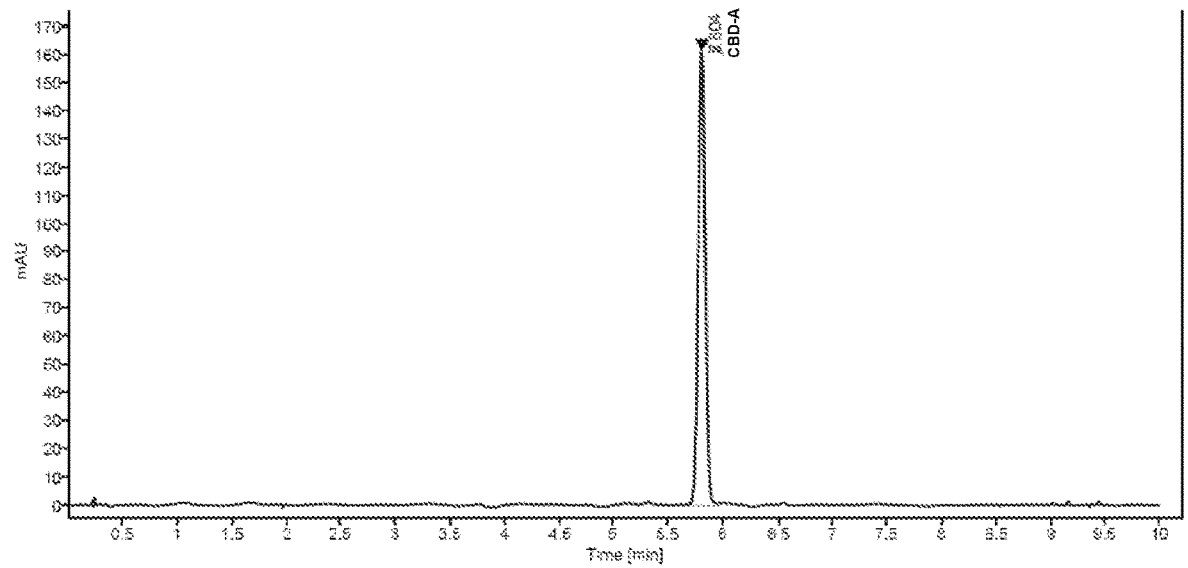
FIG. 10B is an HPLC chromatogram showing the cannabinoid content of a crude CBDA-tributylamine (TBA) salt precipitated from the standardized stock solution used in Example 12.
Figure 10C:
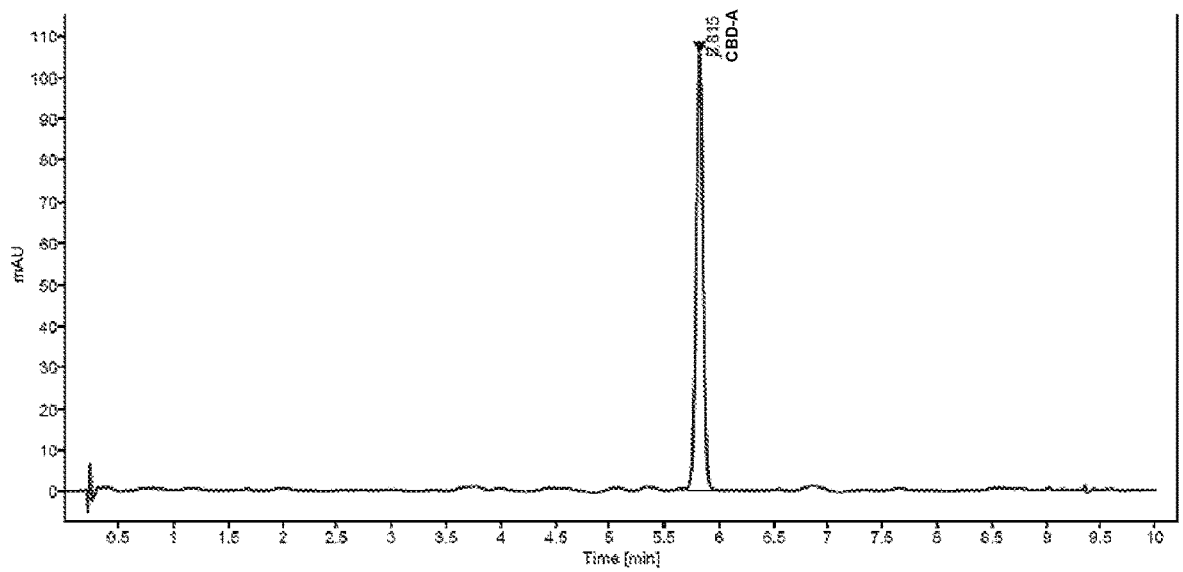
FIG. 10C is an HPLC chromatogram showing the cannabinoid content of a recrystallized purified CBDA-TBA salt precipitated from the crude CBDA-TBA salt shown in FIG. 10B.
Figure 11A:
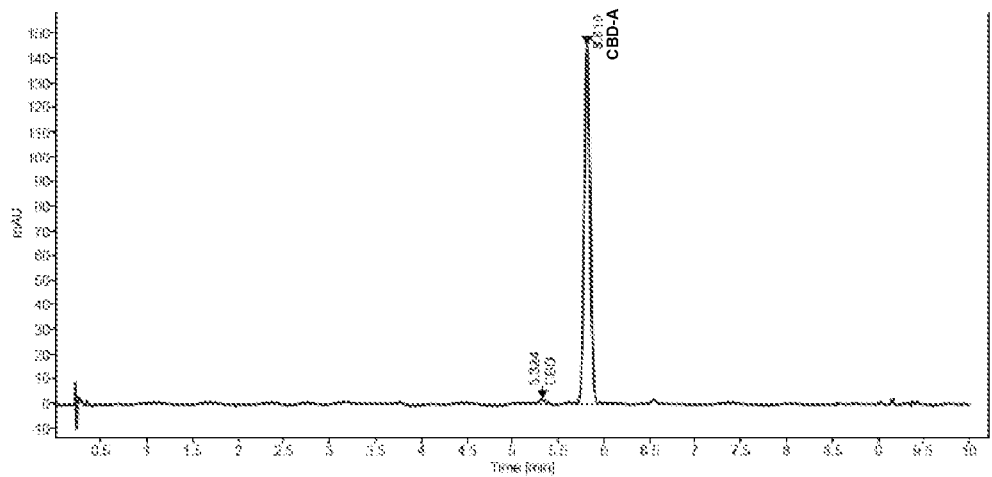
FIG. 11A is an HPLC chromatogram showing the cannabinoid content of a crude CBDA-tripropylamine (TPA) salt precipitated from the standardized stock solution used in Example 12.
Figure 12A:
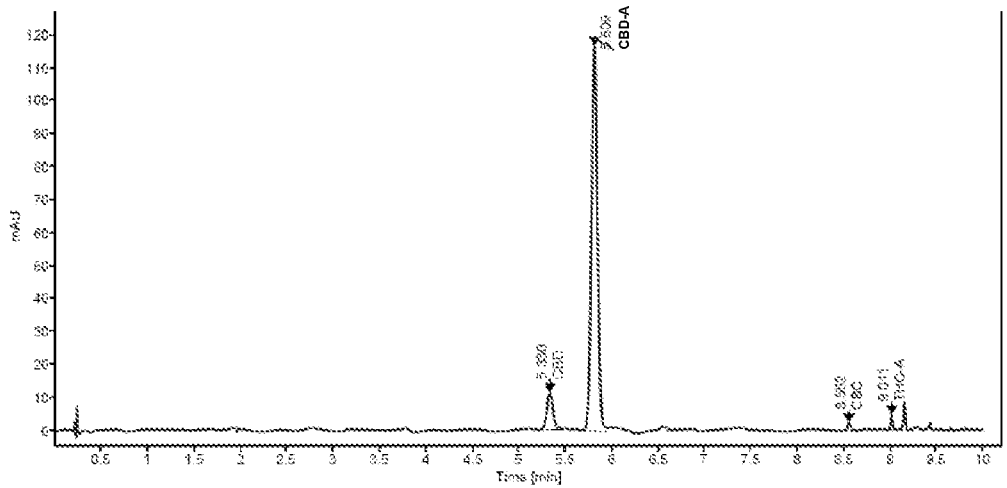
FIG. 12A is an HPLC chromatogram showing the cannabinoid content of a crude CBDA-dimethylethanolamine (DMEA) salt precipitated from the standardized stock solution used in Example 12.
Figure 13A:
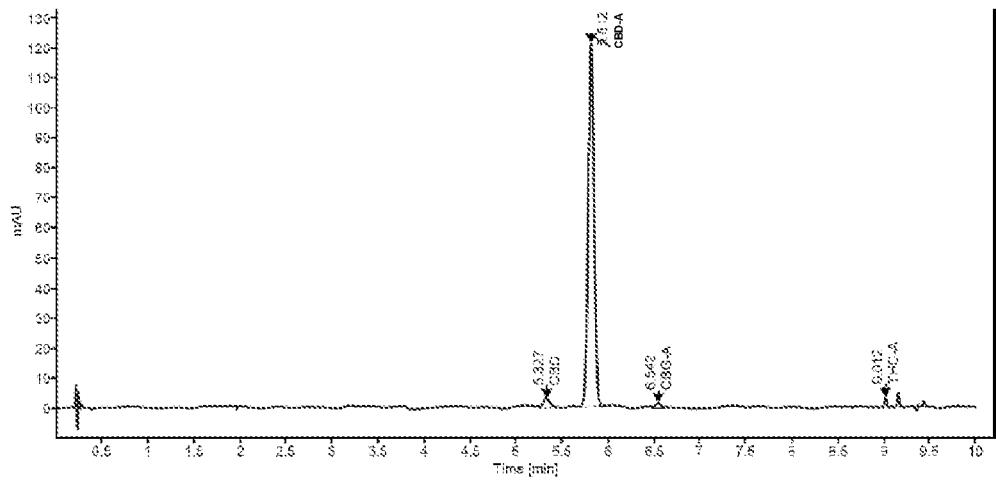
FIG. 13A is an HPLC chromatogram showing the cannabinoid content of a crude CBDA-piperidineethanol salt precipitated from the standardized stock solution used in Example 12.
Figure 14A:
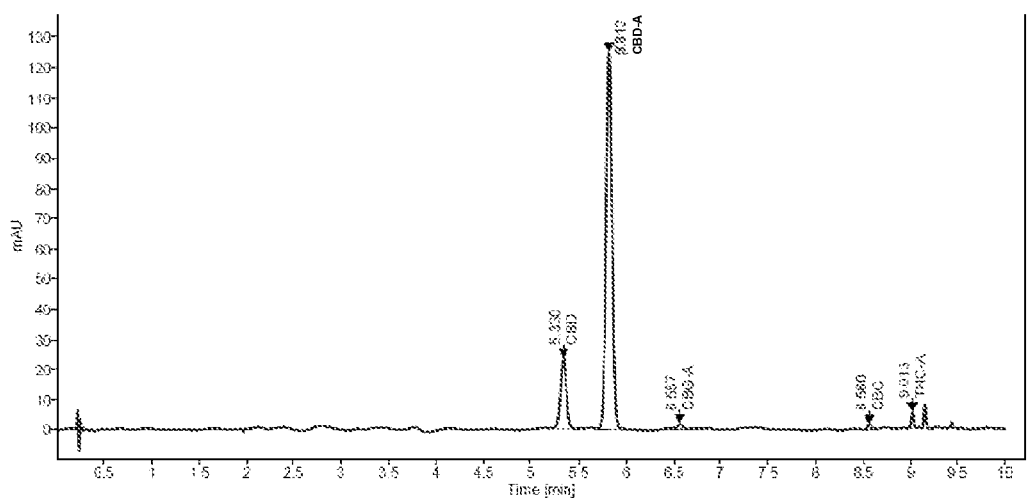
FIG. 14A is an HPLC chromatogram showing the cannabinoid content of a crude CBDA-1,4-diazabicyclo[2.2.2]octane (DABCO) salt precipitated from the standardized stock solution used in Example 12.
Figure 15A:
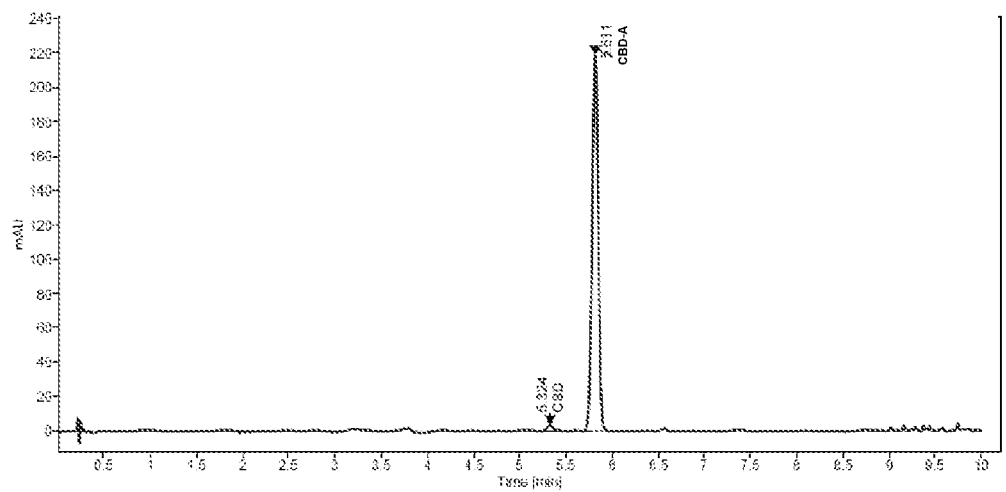
FIG. 15A is an HPLC chromatogram showing the cannabinoid content of a crude CBDA-tetramethylethylenediamine (TMEDA) salt precipitated from the standardized stock solution used in Example 12.
Figure 16A:
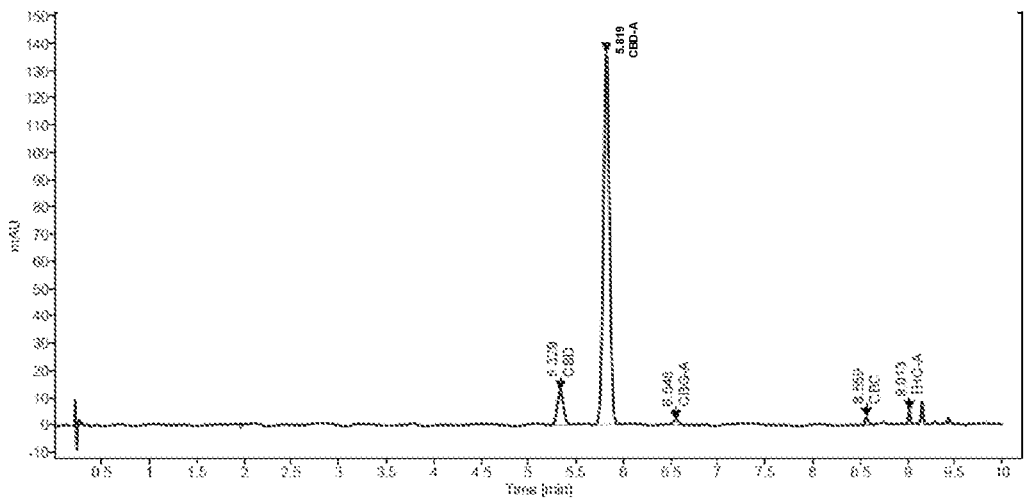
FIG. 16A is an HPLC chromatogram showing the cannabinoid content of a crude CBDA-quinine salt precipitated from the standardized stock solution used in Example 12.
Figure 17A:
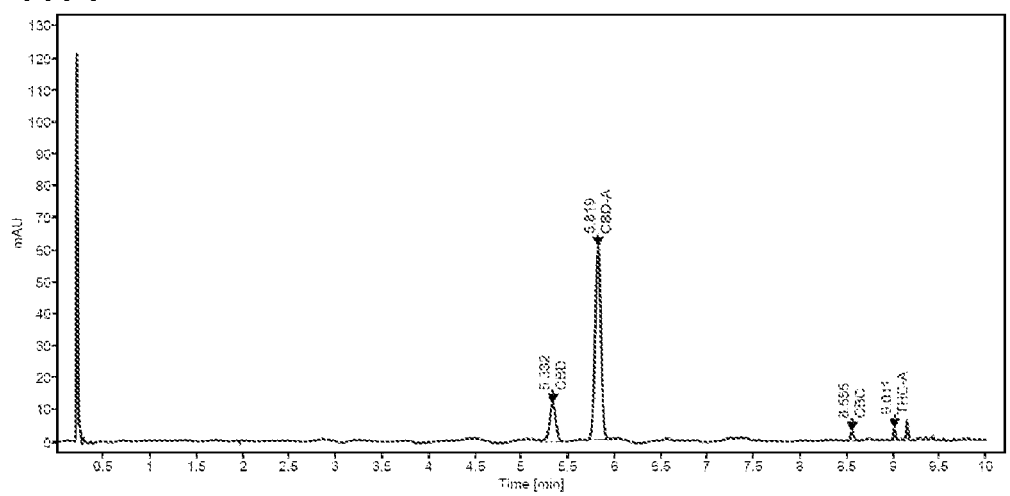
FIG. 17A is an HPLC chromatogram showing the cannabinoid content of a crude CBDA-1,8-diazabicyclo[5.4.0]undec-7-ene (DBU) salt precipitated from the standardized stock solution used in Example 12.
Figure 18A:
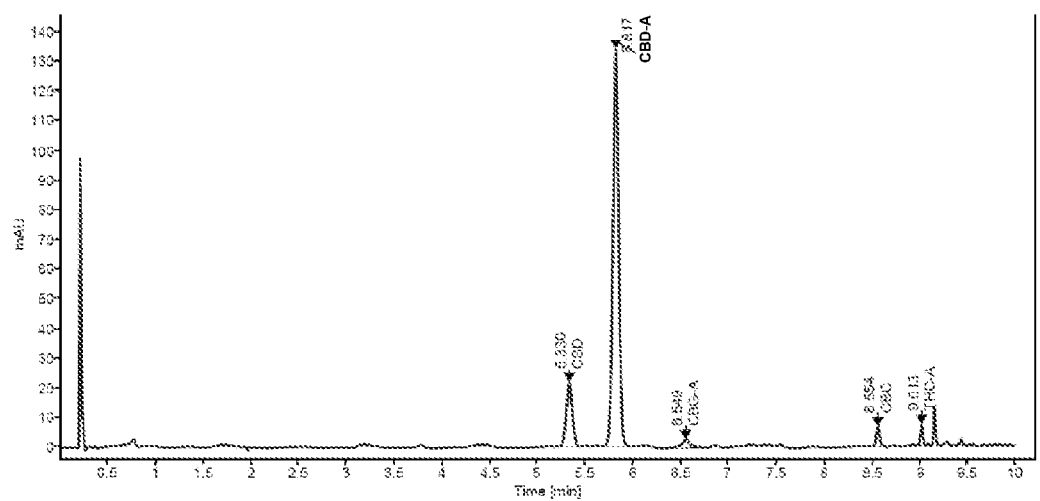
FIG. 18A is an HPLC chromatogram showing the cannabinoid content of a crude CBDA-DBN salt precipitated from the standardized stock solution used in Example 12.

Each of the amines assessed was dissolved in heptane prior to addition to the crude CBDA stock solutions with the exception of DABCO which was solubilized in ethyl acetate and quinine which was solubilized in dichloromethane. A 3:1 molar ratio of each amine was added dropwise to duplicate 35-ml volumes of the crude CBDA stock solution while mixing by sonication to thereby cause precipitation of a solid crude CBDA-amine salt. Precipitation was encouraged by cooling the reaction mixture to −20° C. for up to 24 hr. For each of the reaction mixtures, the solid crude CBDA-amine salt was separated from the liquid phase by vacuum filtration, washed with 40 ml cold heptane, dried under vacuum (Table 22), and then analyzed by HPLC (FIG. 10B, crude CBDA-TBA salt; FIG. 11A, crude CBDA-TPA salt; FIG. 12A, crude CBDA-OMEA salt; FIG. 13A, crude CBDA-piperidineethanol salt; FIG. 14A, crude CBDA-DABCO salt; FIG. 15A, crude CBDA-TMEDA salt; FIG. 16A, crude CBDA-quinine salt; FIG. 17A, crude CBDA-DBU salt; FIG. 18A, crude CBDA-DBN salt).

TABLE 22

| Amine | Crude CBDA-amine salt (g) | Purified CBDA-amine salt (g) | Decarboxylated CBD oil (g) | Purity of CBD oil (%) |
|---|---|---|---|---|
| Triethylamine | 4.307 | 3.151 | 1.880 | 100% |
| Tripropylamine | 3.849 | 2.589 | 1.595 | 100% |
| DMEA | 4.432 | 2.572 | 1.630 | 100% |
| PiperidineEtOH | 4.789 | 3.218 | 1.921 | 100% |
| DABCO | 4.980 | 2.380 | 1.718 | 100% |
| TMEDA | 2.396 | 1.614 | 1.211 | 100% |
| Quinine | 2.976 | 1.748 | 1.057 | 100% |
| DBU | 8.754 | 2.189 | 1.179 | 100% |
| DBN | 8.907 | 1.205 | 0.740 | 100% |

Figure 11B:
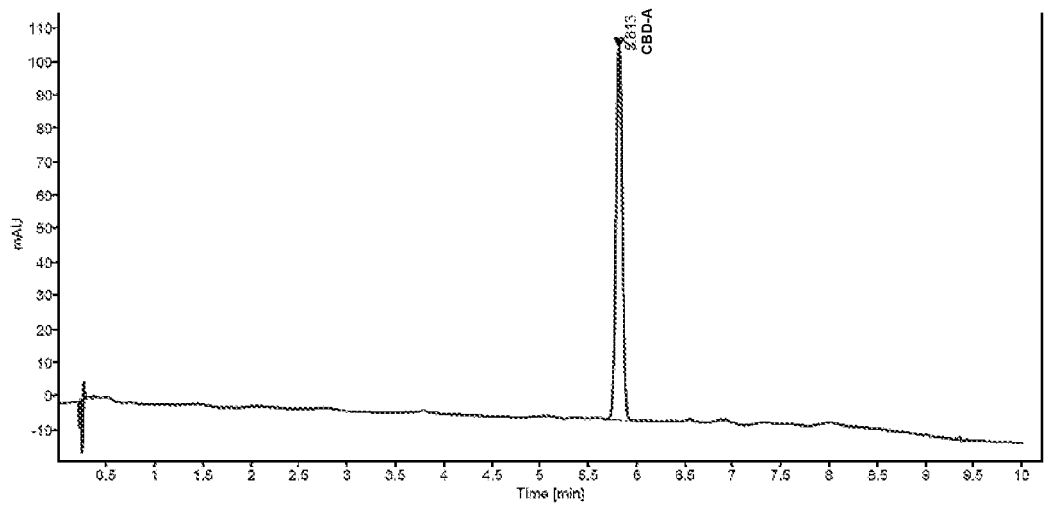
FIG. 11B is an HPLC chromatogram showing the cannabinoid content of a recrystallized purified CBDA-TPA salt precipitated from the crude CBDA-TPA salt shown in FIG. 11A.
Figure 12B:
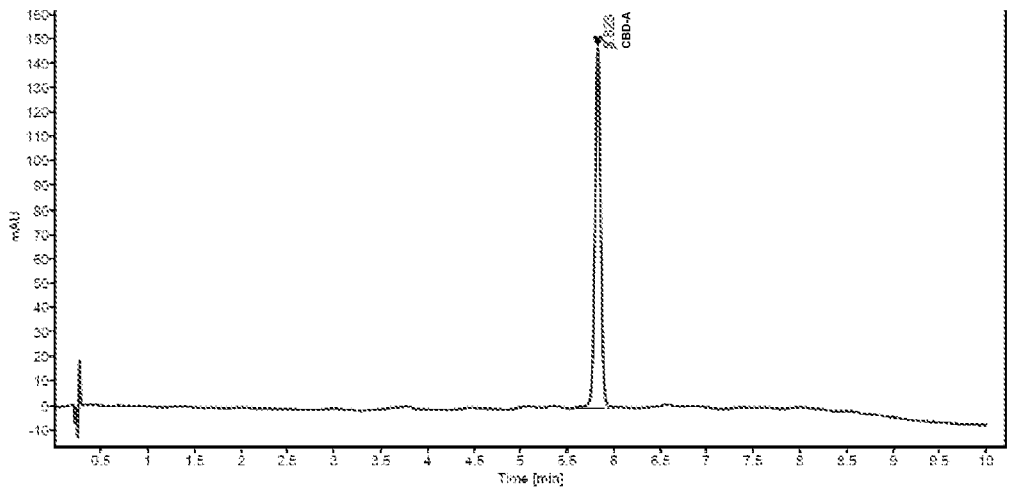
FIG. 12B is an HPLC chromatogram showing the cannabinoid content of a recrystallized purified CBDA-DMEA salt precipitated from the crude CBDA-DMEA salt shown in FIG. 12A.
Figure 13B:
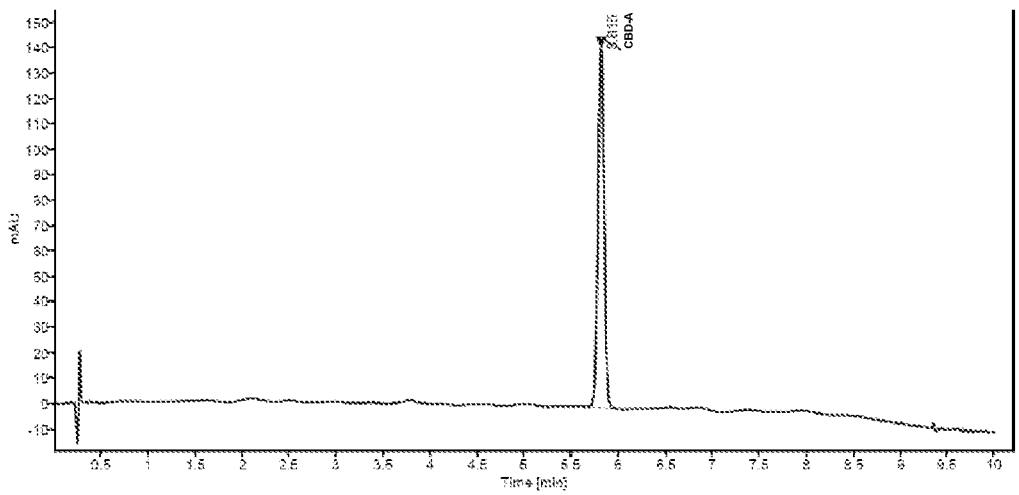
FIG. 13B is an HPLC chromatogram showing the cannabinoid content of a recrystallized purified CBDA-piperidineethanol salt precipitated from the crude CBDA-piperidineethanol salt shown in FIG. 13A.
Figure 14B:
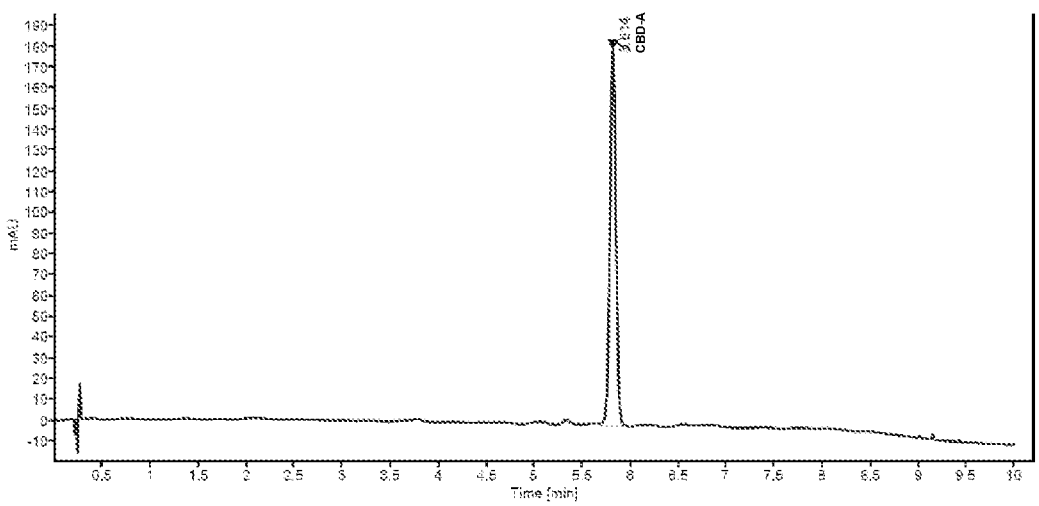
FIG. 14B is an HPLC chromatogram showing the cannabinoid content of a recrystallized purified CBDA-DABCO salt precipitated from the crude CBDA-DABCO salt shown in FIG. 14A.
Figure 15B:
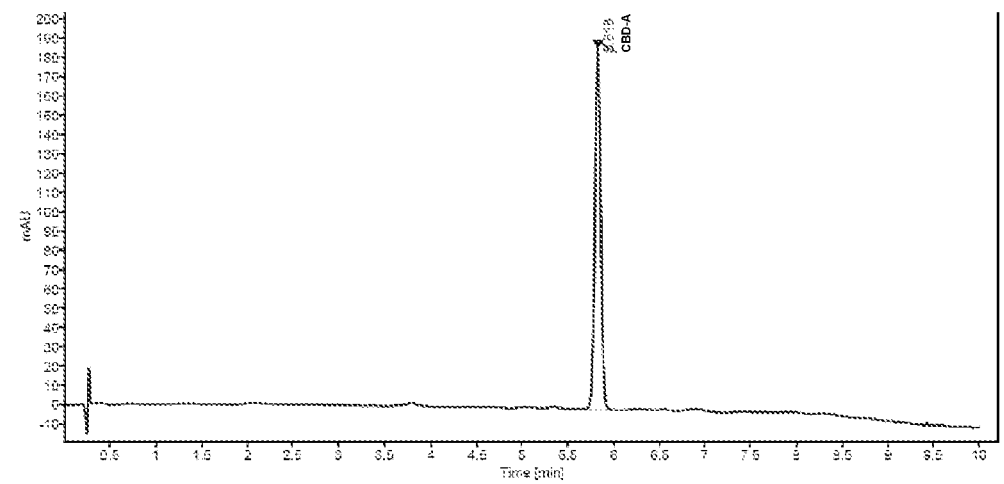
FIG. 15B is an HPLC chromatogram showing the cannabinoid content of a recrystallized purified CBDA-TMEDA salt precipitated from the crude CBDA-TMEDA salt shown in FIG. 15A.
Figure 16B:
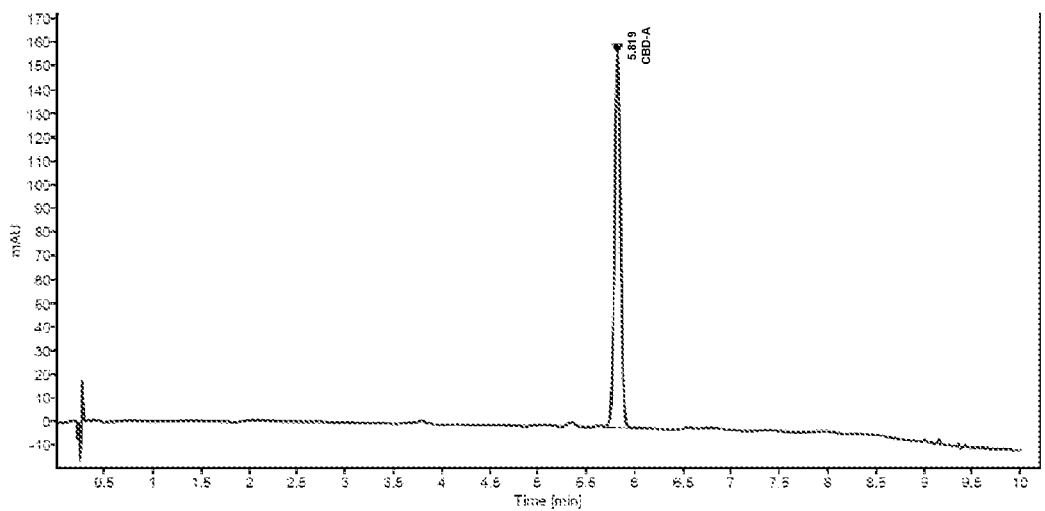
FIG. 16B is an HPLC chromatogram showing the cannabinoid content of a recrystallized purified CBDA-quinine salt precipitated from the crude CBDA-quinine salt shown in FIG. 16A.
Figure 17B:
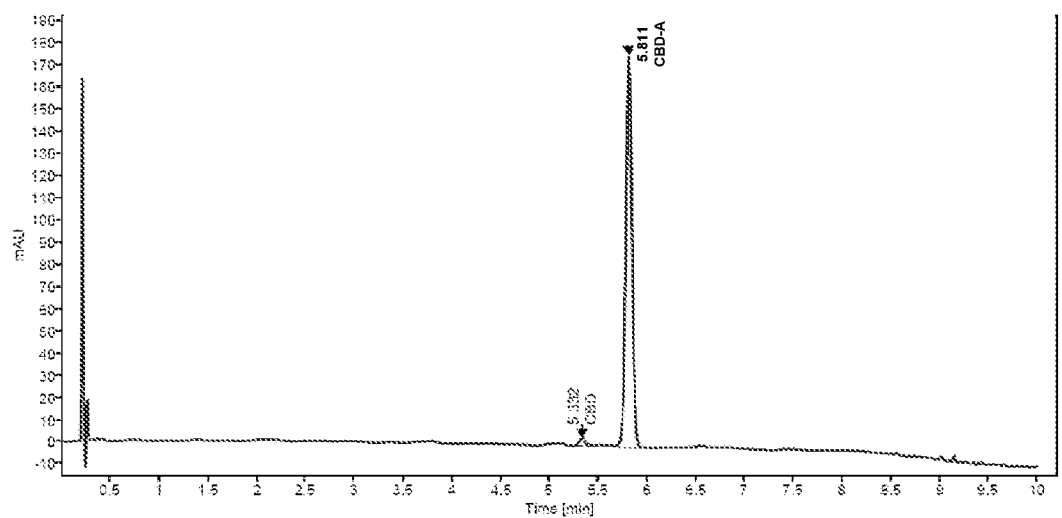
FIG. 17B is an HPLC chromatogram showing the cannabinoid content of a recrystallized purified CBDA-DBU salt precipitated from the crude CBDA-DBU salt shown in FIG. 17A.
Figure 18B:
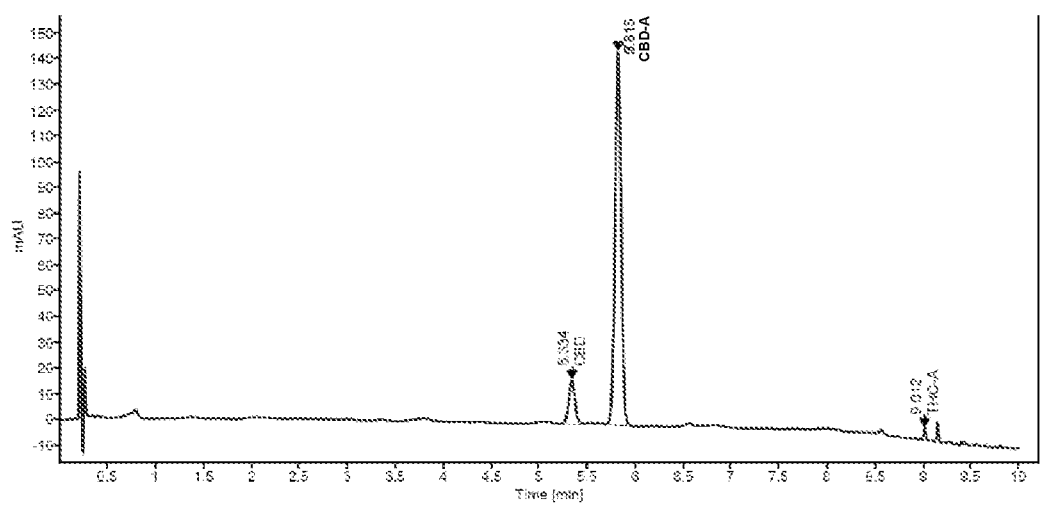
FIG. 18B is an HPLC chromatogram showing the cannabinoid content of a recrystallized purified CBDA-DBN salt precipitated from the crude CBDA-DBN salt shown in FIG. 18A.

The duplicate samples of washed and dried CBDA-amine salts were combined and then solubilized in ethyl acetate recrystallized by dissolving the salt in ethyl acetate (5:1 volume/mass) under refluxing conditions. The solubilized CBDA-amine salts were then cooled under ambient conditions to about 30° C. whereby the CBDA-amine salts began to recrystallize. The recrystallizing solutions were then cooled to 4° C. for 2 hours, and then stored at −20° C. for about 18 hours. Each of the recrystallized purified CBDA-amine salts were then separated from their liquid phase by vacuum filtration, washed with 40 ml cold heptane, dried under vacuum, and analyzed by HPLC (Table 22; FIG. 100, purified CBDA-TBA salt; FIG. 11B, purified CBDA-TPA salt; FIG. 12B, purified CBDA-DMEA salt; FIG. 13B, purified CBDA-piperidineethanol salt; FIG. 14B, purified CBDA-DABCO salt; FIG. 15B, purified CBDA-TMEDA salt; FIG. 16B, purified CBDA-quinine salt; FIG. 17B, purified CBDA-DBU salt; FIG. 18B, purified CBDA-DBN salt).

Figure 10D:
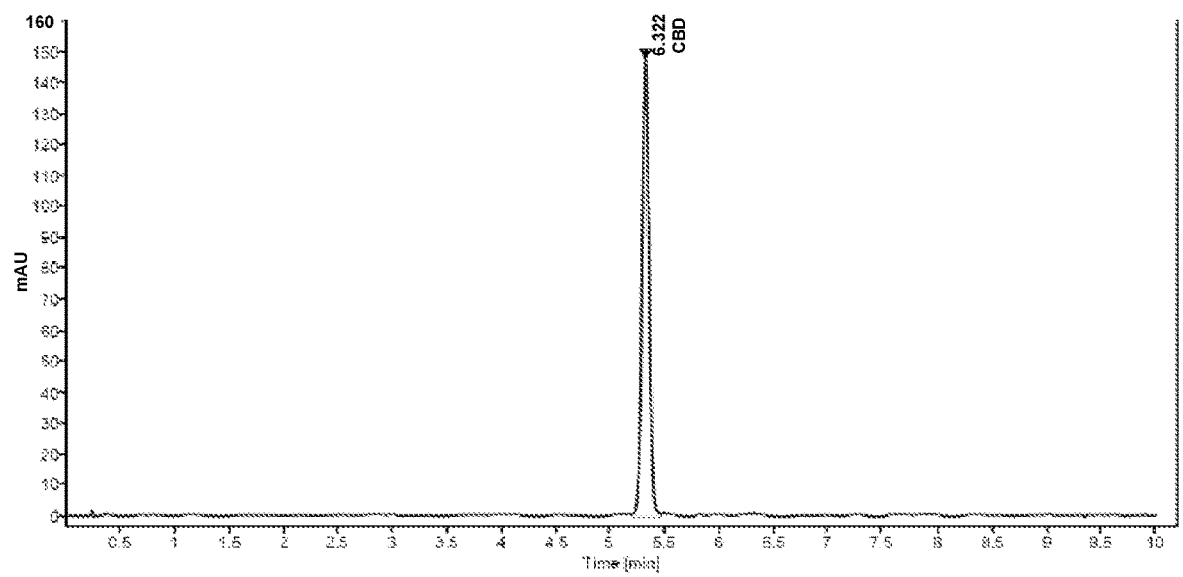
FIG. 10D is an HPLC chromatogram showing the cannabinoid content of a decarboxylated CBD oil recovered from the purified CBDA-TBA salt shown in FIG. 10C.
Figure 11C:
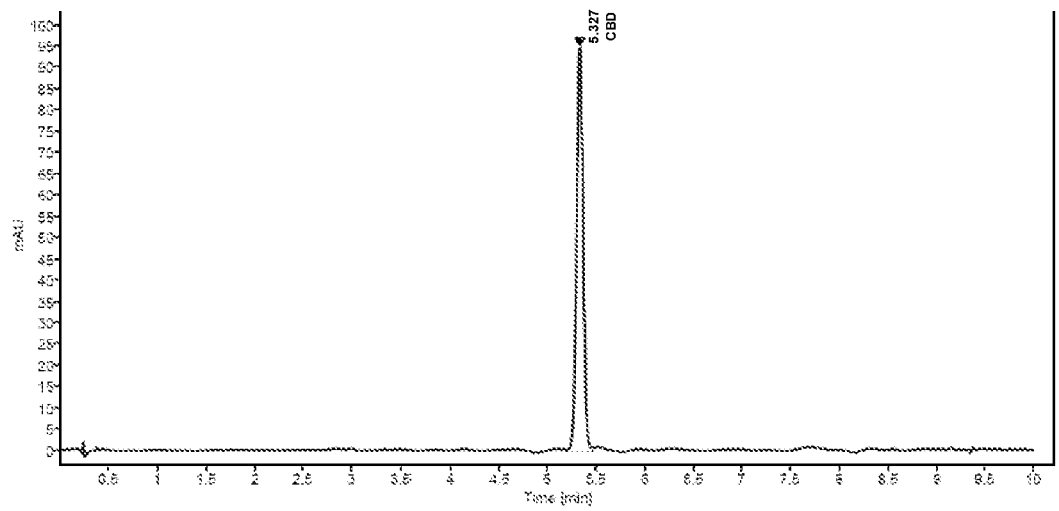
FIG. 11C is an HPLC chromatogram showing the cannabinoid content of a decarboxylated CBD oil recovered from the purified CBDA-TPA salt shown in FIG. 11B.
Figure 12C:
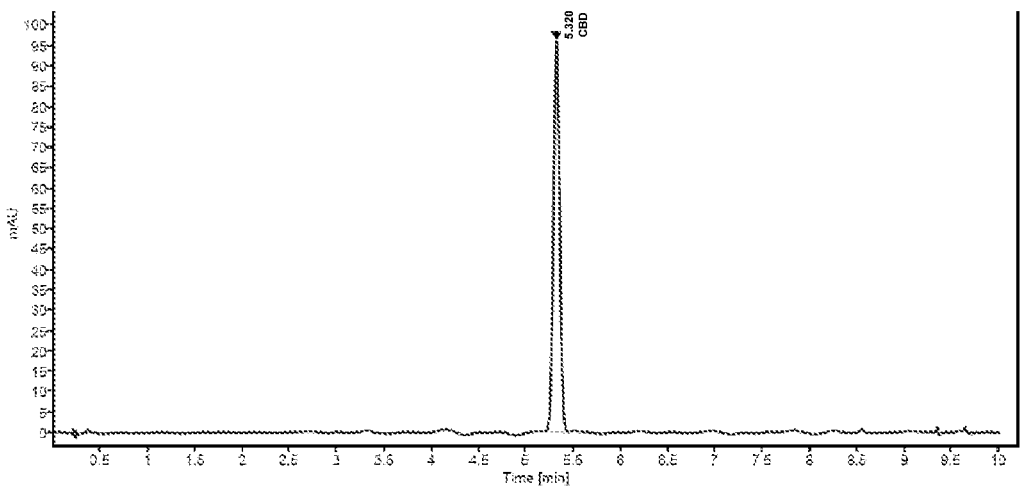
FIG. 12C is an HPLC chromatogram showing the cannabinoid content of a decarboxylated CBD oil recovered from the purified CBDA-DMEA salt shown in FIG. 12B.
Figure 13C:
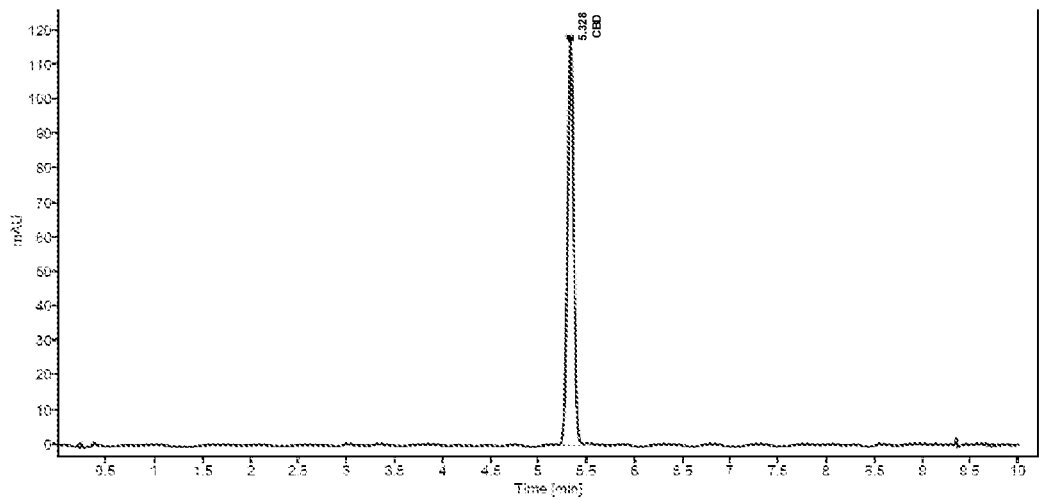
FIG. 13C is an HPLC chromatogram showing the cannabinoid content of a decarboxylated CBD oil recovered from the purified CBDA-piperidineethanol salt shown in FIG. 13B.
Figure 14C:
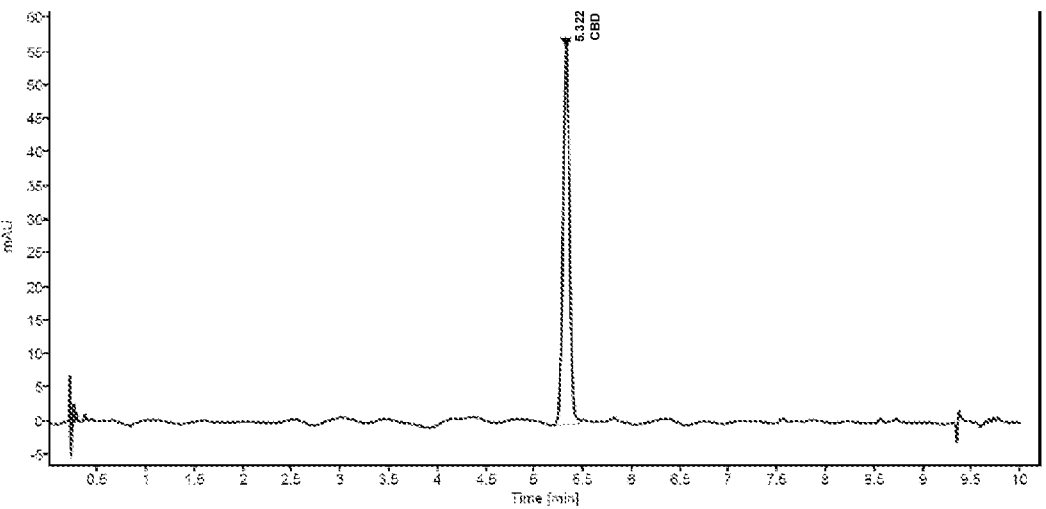
FIG. 14C is an HPLC chromatogram showing the cannabinoid content of a decarboxylated CBD oil recovered from the purified CBDA-DABCO salt shown in FIG. 14B.
Figure 15C:
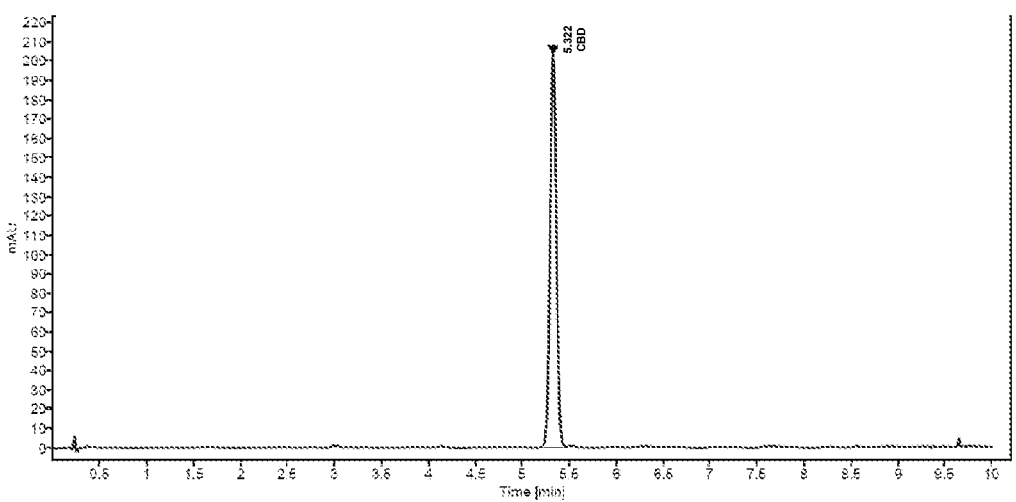
FIG. 15C is an HPLC chromatogram showing the cannabinoid content of a decarboxylated CBD oil recovered from the purified CBDA-TMEDA salt shown in FIG. 15B.
Figure 16C:
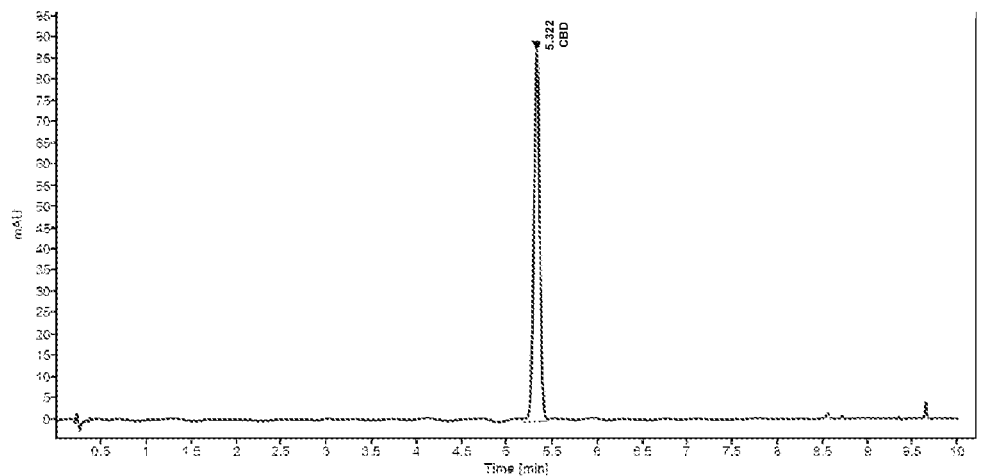
FIG. 16C is an HPLC chromatogram showing the cannabinoid content of a decarboxylated CBD oil recovered from the purified CBDA-quinine salt shown in FIG. 16B.
Figure 17C:
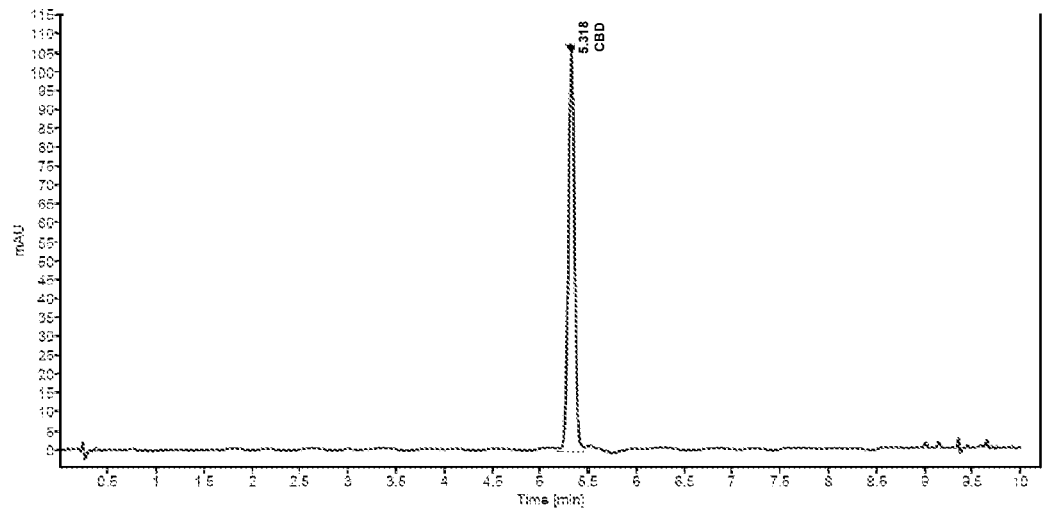
FIG. 17C is an HPLC chromatogram showing the cannabinoid content of a decarboxylated CBD oil recovered from the purified CBDA-DBU salt shown in FIG. 17B.
Figure 18C:
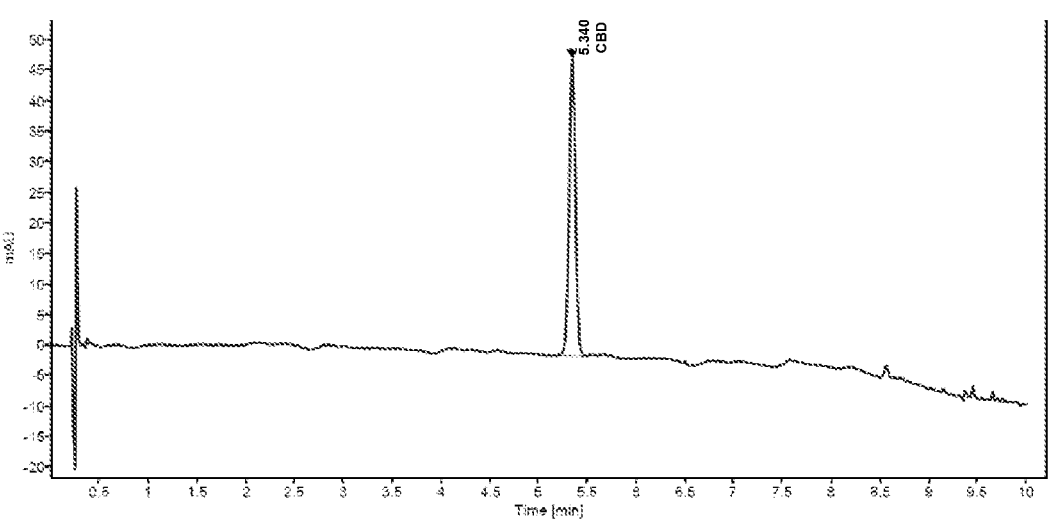
FIG. 18C is an HPLC chromatogram showing the cannabinoid content of a decarboxylated CBD oil recovered from the purified CBDA-DBN salt shown in FIG. 18B.

Each of the purified CBDA-amine salts were decarboxylated by the addition of 10:1 volume/mass of a 2.5% $Na_2CO_3$ solution followed by heating the reaction mixtures to refluxing conditions (about 100° C.±3° C.) for 4 hours. After the 4-hour decarboxylation period, the resulting biphasic solution consisting of a lower aqueous layer and an upper organic oil layer containing decarboxylated CBD and the amine, was cooled to about 70° C. Then, the CBD and amine contained in the upper organic layer were solubilized in a 1:1 v/v ratio of heptane to the $Na_2CO_3$ solution. The upper organic layer was separated from the aqueous layer, then washed twice with a 1:1 v/v ratio of 5% HCl solution, and then dried over magnesium sulfate. The heptane was then removed from the organic layer by distillation to produce oils containing highly pure CBD (Table 22; FIG. 10D, purified CBD oil from TBA; FIG. 11C, purified CBD oil from TPA; FIG. 12C, purified CBD oil from DMEA; FIG. 13C, purified CBD oil from piperidineethanol; FIG. 14C, purified CBD oil from DABCO; FIG. 15C, purified CBD oil from TMEDA; FIG. 16C, purified CBDA oil from quinine; FIG. 17C, purified CBD oil from DBU; FIG. 18C, purified CBDA oil from DBN).

Example 13

This study assessed the precipitation and recrystallization of a crude CBDA-amine salt from a hemp crude extract from which the solvent had been removed to produce a concentrated resin, and then re-solubilized and standardized in denatured ethanol prior to addition of the amine.

Figure 19A:
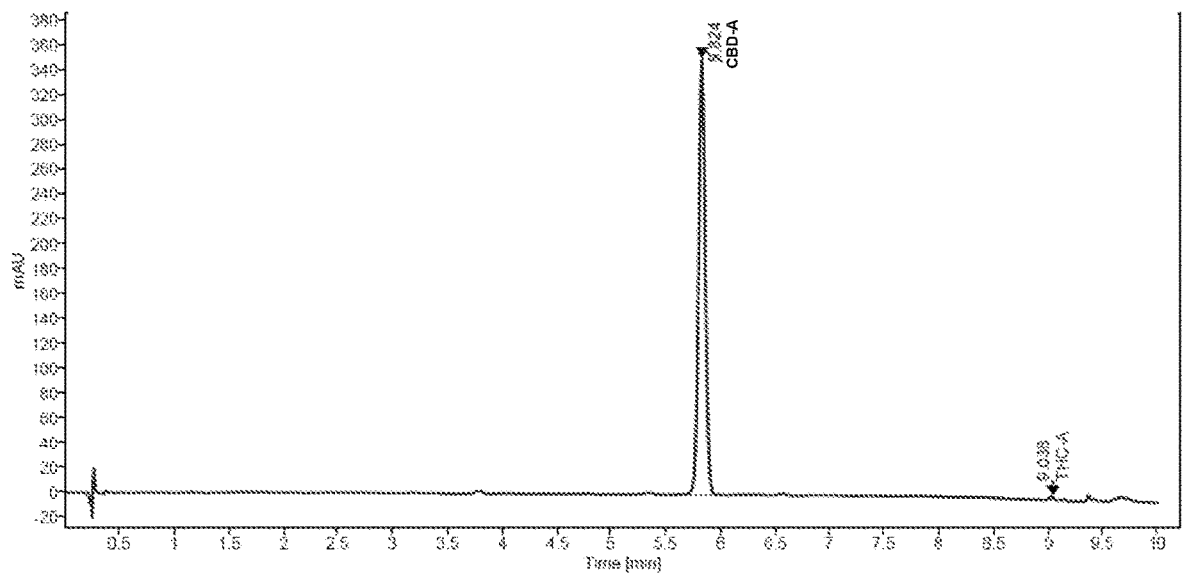
FIG. 19A is an HPLC chromatogram showing separation of cannabinoid phytochemicals from a hemp plant biomass sample in Example 13.
Figure 19B:
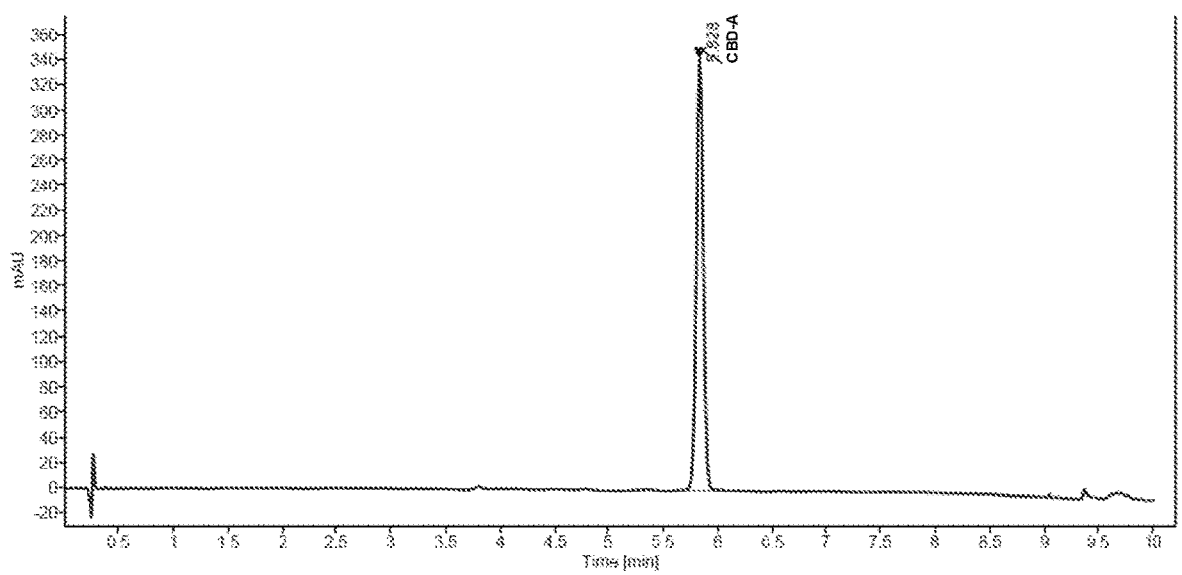
FIG. 19B is an HPLC chromatogram showing the cannabinoid phytochemical content of a crude CBDA-triethylamine salt precipitated from the crude hemp extract sample shown in FIG. 19A.
Figure 20A:
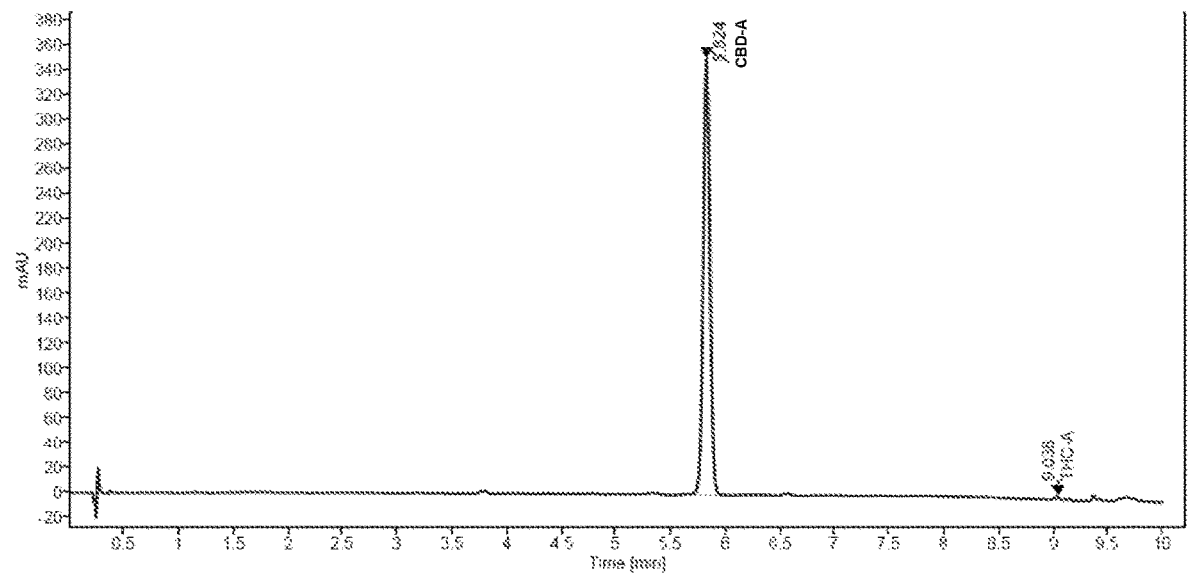
FIG. 20A is an HPLC chromatogram showing the cannabinoid phytochemical content of a crude CBDA-triethylamine salt precipitated from the crude hemp extract sample shown in FIG. 19A.

A stock solution of a crude hemp extract was prepared and standardized to contain 29.278 mg/ml CBDA (FIG. 19A). Then, a 30-ml aliquot of the hemp heptane-standardized hemp stock solution was evaporated by distillation and the resulting hemp resin was re-dissolved in 30 ml of a denatured ethanol (84.15% v/v ethanol, 15% v/v methanol, 0.85% v/v ethyl acetate) to produce a standardized stock solution of hemp extract in ethanol (FIG. 19B). Next, a 3:1 molar ratio of triethylamine (TEA) (1.17 ml) was added to the ethanol-standardized hemp stock solution after which, the mixture was vortexed for 20 seconds and placed in a −20° C. for 72 hr thereby producing a crude CBDA-TEA salt. Then, the crude CBDA-TEA salt was washed with 30 ml cold heptane, separated from the liquid phase by vacuum filtration, and dried. A sample of the dried crude CBDA-TEA salt was solubilized in methanol and assayed by HPLC (FIG. 20A). The dried crude CBDA-TEA salt was recrystallized by first, dissolution in a 10:1 volume/mass ratio of ethyl acetate, then spiked with a 1.5% v/v heptane antisolvent under refluxing conditions at about 77° C. 1. 3° C. for about 5 min after which, the solution was cooled under ambient conditions to about 30° C. thereby initiating recrystallization. The recrystallizing solution was further cooled to 4° C. overnight. The recrystallized CBDA amine salt was then separated from the liquid phase by vacuum filtration, re-slurried with a 3:1 volume/mass ratio cold heptane, recovered by filtration, dried under vacuum, and analyzed by HPLC (FIG. 20B).

Figure 20B:
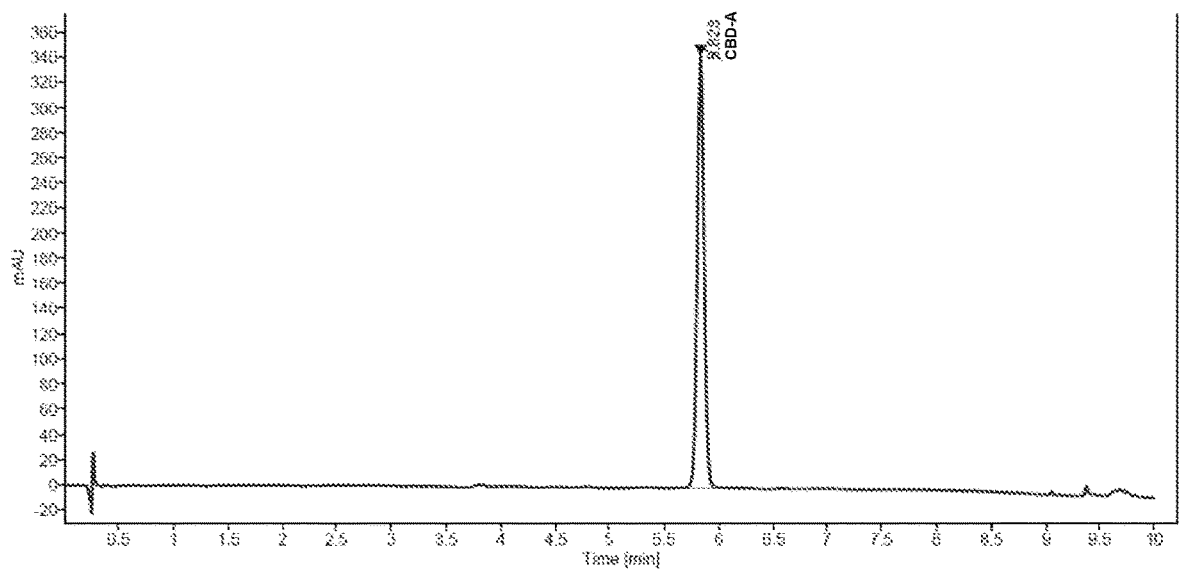
FIG. 20B is an HPLC chromatogram showing the cannabinoid phytochemical content of a purified CBDA-triethylamine salt recrystallized from the crude CBDA-triethylamine salt shown in FIG. 20A.

The results demonstrate that precipitation of a crude CBDA-TEA salt from an ethanol-standardized hemp stock solution (FIG. 20A), and then solubilizing and recrystallizing the CBDA-TEA salt produced a highly purified CBDA-TEA salt (FIG. 20B).

Example 14

This study assessed the effects of spiking a standardized solvent-solubilized crude hemp extract with denatured alcohol or acetone of the precipitation and recrystallization of a crude CBDA-amine salt.

The standardized heptane-solubilized hemp stock solution containing 29.278 mg/ml of CBDA prepared for the study disclosed in EXAMPLE 13 (FIG. 19A) was also used in this study. A first 30 ml-aliquot of the standardized heptane-solubilized hemp stock solution was spiked with 1.05 ml of denatured ethanol (84.15% v/v ethanol, 15% v/v methanol, 0.85% v/v ethyl acetate) to produce a 3.38% v/v ethanol-spiked hemp stock solution. A second 30 ml-aliquot of the heptane-solubilized hemp stock solution was spiked with 1.5 ml acetone to produce a 4.76% v/v acetone-spiked heptane-solubilized hemp stock solution.

Figure 21A:
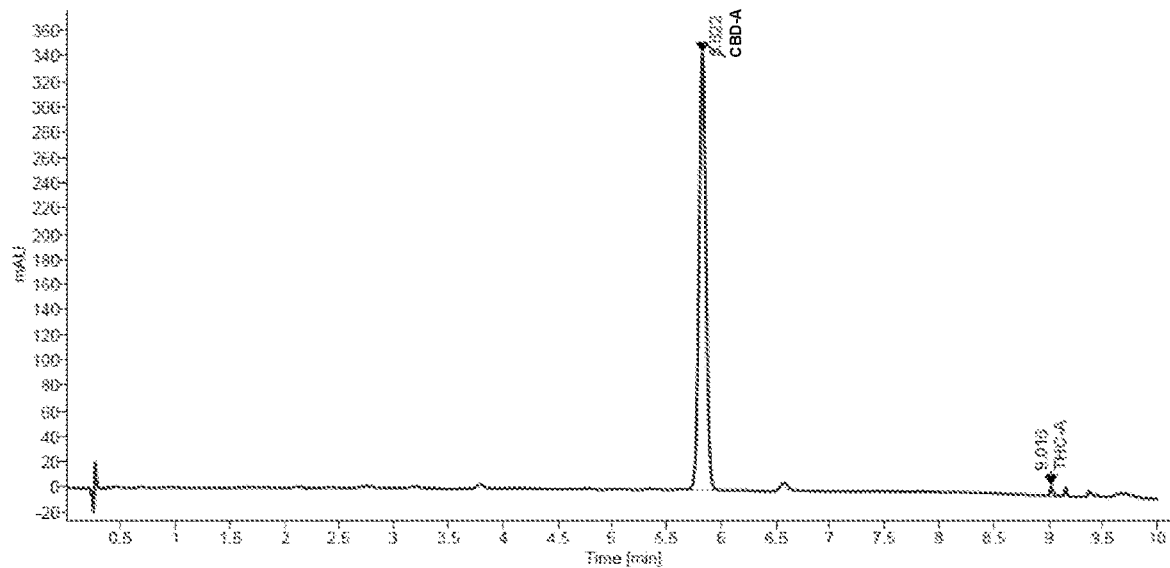
FIG. 21A is an HPLC chromatogram showing the cannabinoid phytochemical content of a crude CBDA-triethylamine salt precipitated from the crude hemp extract sample shown in FIG. 19A that received a spike of denatured ethanol prior to the addition of the triethylamine solution.
Figure 22A:
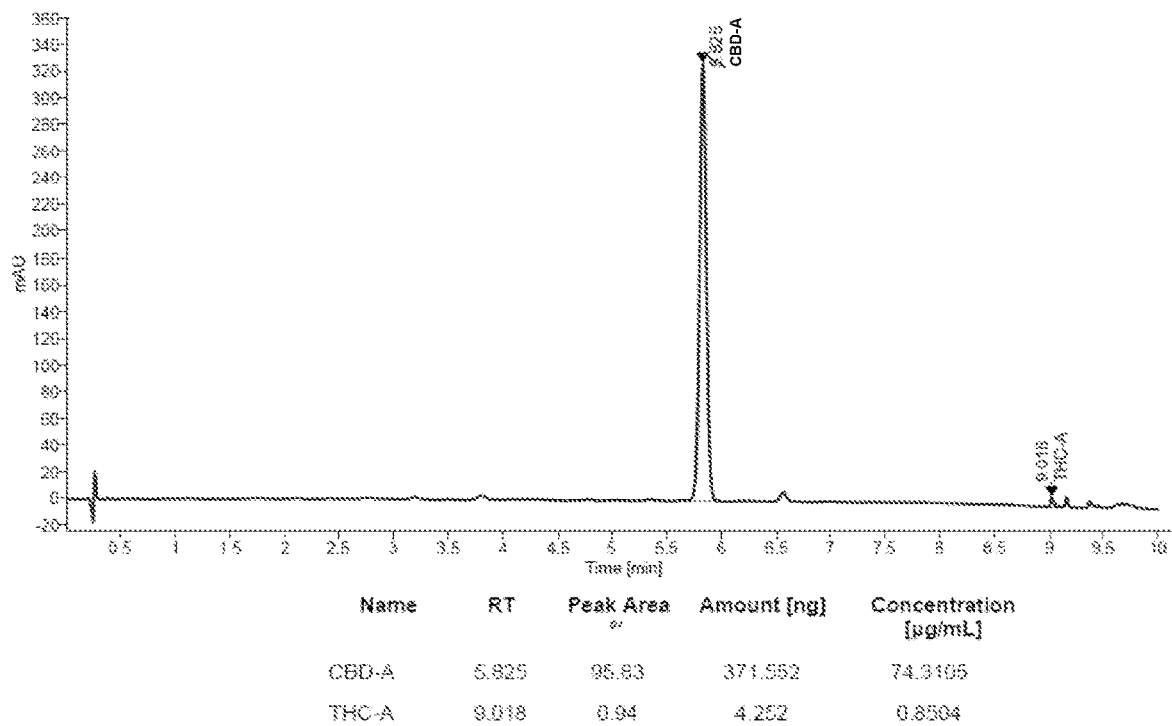
FIG. 22A is an HPLC chromatogram showing the cannabinoid phytochemical content of a crude CBDA-triethylamine salt precipitated from the crude hemp extract sample shown in FIG. 19A that received a spike of acetone prior to the addition of the triethylamine solution.

Next, a 3:1 molar ratio of triethylamine (1.17 ml) was added to each 30 ml-spiked hemp stock solution. The mixtures were vortexed for 20 seconds thereby precipitating crude CBDA-TEA salts. The crude CBDA-TEA salts were washed with 30 ml cold heptane (4° C.), then separated from the liquid phase by vacuum filtration, and dried. Samples of the dried crude CBDA-TEA salt was solubilized in methanol and assayed by HPLC. The HPLC data for the crude CBDA-TEA salt recovered from the ethanol-spiked heptane-solubilized hemp stock solution are shown in FIG. 21A. The HPLC data for the crude CBDA-TEA salt recovered from the acetone-spiked heptane-solubilized hemp stock solution are shown in FIG. 22A.

Figure 21B:
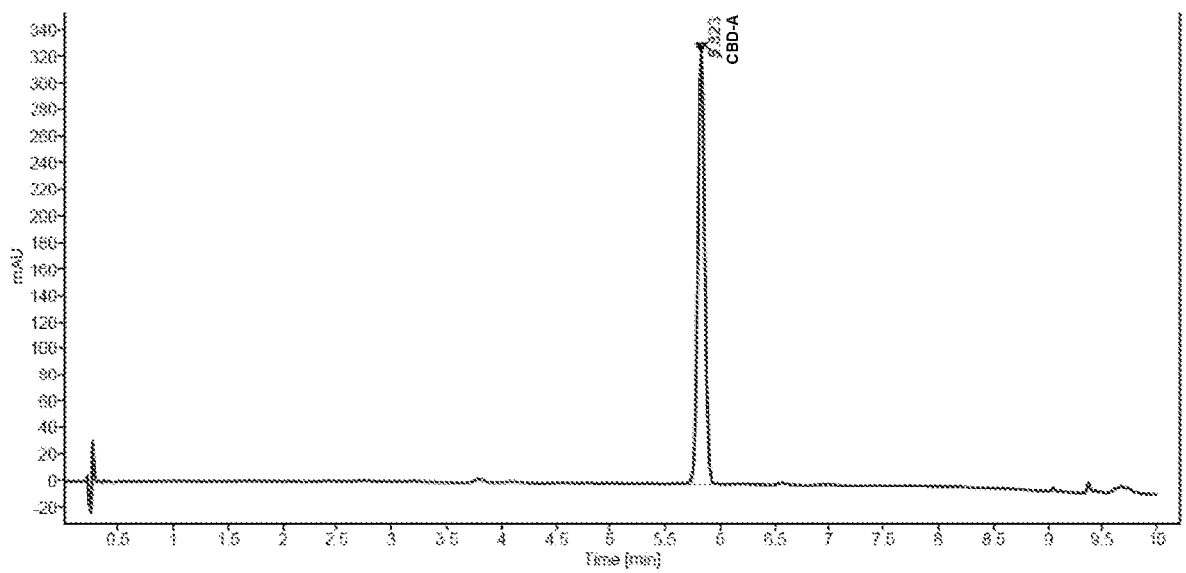
FIG. 21B is an HPLC chromatogram showing the cannabinoid phytochemical content of a purified CBDA-triethylamine salt recrystallized from the crude CBDA-triethylamine salt shown in FIG. 21A.
Figure 22B:
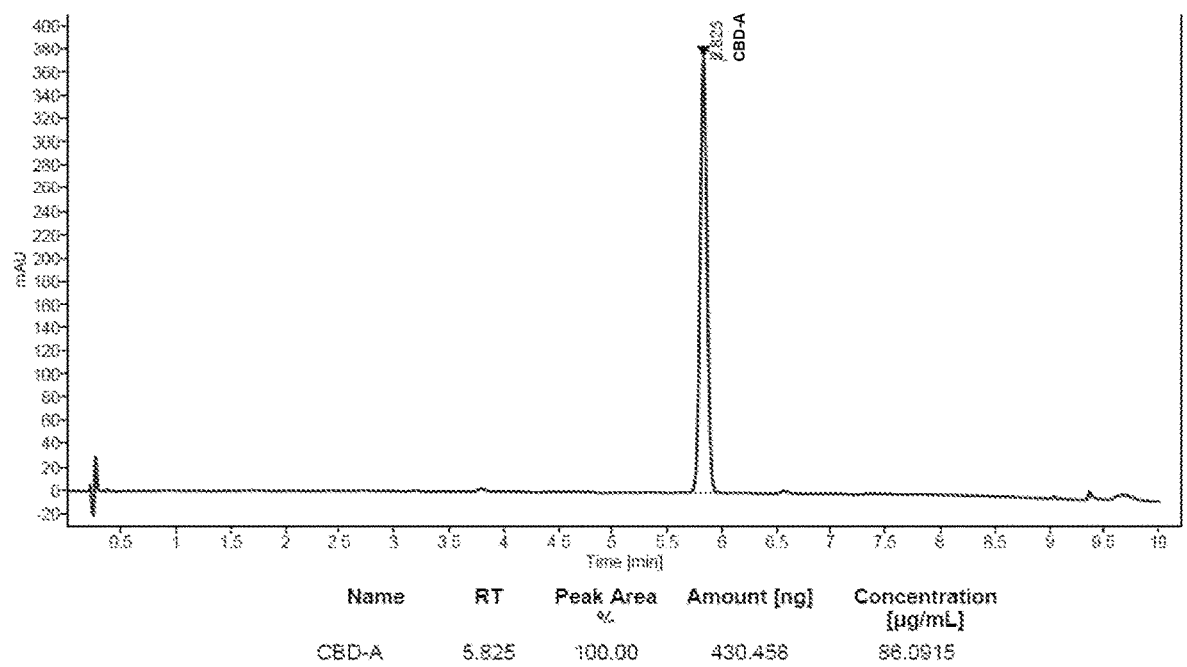
FIG. 22B is an HPLC chromatogram showing the cannabinoid phytochemical content of a purified CBDA-triethylamine salt recrystallized from the crude CBDA-triethylamine salt shown in FIG. 22A.

The dried crude CBDA-TEA salts were then recrystallized by first, dissolution in a 10:1 volume/mass ratio of ethyl acetate spiked with 1.5% v/v heptane antisolvent and then heating at refluxing conditions about 77° C.±3° C. for 5 min after which, the mixtures were cooled under ambient conditions to about 30° C., and then stored at 4° C. overnight for about 18 hr. The recrystallized purified CBDA-TEA salts were separated from their liquid phases by vacuum filtration, then re-slurried with a 3:1 volume/mass ratio cold heptane (4° C.), recovered by vacuum filtration, dried under vacuum, and then analyzed by HPLC. The purified CBDA-TEA salts (recovered from the ethanol-spiked heptane-solubilized hemp stock solution are shown in FIG. 21B, and the HPLC data for the purified CBDA-TEA salt recovered from the acetone-spiked heptane-solubilized hemp stock solution are shown in FIG. 22B.

Example 15

This study assessed the effects of decarboxylation of a purified CBDA-triethylamine (TEA) salt in a 10% $Na_2CO_3$ solution.

Figure 23A:
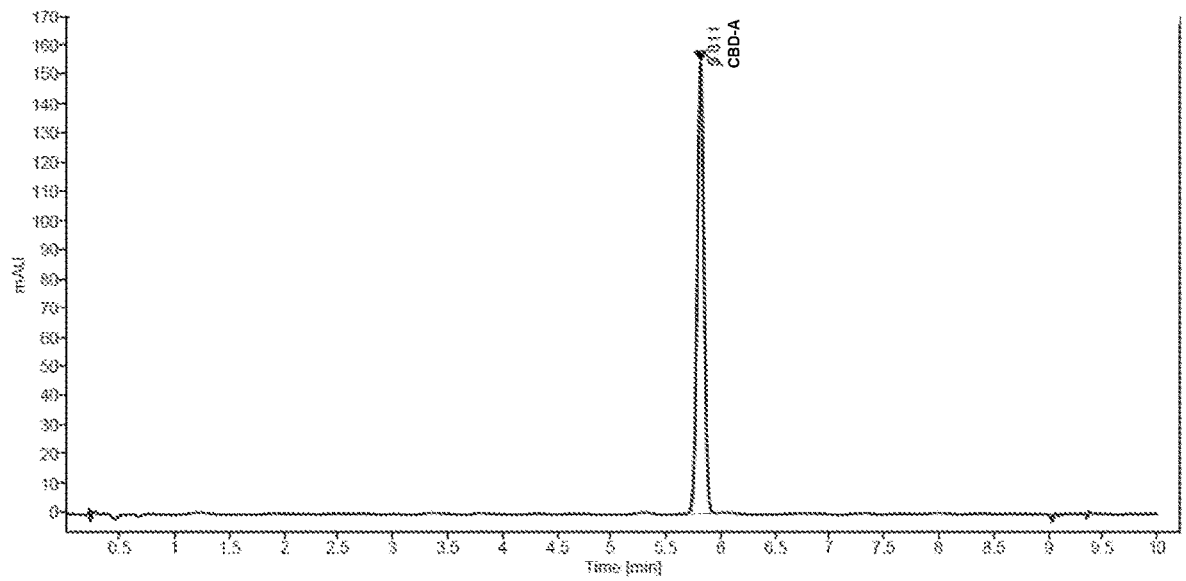
FIG. 23A is an HPLC chromatogram showing the cannabinoid phytochemical content of a purified crystalline CBDA-triethylamine salt from Example 15 prior to decarboxylation in a 10% $Na_2CO_3$ solution.
Figure 23B:
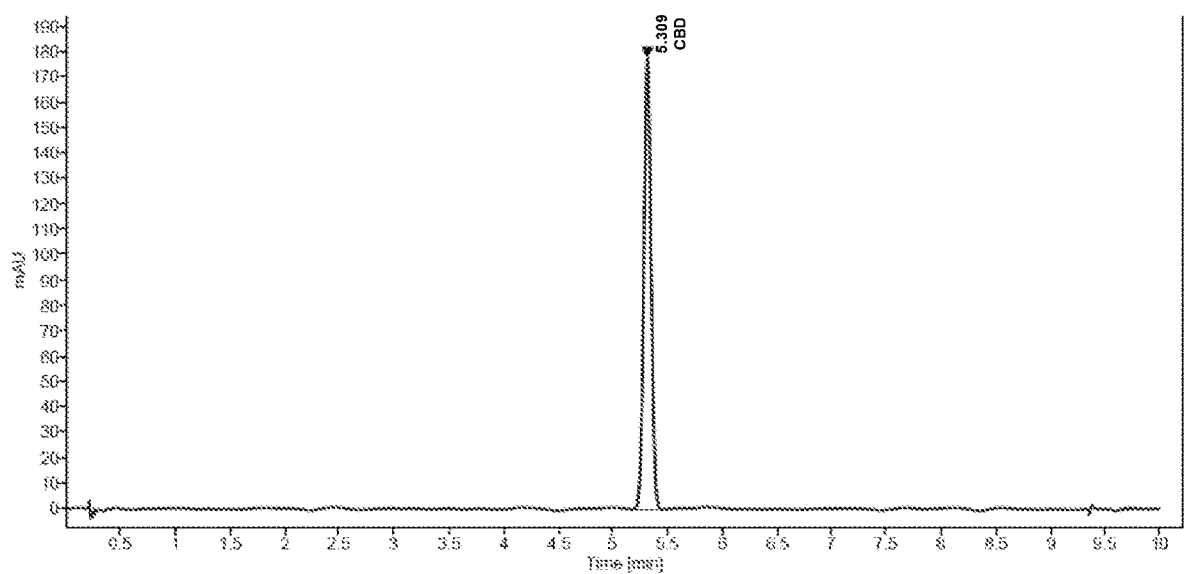
FIG. 23B is an HPLC chromatogram showing the composition of a purified CBD produced from the crystalline CBDA-triethylamine salt shown in FIG. 23A.

5.5857 grams of a crystalline purified CBDA-TEA salt (HPLC analysis shown in FIG. 23A) was added to a 2.5:1 volume/mass ratio of a 10% $Na_2CO_3$ solution (14 ml) and heated at refluxing conditions (about 100° C.±3° C.) for 4 hr under nitrogen atmosphere. After the 4-hr decarboxylation period, the crystalline CBDA-TEA produced a biphasic solution consisting of an upper organic oil layer and lower aqueous layer. The biphasic solution was cooled to about 70° C. and the decarboxylated CBD and amine contained in the upper organic layer were solubilized in 120 ml heptane. The organic layer was then separated from the aqueous layer, washed with 60 ml of a 5% HCl solution, and dried over magnesium sulfate. The heptane was then removed from the organic layer by distillation to thereby produce 3.8043 grams of an oil containing highly pure CBD (FIG. 23B).

Example 16

This study assessed the effects of solubilizing a crude CBDA-triethylamine (TEA) salt in two selected mass/volume ratios of a denatured ethanol and then adding different volumes of distilled $H_2O$ as the antisolvent, on the yield and purity of the purified CBDA-TEA salt produced.

Figure 24A:
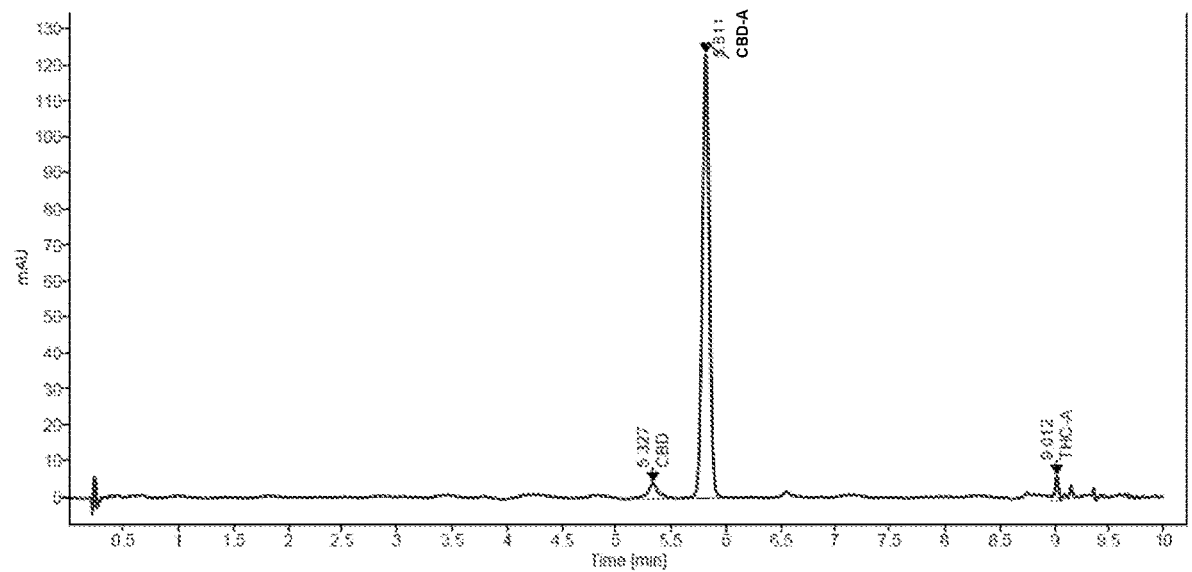
FIG. 24A is an HPLC chromatogram showing the cannabinoid phytochemical content of a crude CBDA-triethylamine salt used as a starting material in Example 17.

About 1-g amounts of a solid crude CBDA-TEA salt (HPLC analysis shown in FIG. 24A) were fully dissolved in 10:1 or 7:1 volume/mass ratios of denatured ethanol (Table 23) and then refluxed at about 75° C.±3° C. for about 5 min. The mixtures were then cooled to ambient condition and then, selected volumes of distilled $H_2O$ (Table 23) were added and mixed into the cooled mixtures thereby initiating recrystallization of a purified CBDA-TEA salt, and then were placed into 4° C. for about 16 hr. The recrystallized purified CBDA-TEA salts were separated from their liquid phases by vacuum filtration, dried and then analyzed by HPLC.

TABLE 23

| FIG. # | dEtOH (ml) | $dH_2O$ (ml) | % $dH_2O$ | Crude CBDA-TEA (g) | Purified CBDA-TEA (g) | % yield |
|---|---|---|---|---|---|---|
| 24B | 10 | 0 | 0 | 0.997 | 0.699 | 70.1% |
| 24C | 10 | 0.1 | 0.99% | 1.069 | 0.731 | 68.3% |
| 24D | 10 | 0.5 | 4.76% | 1.010 | 0.685 | 67.8% |
| 24E | 7 | 1.75 | 20.0% | 1.017 | 0.722 | 71.1% |
| 24F | 7 | 3.5 | 33.3% | 1.059 | 0.577 | 54.5% |
| 24G | 7 | 7 | 50.0% | 0.996 | 0.850 | 85.4% |
| 24H | 7 | 0 | 0 | 1.009 | 0.737 | 73.1% |

Example 17

Figure 24B:
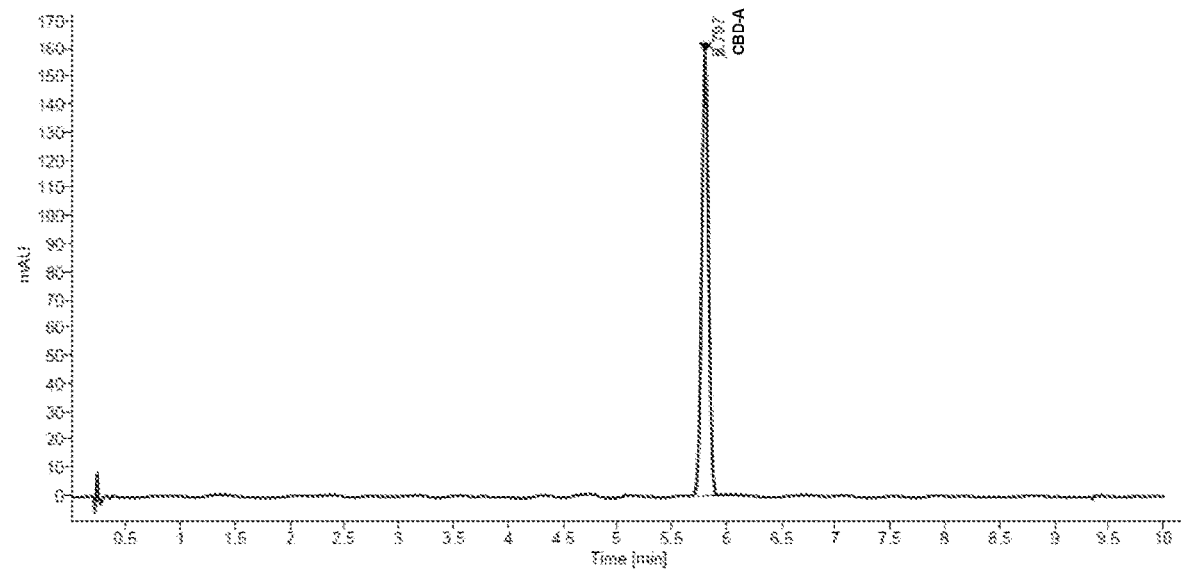
FIG. 24B is an HPLC chromatogram showing the cannabinoid composition of a crystalline purified CBDA-triethylamine salt produced from the crude CBDA-triethylamine salt shown in FIG. 24A by solubilization in hot denatured ethanol and recrystallized by cooling.
Figure 24C:
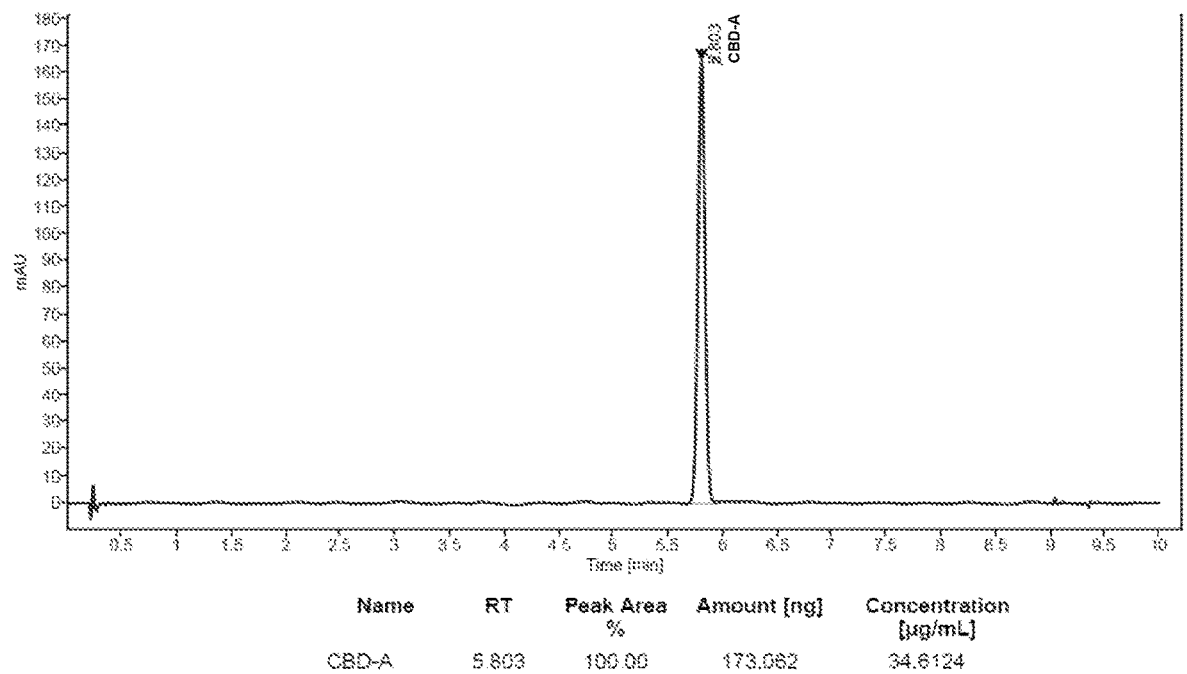
FIG. 24C is an HPLC chromatogram showing the cannabinoid composition of a crystalline purified CBDA-triethylamine salt produced from the crude CBDA-triethylamine salt shown in FIG. 24 by solubilization in hot denatured ethanol and recrystallized by cooling and a spike of 0.99% distilled $H_2O$.
Figure 24D:
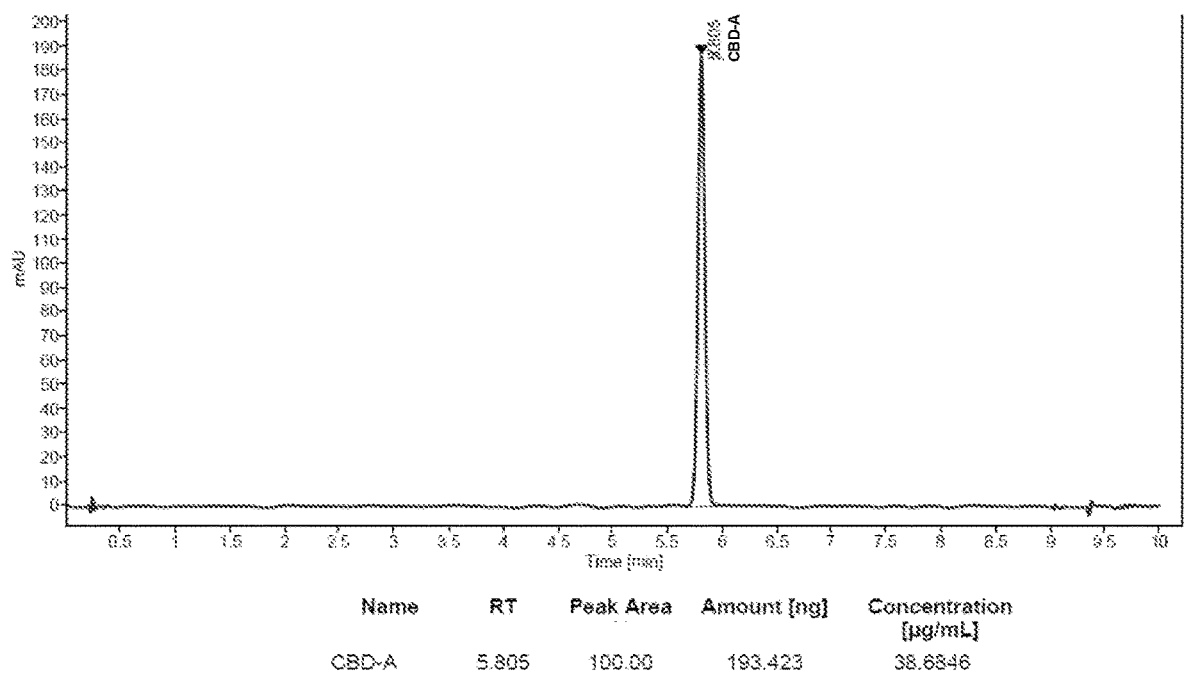
FIG. 24D is an HPLC chromatogram showing the cannabinoid composition of a crystalline purified CBDA-triethylamine salt produced from the crude CBDA-triethylamine salt shown in FIG. 24A by solubilization in hot denatured ethanol and recrystallized by cooling and a spike of 4.76% distilled $H_2O$.
Figure 24E:
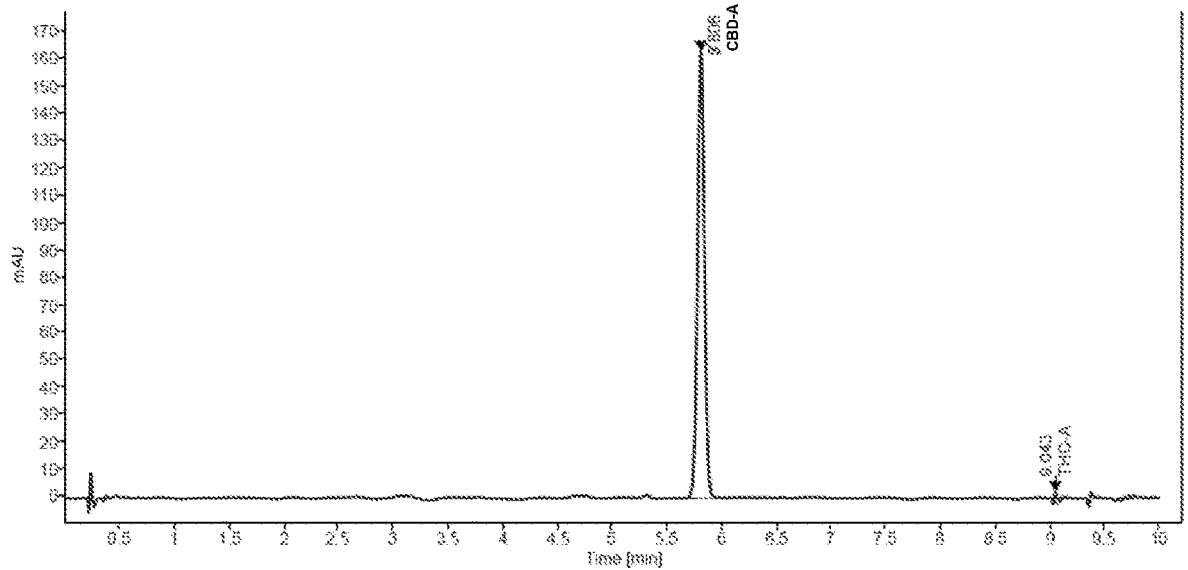
FIG. 24E is an HPLC chromatogram showing the cannabinoid composition of a crystalline purified CBDA-triethylamine salt produced from the crude CBDA-triethylamine salt shown in FIG. 24A by solubilization in hot denatured ethanol and recrystallized by cooling and a spike of 20% distilled $H_2O$.
Figure 24F:
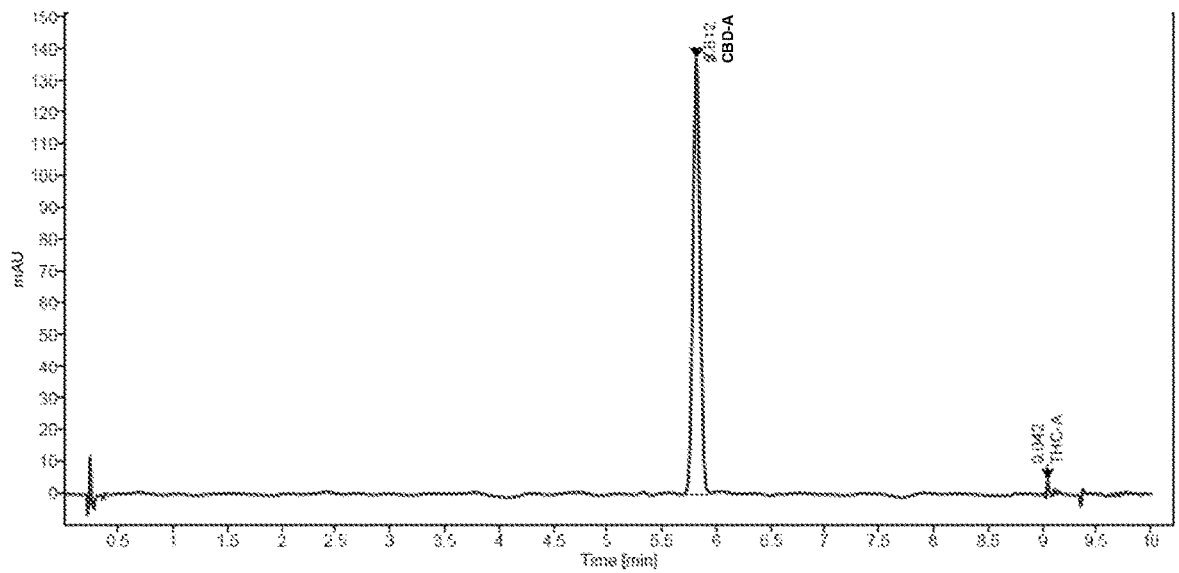
FIG. 24F is an HPLC chromatogram showing the cannabinoid composition of a crystalline purified CBDA-triethylamine salt produced from the crude CBDA-triethylamine salt shown in FIG. 24A by solubilization in hot denatured ethanol and recrystallized by cooling and a spike of 33.3% distilled $H_2O$.
Figure 24G:
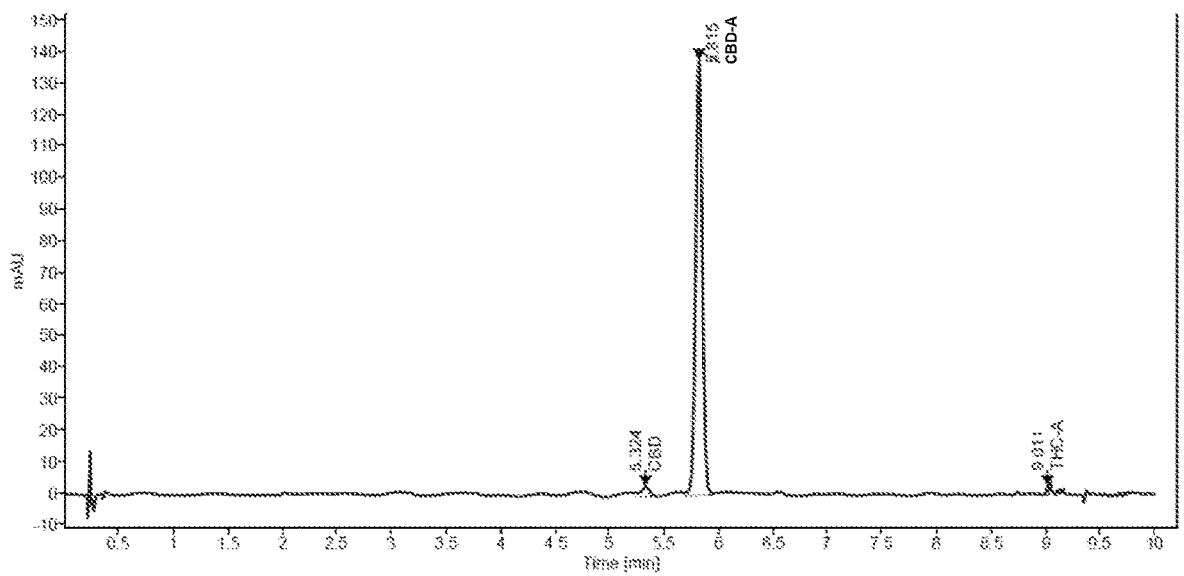
FIG. 24G is an HPLC chromatogram showing the cannabinoid composition of a crystalline purified CBDA-triethylamine salt produced from the crude CBDA-triethylamine salt shown in FIG. 24A by solubilization in hot denatured ethanol and recrystallized by cooling and a spike of 50% distilled $H_2O$.
Figure 24H:
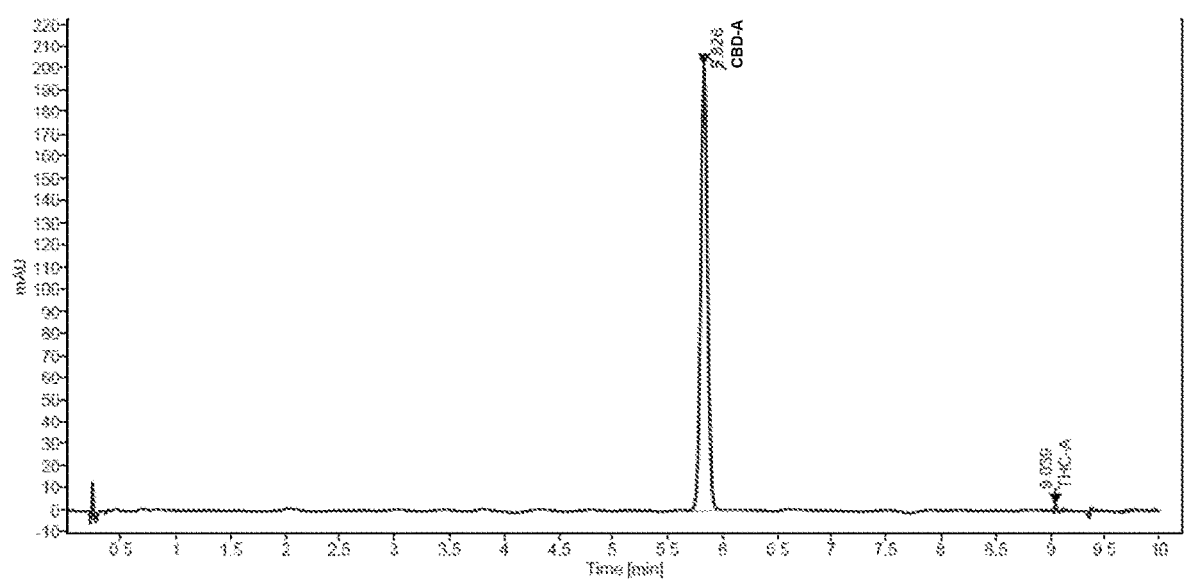
FIG. 24H is an HPLC chromatogram showing the cannabinoid composition of a crystalline purified CBDA-triethylamine salt produced from the crude CBDA-triethylamine salt shown in FIG. 24A by solubilization in hot denatured ethanol and recrystallized by cooling and a spike of 0% distilled $H_2O$.
Figure 25:
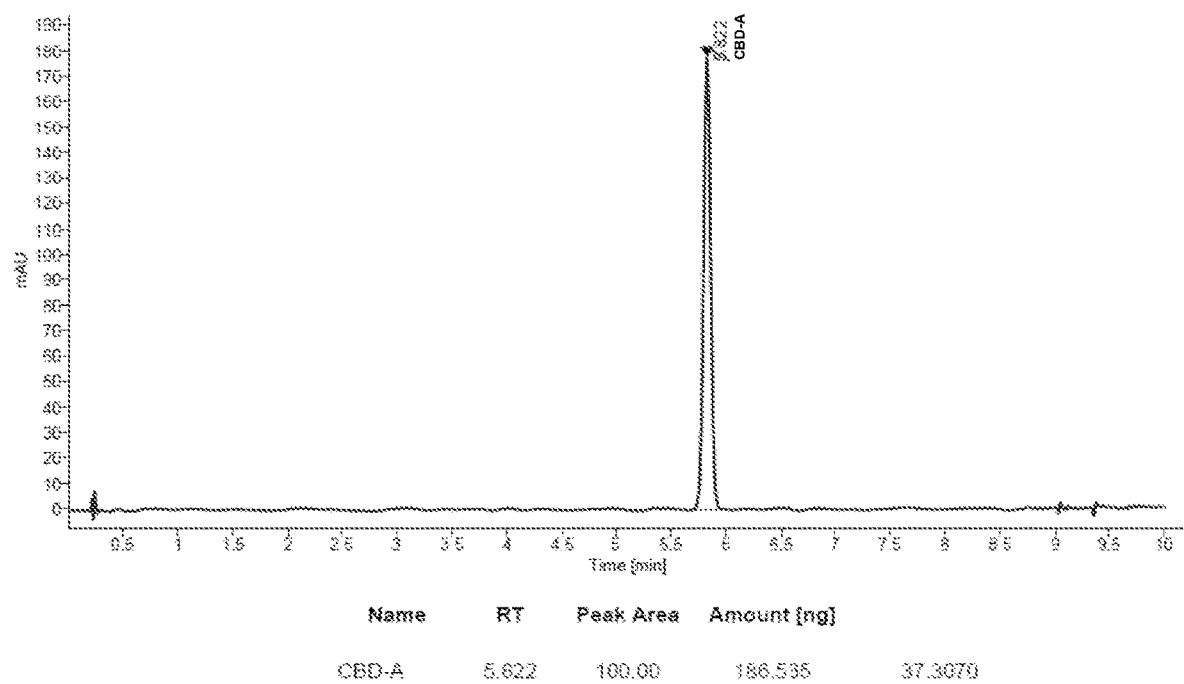
FIG. 25 is an HPLC chromatogram showing the composition of a decarboxylated purified CBD produced from the crystalline CBDA-triethylamine salts shown in FIGS. 24B, 24C, 24D.

Samples of three purified CBDA-TEA salts that were recrystallized from the crude CBDA-TEA salts by dissolution in a 10:1 molar ratio of denatured ethanol in Example 17 (shown in FIGS. 24A, 24B, 24C), were combined, mixed together, and then dissolved in a 6:1 volume/mass ratio of dichloromethane (12 ml). The resulting solution was acidified with 7 ml of a 5% HCl solution and mixed thoroughly thereby producing a biphasic solution. The lower aqueous layer containing the TEA-hydrochloride was separated from the organic layer containing the CBDA. The organic layer was dried over magnesium sulfate, then gravity filtered after which, the dichloromethane was removed by distillation, yielding 1.5249 grams of crystalline CBDA (FIG. 25).

Example 18

Figure 26A:
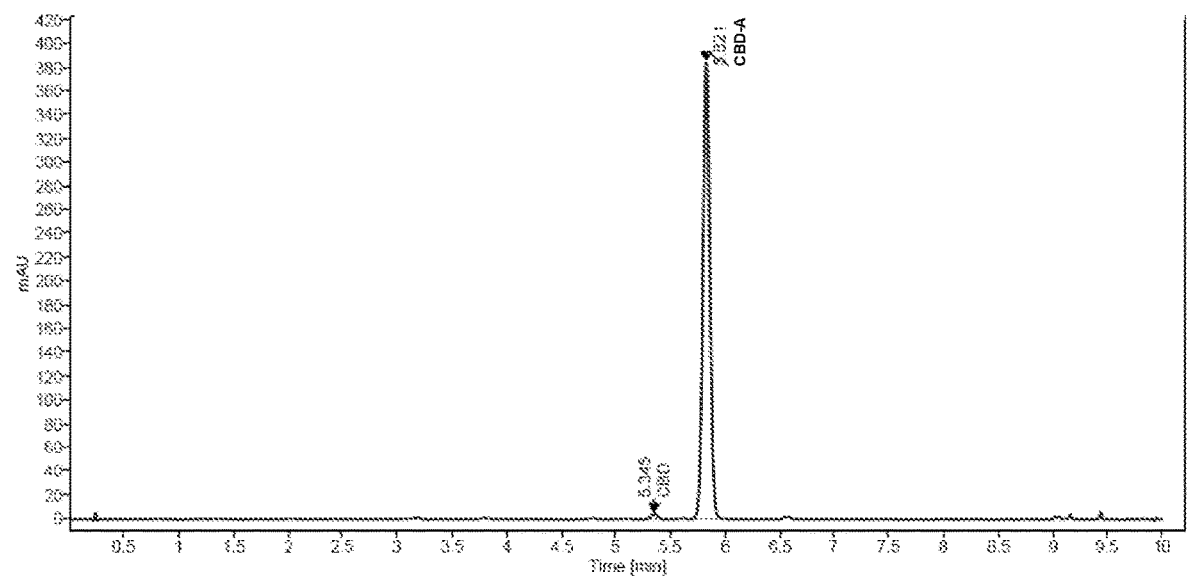
FIG. 26A is an HPLC chromatogram showing the cannabinoid phytochemical content of a crude CBDA-triethylamine salt used as a starting material in Example 19.

2.0637 g of a solid crude CBDA-TEA amine salt (HPLC analysis shown in FIG. 26A) was fully dissolved in a 3:1 volume/mass ratio of dichloromethane (6 ml) at about ambient temperature for about 5 min. The solution was cooled to 4° C. after which, 6 ml heptane were added to initiate recrystallization of a purified CBDA-TEA salt. The mixture was incubated at 4° C. for 1 hour and then at −20° C. overnight. The recrystallized purified CBDA amine salt was then separated from the liquid phase by vacuum filtration, washed with 25 ml cold heptane, dried under vacuum yielding 1.528 grams of white crystalline CBDA-TEA salt.

Figure 26B:
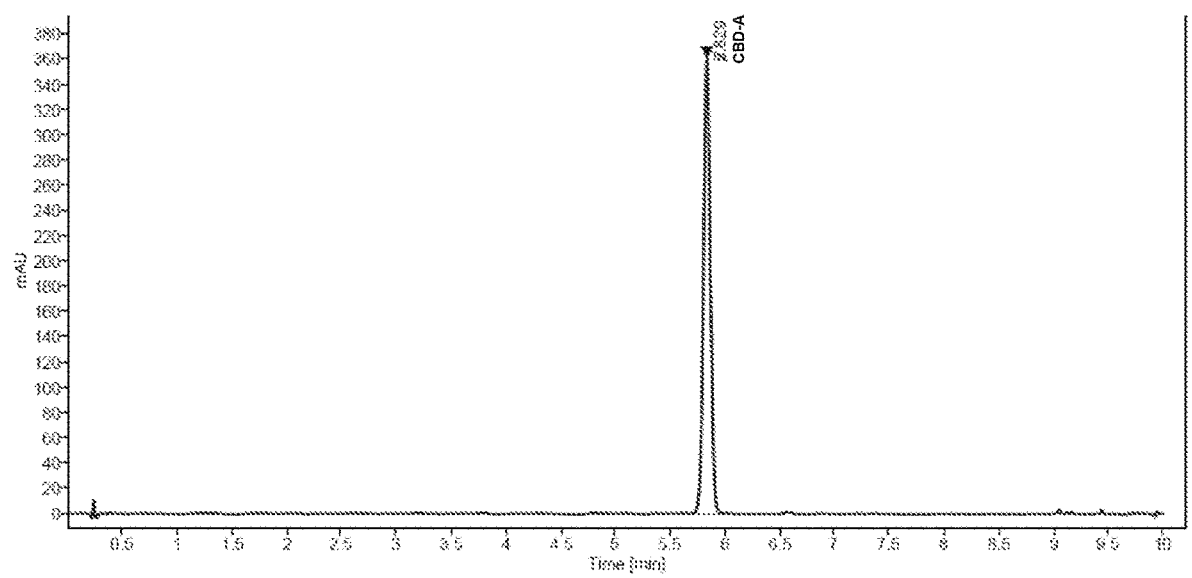
FIG. 26B is an HPLC chromatogram showing the cannabinoid composition of a crystalline purified CBDA-triethylamine salt produced from the crude CBDA-triethylamine salt shown in FIG. 26A by solubilization in warmed dichloromethane and recrystallized by cooling.

A sample of the recrystallized CBDA-TEA salt was dissolved in methanol and analyzed by HPLC (FIG. 26B).

Example 19

Figure 27A:
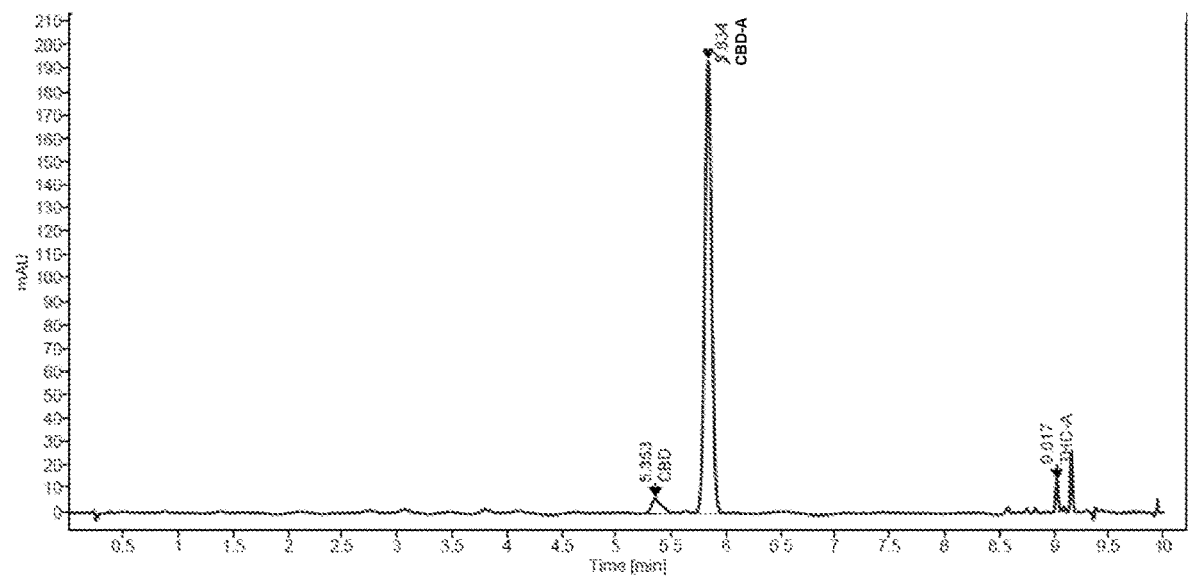
FIG. 27A is an HPLC chromatogram showing the cannabinoid composition of a standardized hemp extract stock used in Example 20.

406.4 grams of hemp biomass were ground to a powder and then commingled and mixed with 2.51 of heptane (6:1 mass/volume ratio) for 25 min at ambient temperature. The liquid phase was separated from the biomass by pressure filtration using nitrogen after which, the heptane was removed by distillation under vacuum to produce 40.3 grams of a CBDA-containing complex hemp extract resin. A standardized hemp extract stock solution was prepared by dissolving the hemp extract resin in 769.7 ml heptane to produce 811.57 ml of the standardized hemp extract stock solution. The standardized hemp extract stock solution was then spiked with 3.38% v/v ratio of a denatured ethanol (28.4 ml; 84.15% v/v ethanol, 15% v/v methanol, 0.85% v/v ethyl acetate). The CBDA content in the spiked standardized hemp extract stock solution was quantified by removing a 20-ul sample, separating the heptane under vacuum, dissolving the resulting resin in 1 ml of HPLC-grade methanol, and further preparing a 10× dilution of the sample in HPLC-grade methanol. The 10× diluted sample was then analyzed by HPLC and the standardized hemp extract stock was determined to contain 20.217 mg/ml of CBDA (FIG. 27A).

Figure 27B:
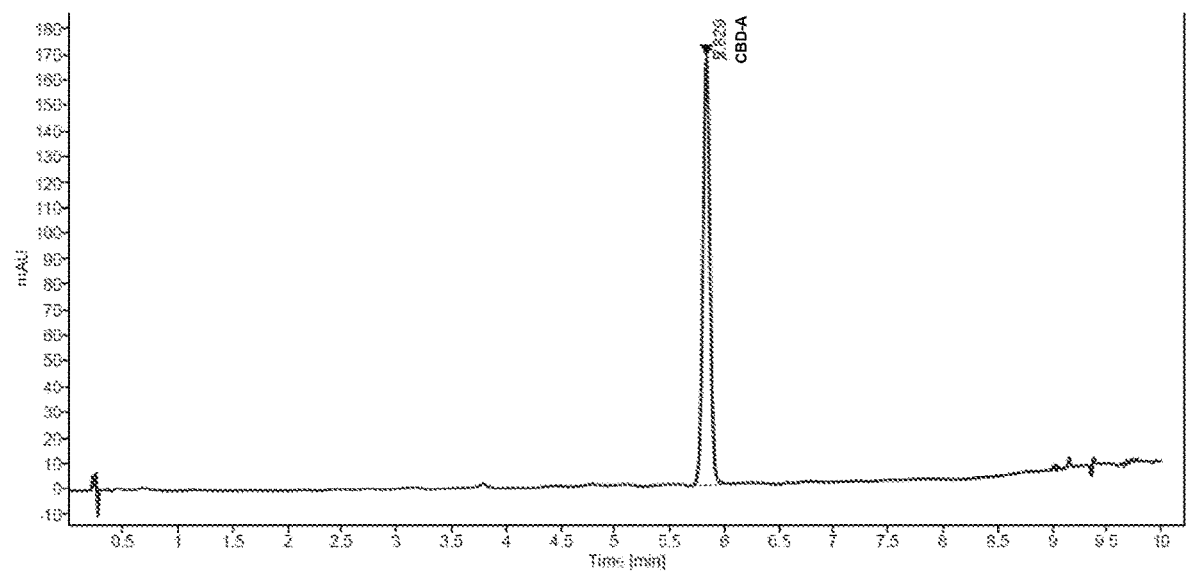
FIG. 27B is an HPLC chromatogram showing the cannabinoid content of a crude CBDA-triethylamine salt precipitated from the standardized hemp extract stock shown in FIG. 27A.

A 3:1 molar ratio of triethylamine (20.24 ml) was added dropwise to a 540-ml aliquot of the spiked standardized hemp extract stock solution while mixing with a magnetic stir bar, thereby causing precipitation of a crude CBDA-TEA salt. The solid crude CBDA-TEA salt was separated from the liquid phase by vacuum filtration, washed with 87 ml of cold heptane. The washed crude CBDA-TEA salt was re-slurried in 87 ml of cold heptane, then vacuum filtered and dried. The dried crude CBDA-TEA salt was analyzed by HPLC (FIG. 27B).

Figure 28A:
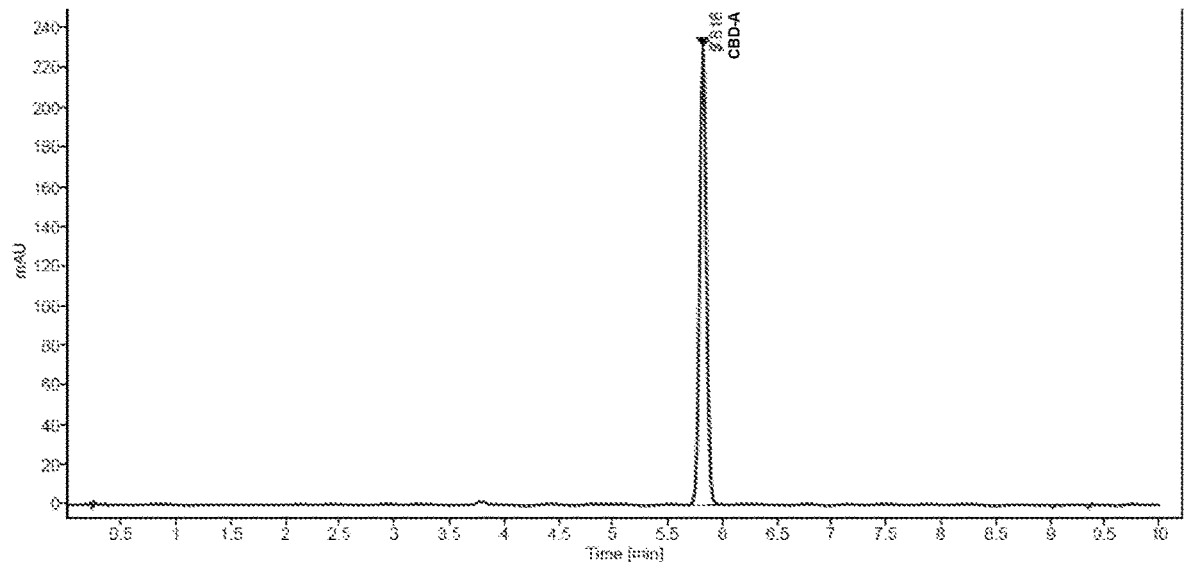
FIG. 28A is an HPLC chromatogram showing the cannabinoid content of a recrystallized purified CBDA-triethylamine salt precipitated from the crude CBDA-triethylamine salt shown in FIG. 27B.
Figure 28B:
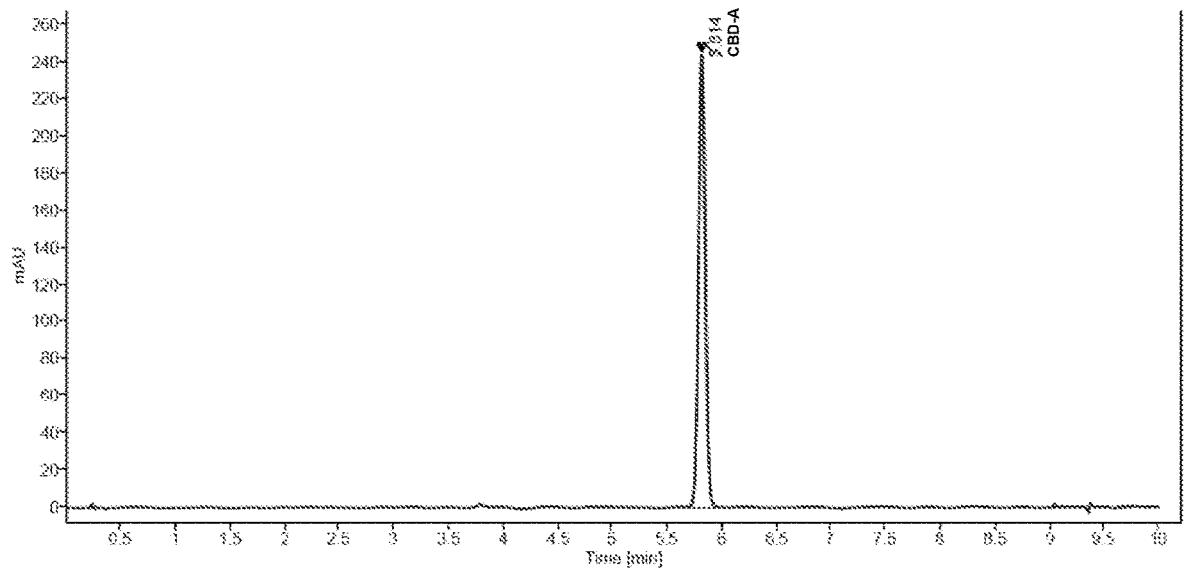
FIG. 28B is an HPLC chromatogram showing the cannabinoid content of a twice-recrystallized purified CBDA-triethylamine salt precipitated from the purified CBDA-triethylamine salt shown in FIG. 28A.

The washed and dried crude CBDA amine salt was then recrystallized by first, dissolution of 18.054 grams of the crude CBDA-TEA salt in a 10:1 volume/mass ratio of ethyl acetate (180.54 ml) spiked with 2.7 ml heptane under refluxing conditions (about 76° C. 3° C.) for about 15 min, and then cooled slowly under ambient conditions to about 30° C. at which temperature the precipitation of a solid purified CBDA-TEA salt increased rapidly. The recrystallizing solution was further cooled to and kept at 4° C. for about 16 hr. The recrystallized purified CBDA-TEA salt was then separated from the liquid phase by vacuum filtration, re-slurried with 54 ml cold heptane, filtered and dried under vacuum, and analyzed by HPLC (FIG. 28A). The recrystallized purified CBDA-TEA salt was recrystallized a second time by first, dissolving 15.595 g of the CBDA amine salt in 181 ml ethyl acetate spiked with 2.34 ml heptane under refluxing conditions (about 76° C. ° C.) for about 15 min, and then cooled slowly under ambient conditions to about 30° C. at which temperature the precipitation of a solid purified CBDA-TEA salt increased rapidly. The recrystallizing solution was further cooled to and kept at 4° C. for about 16 hr. The twice-recrystallized CBDA-TEA salt was then separated from the liquid phase by vacuum filtration, re-slurried with 54 ml cold heptane, filtered, and dried under vacuum, thereby yielding 14.299 grams of a highly purified CBDA-TEA amine salt. A sample of the twice-recrystallized purified salt was dissolved in methanol and analyzed by HPLC (FIG. 28B).

Figure 29:
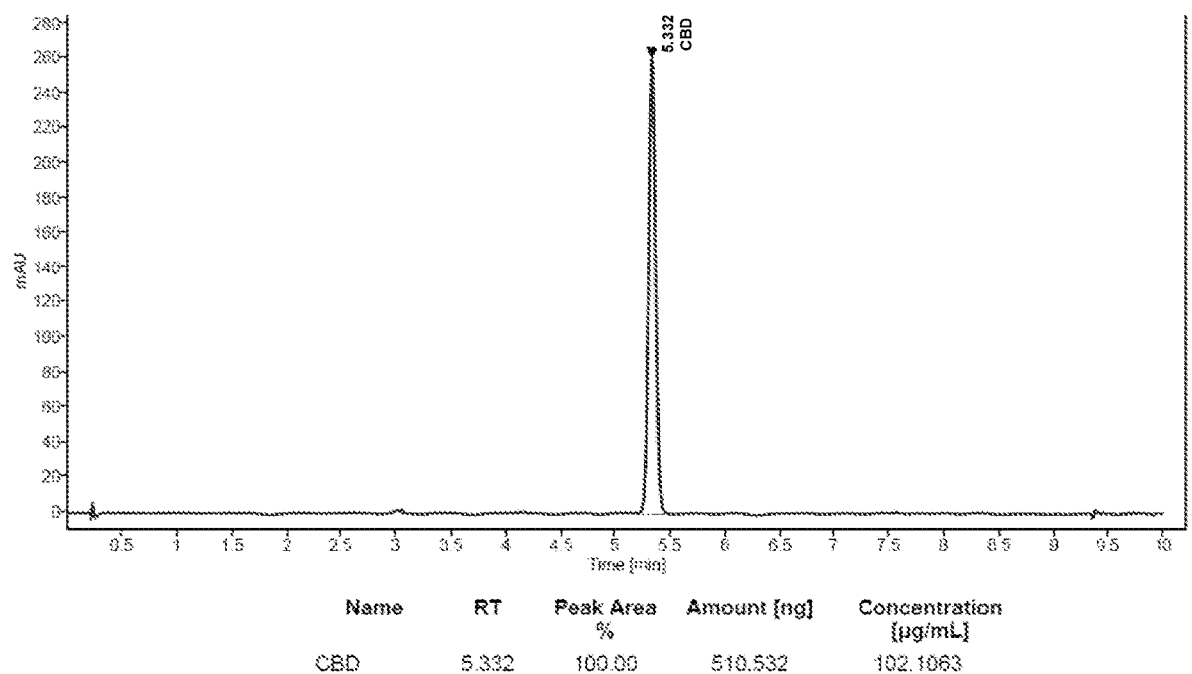
FIG. 29 is an HPLC chromatogram showing the cannabinoid content of a decarboxylated CBD oil recovered from the twice-recrystallized purified CBDA-triethylamine salt shown in FIG. 28B.

13.956 grams of the twice-recrystallized purified CBDA-TEA amine salt were decarboxylated by the addition of 10:1 volume/mass ratio of a 2.5% Na$_2$CO$_3$ solution (140 ml) followed by heating the reaction mixture at refluxing conditions (about 76° C.±3° C.) for 4 hours. After the 4-hour decarboxylation process, the resulting biphasic solution consisting of an upper organic oil layer containing decarboxylated CBD and the amine and a lower aqueous layer containing the 2.5% Na$_2$CO$_3$ solution, was cooled to 70° C. 40 ml of heptane were then added and mixed into the biphasic solution to solubilize thereinto the CBD and the amine. The upper organic layer was separated then recovered and washed three times with 140 ml of 5% HCl solution, then dried over magnesium sulfate. The heptane was then removed from the organic layer by distillation to thereby produce 8.932 grams of a highly purified CBD (FIG. 29).

Example 20

Figure 30A:
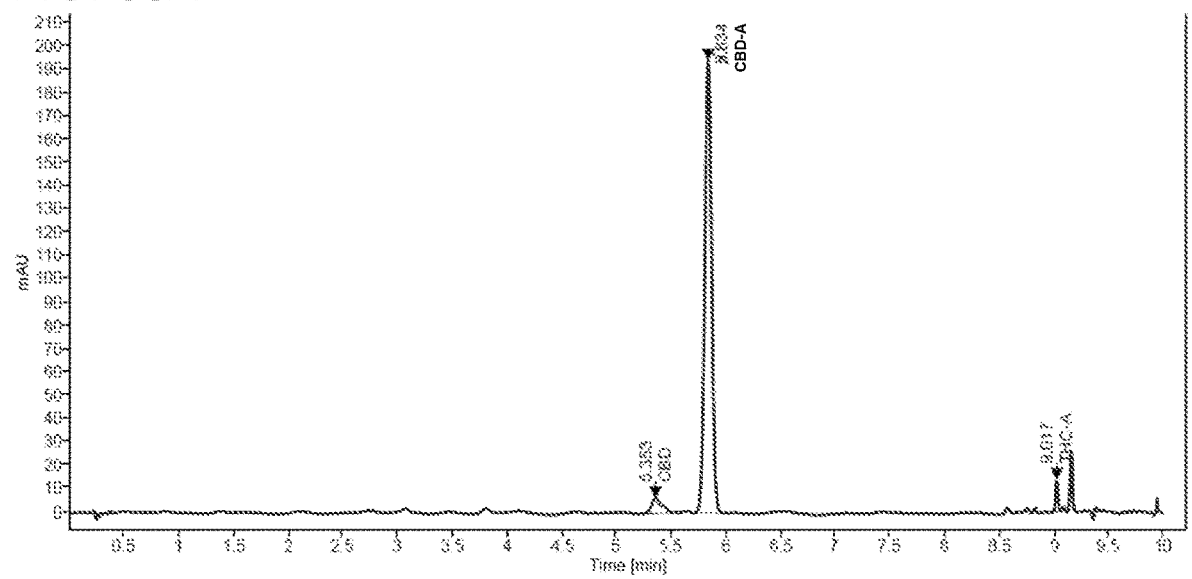
FIG. 30A is an HPLC chromatogram showing the cannabinoid composition of a standardized hemp extract stock used in Example 21.

406.4 g of hemp biomass were ground to a powder and then commingled and mixed with 2.5 l of heptane (6:1 volume/mass ratio) for 25 minutes at ambient temperature. The liquid phase was separated from the biomass by pressure filtration using nitrogen, and then the heptane was removed by distillation under vacuum to produce 40.3 grams of a hemp extract resin containing CBDA. A standardized hemp extract stock solution was prepared by dissolving the hemp extract resin in 769.7 ml heptane to produce a standardized hemp extract stock solution totaling 811.57 ml. The standardized hemp extract stock solution was then spiked with 3.38% v/v denatured ethanol (28.4 ml; 84.15% v/v ethanol, 15% v/v methanol, 0.85% v/v ethyl acetate). The CBDA content in the stock solution was quantified by removing a 20-ul sample of the stock solution, separating the heptane under vacuum, dissolving the resulting resin in 1 ml of HPLC-grade methanol, and further preparing a 10× dilution of the sample in HPLC-grade methanol. The 10× diluted sample was then analyzed by HPLC and the stock solution of hemp extract in heptane was determined to contain 20.217 mg/ml CBDA (FIG. 30A).

Figure 30B:
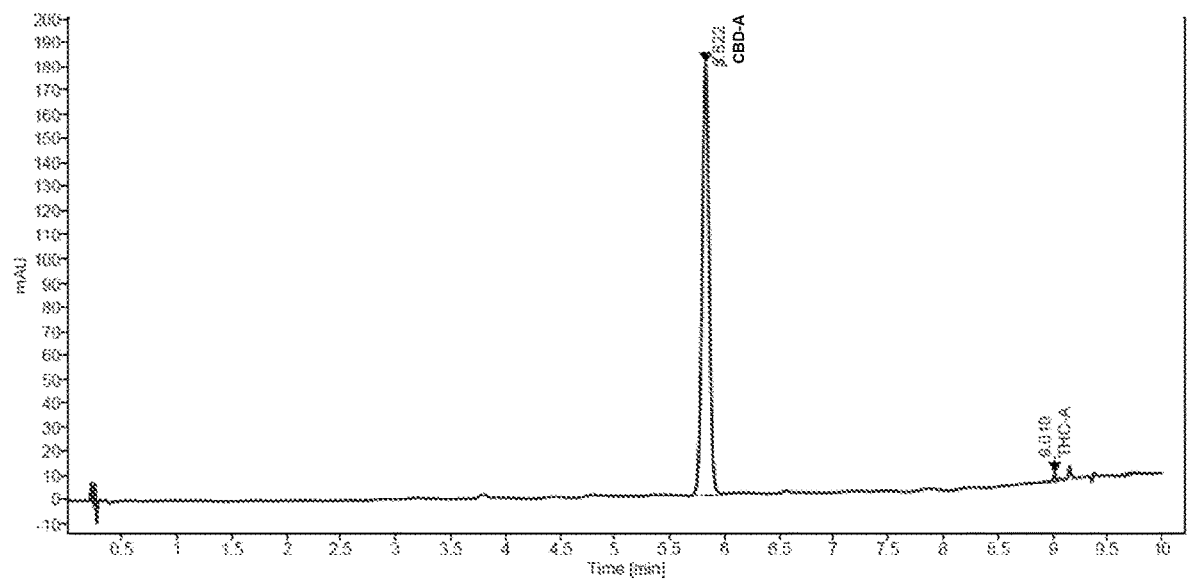
FIG. 30B is an HPLC chromatogram showing the cannabinoid content of a crude CBDA-triethylamine salt precipitated from the standardized hemp extract stock shown in FIG. 30A.

A 3:1 molar ratio of triethylamine (5.7 ml) was added dropwise to a 150-ml aliquot of the spiked hemp extract solution while mixing by magnetic stir bar thereby causing precipitation of a crude CBDA-TEA amine salt. The solid crude CBDA-TEA salt was separated from the liquid phase by vacuum filtration, and washed with 24 ml of cold heptane. The washed crude CBDA-TEA salt was re-slurried in an additional 24 ml of cold heptane, then vacuum filtered, and dried. The washed and dried crude CBDA-TEA salt was analyzed by HPLC (FIG. 30B).

Figure 31A:
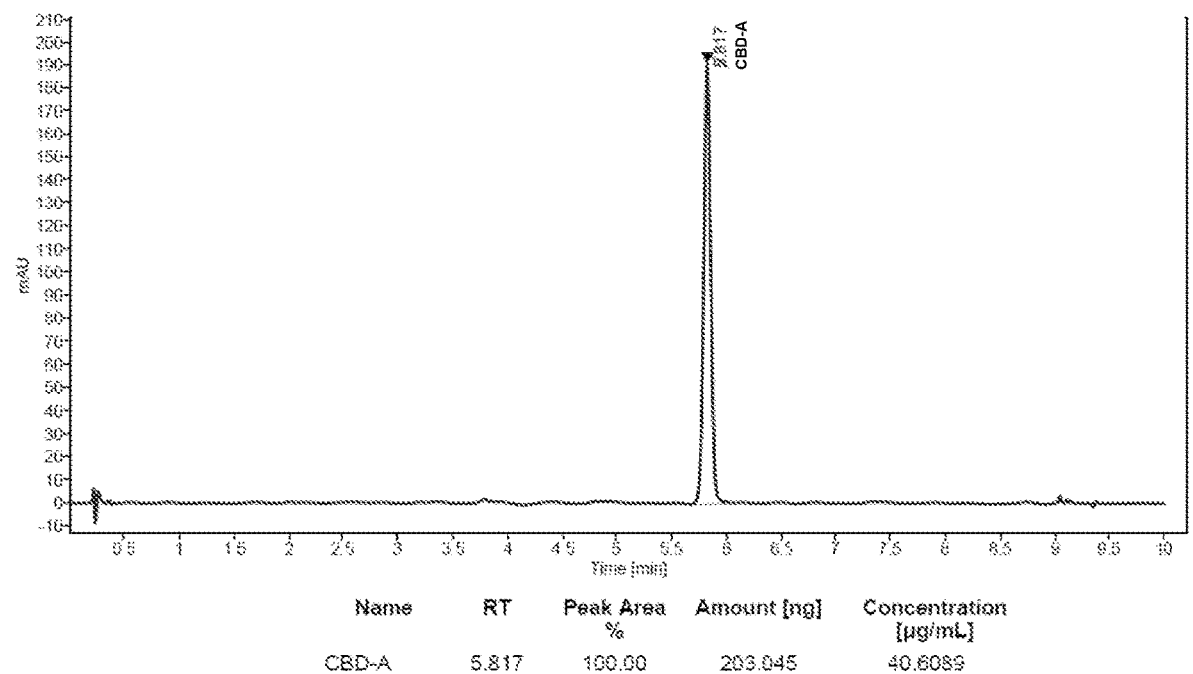
FIG. 31A is an HPLC chromatogram showing the cannabinoid content of a recrystallized purified CBDA-triethylamine salt precipitated from the crude CBDA-triethylamine salt shown in FIG. 30B.
Figure 31B:
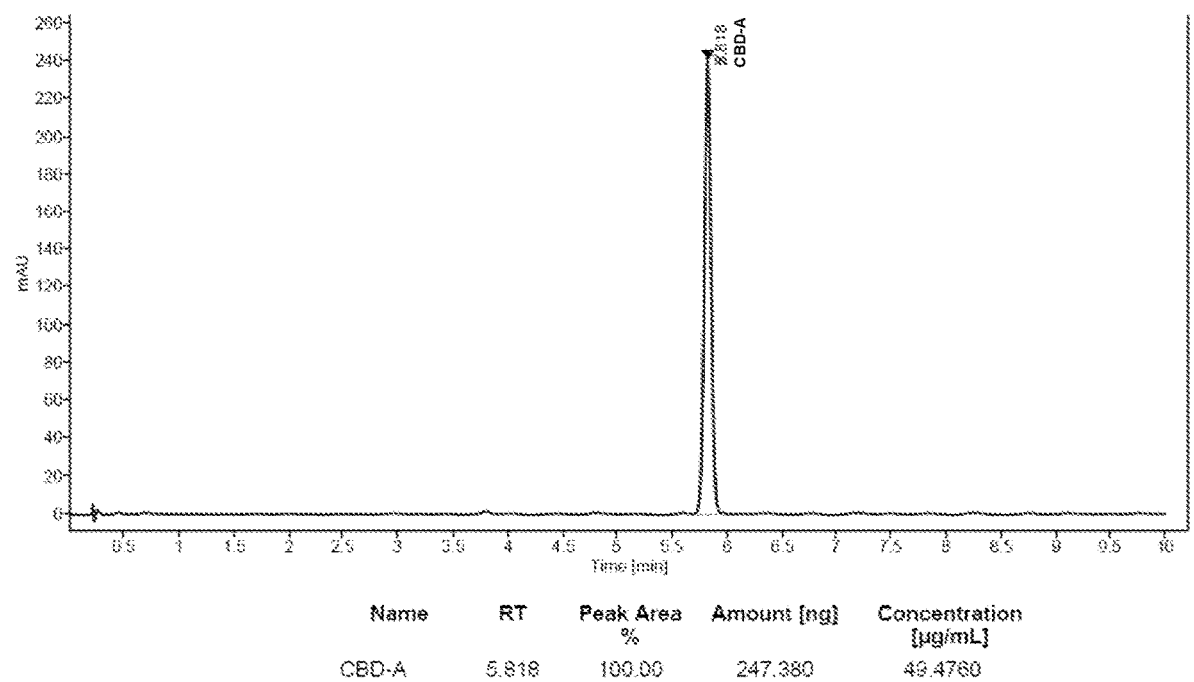
FIG. 31B is an HPLC chromatogram showing the cannabinoid content of a twice-recrystallized purified CBDA-triethylamine salt precipitated from the purified CBDA-triethylamine salt shown in FIG. 31A.

5.232 g of dried crude CBDA-TEA salt were dissolved in a 10:1 volume/mass ratio ethyl acetate (50.3 ml) spiked with 0.754 ml heptane under refluxing conditions (about 76° C.±3° C.) for about 15 min, then cooled slowly under ambient conditions to about 30° C. at which temperature, the rate of recrystallization of a solid purified CBDA-TEA salt increased rapidly. The recrystallizing solution was further cooled and then held at 4° C. for about 16 hr. The recrystallized purified CBDA-TEA salt was then separated from the liquid phase by vacuum filtration, re-slurried with 15 ml cold heptane, filtered and dried under vacuum, and analyzed by HPLC (FIG. 31A). The recrystallized purified CBDA-TEA salt was recrystallized a second time by dissolving 4.208 g of the purified CBDA-TEA salt in 65 ml of ethyl acetate spiked with 0.631 ml heptane under refluxing conditions (about 76° C.±3° C.) for about 15 min, and then cooled slowly under ambient conditions to about 30° C. at which temperature, the rate of precipitation of the solid purified CBDA-TEA salt increased rapidly. The recrystallizing solution was further cooled and held at 4° C. for about 16 hr. The twice recrystallized purified CBDA-TEA salt was then separated from the liquid phase by vacuum filtration, re-slurried with 13 ml cold heptane, then filtered and dried under vacuum, thereby yielding 3.629 g of a highly purified CBDA-TEA salt. A sample of the twice recrystallized purified CBDA-TEA salt was dissolved in methanol and analyzed by HPLC (FIG. 31B).

Figure 32:
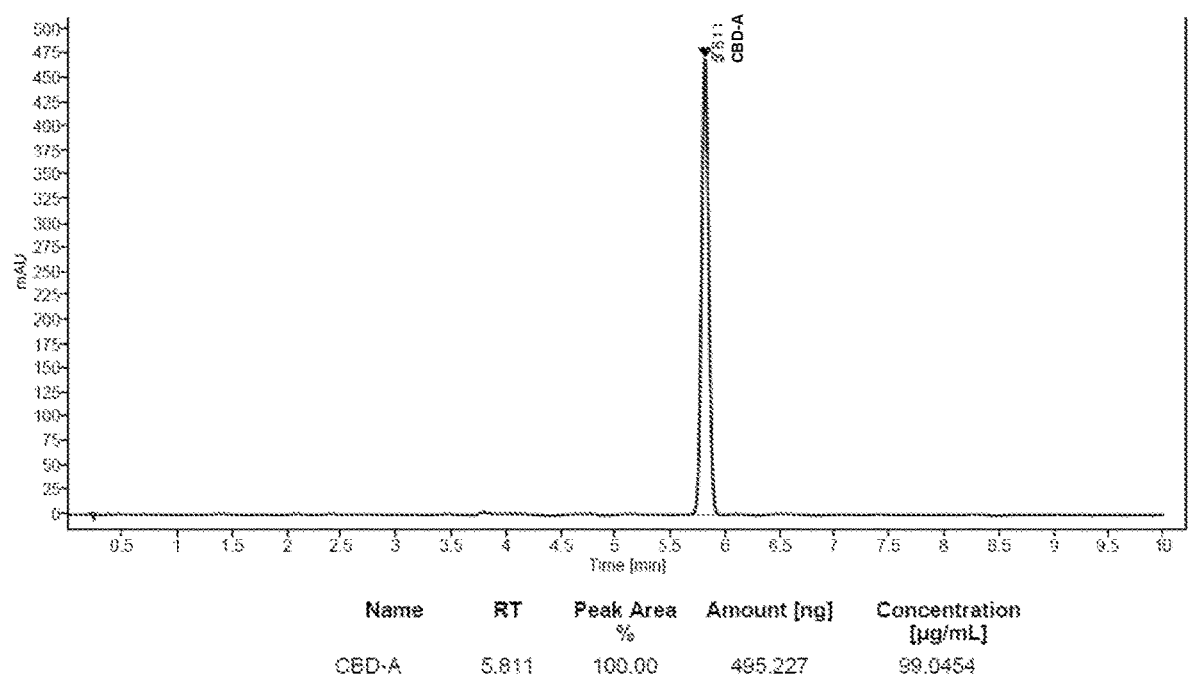
FIG. 32 is an HPLC chromatogram showing the cannabinoid content of a decarboxylated CBD oil recovered from the twice-recrystallized purified CBDA-triethylamine salt shown in FIG. 31B.

3.385 grams of the twice recrystallized purified CBDA-TEA amine salt were dissolved in 51.34 ml dichloromethane. The solution was washed twice with 20 ml of a 5% HCl solution by shaking in a separatory funnel. The aqueous layer containing the TEA-hydrochloride was separated from the organic layer containing the CBDA. The organic layer was dried over magnesium sulfate, gravity filtered and the dichloromethane was removed by distillation, yielding 2.430 grams of crystalline CBDA (FIG. 32).

The invention claimed is:
1. A method for separating, recovering, and purifying a cannabidiolic acid-amine salt (CBDA-amine salt) from an organic solvent solution comprising a mixture of cannabinoids, said method comprising:
providing an organic solvent solution containing therein a complex mixture of cannabinoids;
assaying the organic solvent solution to determine a first concentration of CBDA therein;
adding a volume of an alkane solvent to the organic solvent solution and commingling therewith to adjust the first CBDA concentration to a target concentration value selected from a range of target concentrations, thereby producing a solvent-solubilized solution;
adding an amine to the solvent-solubilized solution and commingling therewith to precipitate therefrom a CBDA-amine salt, wherein said amine is selected from a group consisting of:
a tertiary amine selected from one of triethylamine, tripropylamine, tributyl amine, and quinine, or
a diamine selected from one of N,N,N-trimethylethylenediamine, N,N,N,N-tetramethylethylenediamine, 4-aminomethylpiperidine, 1,5-diazabicyclooctane (DABCO), 4 dimethylaminopyridine (DMAP), 1,5-diazabicyclo[4.3.0]non-5-ene (DBN), 1,8-diazabicycloundec-7-ene (DBU), and dimethylpiperazine, or
a secondary amine selected from one of diisopropylethylamine (Hunig's base), diethylamine, N-isopropylcyclohexylamine, and 2,2,6,6-tertamethylpiperidine, or
an amino alcohol selected from one of piperidineethanol and N,N-dimethylethanolamine, or
an amino ether selected from one of morpholine and N-methylmorpholine, or cyclohexylamine;
separating the precipitated CBDA-amine salt from the solvent-solubilized solution;
washing the recovered CBDA-amine salt at least once with said selected alkane solvent; and
drying the washed CBDA-amine salt to produce the CBDA-amine salt.
2. The method according to claim 1, wherein a selected volume of denatured ethanol or acetone is added to and commingled with the solvent-solubilized solution prior to the addition of the selected amine.
3. The method according to claim 1, wherein the alkane solvent is one of pentane, hexane, heptane, and a low boiling point petroleum ether.

4. The method according to claim 1, wherein the amine is triethylamine and the salt produced is a CBDA-triethylamine salt having a chemical structure (1)

(1)

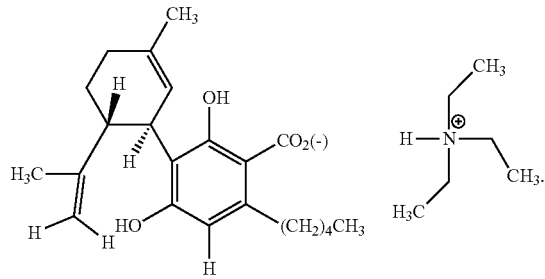

5. The method according to claim 1, wherein the amine is N-methylmorpholine and the salt produced is a CBDA-N-methylmorpholine salt having a chemical structure (2)

(2)

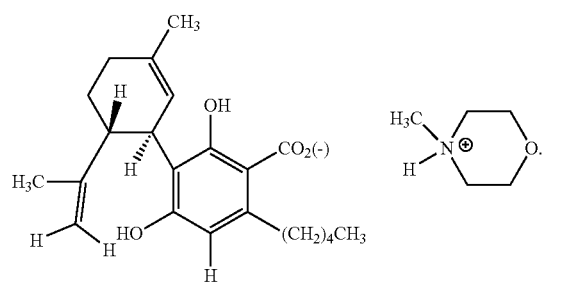

6. The method according to claim 1, wherein the amine is 1,8-diazabicycloundec-7-ene (DBU) and the salt produced is a CBDA-DBU salt having a chemical structure (3)

(3)

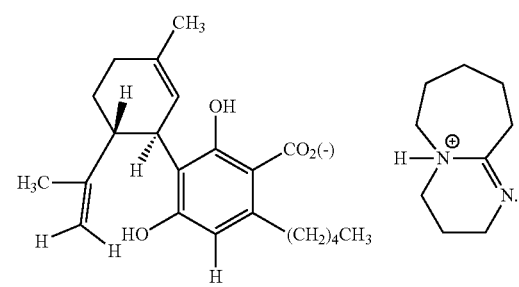

7. The method according to claim 1, wherein the amine is piperidineethanol and the salt produced is a CBDA-piperidineethanol salt having a chemical structure (4)

(4)

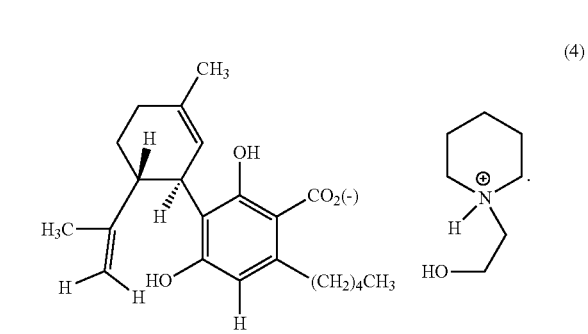

8. The method according to claim 1, wherein the amine is 4-dimethylaminopyridine (DMAP) and the salt produced is a CBDA-DMAP salt having a chemical structure (5)

(5)

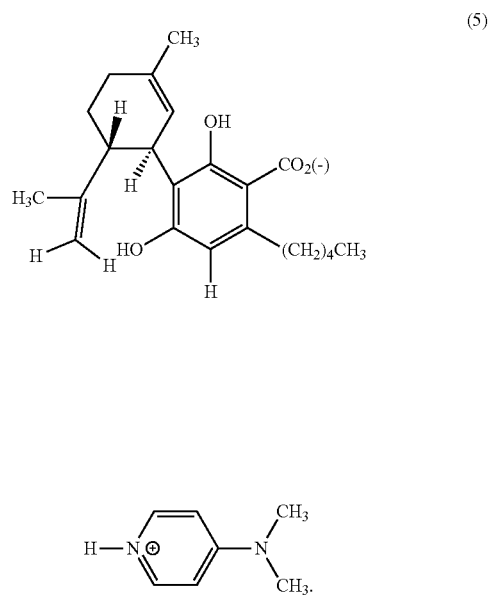

9. The method according to claim 1, wherein the amine is cyclohexylamine and the salt produced is a CBDA-cyclohexylamine salt having a chemical structure (6)

(6)

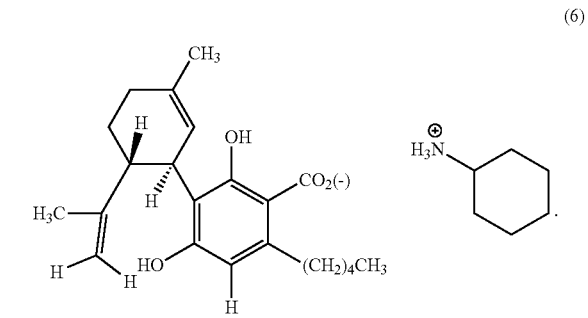

10. The method according to claim 1, wherein the amine is 1,5-diazabicyclooctane (DABCO) and the salt produced is a CBDA-DABCO salt having a chemical structure (7)

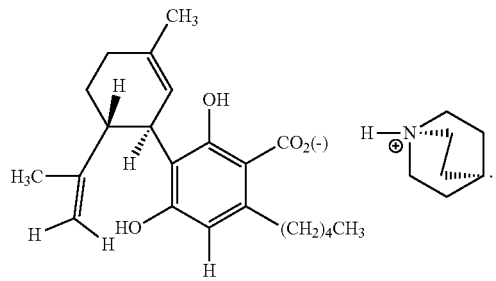

(7)

11. The method according to claim 1, wherein the amine is N,N,N,N-tetramethylethylenediamine (TMEDA) and the salt produced is a CBDA-TMEDA salt having a chemical structure (9)

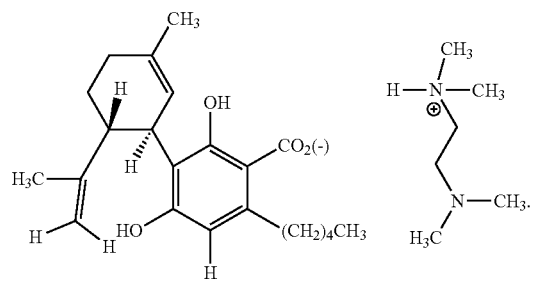

(9)

12. The method according to claim 1, wherein the amine is diisopropylethylamine and the salt produced is a CBDA-diisopropylethylamine salt having a chemical structure (10)

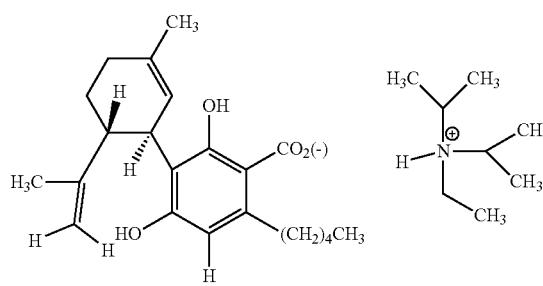

(10)

13. The method according to claim 1, wherein the amine is N-isopropylcyclohexylamine, and the salt produced is a CBDA-N-isopropylcyclohexylamine salt having a chemical structure (11)

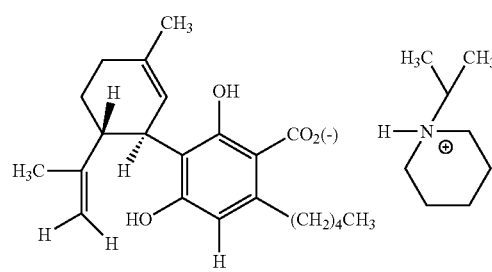

(11)

14. The method according to claim 1, wherein the amine is tributylamine, and the salt produced is a CBDA-tributylamine salt having a chemical structure (12)

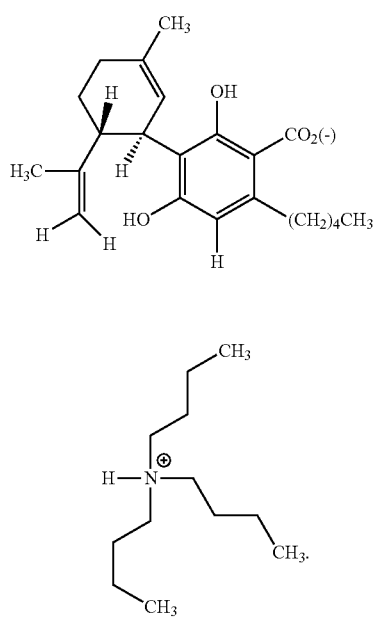

(12)

15. The method according to claim 1, wherein the amine is dimethylpiperazine, and the salt produced is a CBDA-dimethylpiperazine salt having a chemical structure (13)

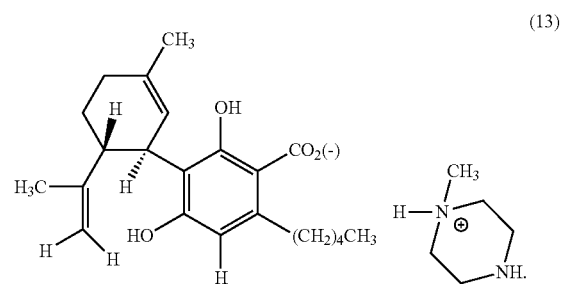

(13)

16. The method according to claim 1, wherein the amine is N,N,N-trimethylethylenediamine, and the salt produced is a CBDA-N,N,N-trimethylethylenediamine salt having a chemical structure (14)

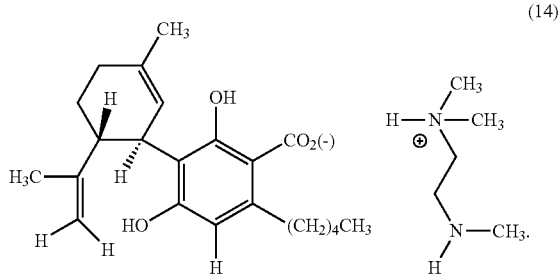
(14)

17. The method according to claim 1, wherein the amine is 2,2,6,6-tetramethylpiperidine, and the salt produced is a CBDA-2,2,6,6-tetramethylpiperidine salt having a chemical structure (15)

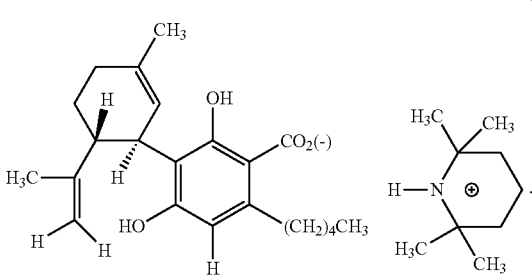
(15)

18. The method according to claim 1, wherein the amine is morpholine, and the salt produced is a CBDA-morpholine salt having a chemical structure (16)

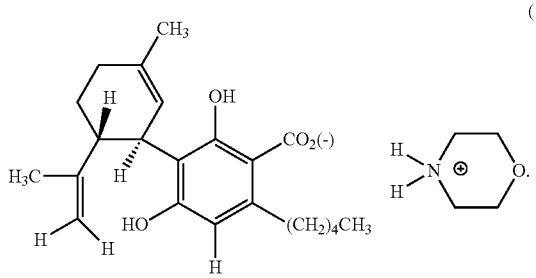
(16)

19. The method according to claim 1, wherein the amine is N,N-dimethylethanolamine, and the salt produced is a CBDA-N,N-dimethylethanolamine salt having a chemical structure (17)

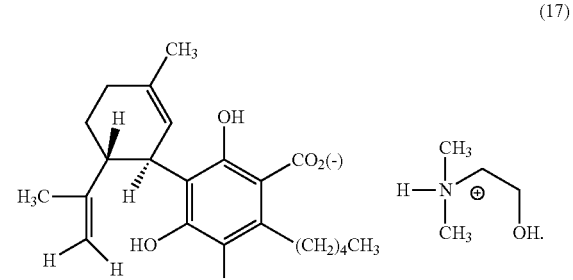
(17)

20. The method according to claim 1, wherein the amine is quinine, and the salt produced is a CBDA-quinine salt having a chemical structure (18)

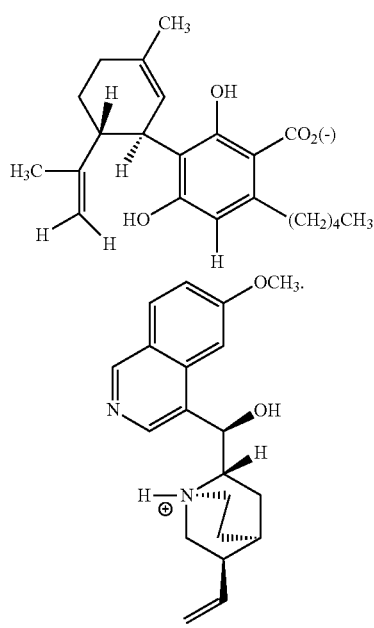
(18)

21. The method according to claim 1, wherein the amine is diethylamine, and the salt produced is a CBDA-diethylamine salt having a chemical structure

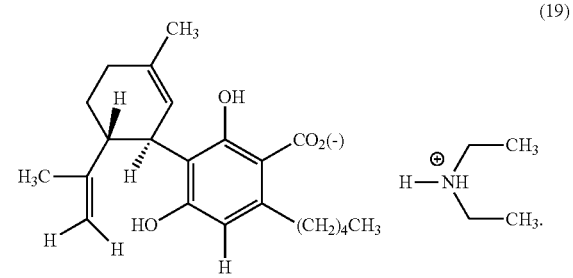
(19)

22. The method according to claim 1, wherein the amine is tripropylamine, and the salt produced is a CBDA-tripropylamine salt having a chemical structure
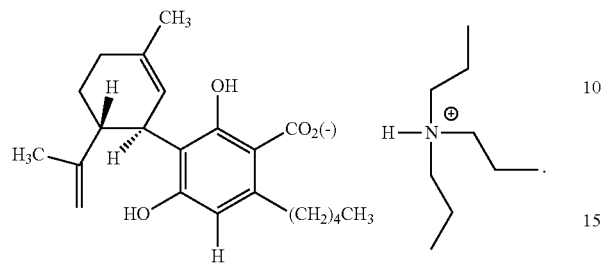
(20)